United States Patent
Shibayama et al.

(10) Patent No.: US 12,325,746 B2
(45) Date of Patent: Jun. 10, 2025

(54) BISPECIFIC ANTIBODY

(71) Applicant: ONO PHARMACEUTICAL CO., LTD., Osaka (JP)

(72) Inventors: Shiro Shibayama, Tsukuba (JP); Tomoya Tezuka, Tsukuba (JP); Mark Throsby, Utrecht (NL); Cornelis Adriaan De Kruif, Utrecht (NL); Pieter Fokko Van Loo, Utrecht (NL); Rinse Klooster, Utrecht (NL); Robertus Cornelis Roovers, Utrecht (NL)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 920 days.

(21) Appl. No.: 17/601,354

(22) PCT Filed: Apr. 3, 2020

(86) PCT No.: PCT/JP2020/015266
§ 371 (c)(1),
(2) Date: Oct. 4, 2021

(87) PCT Pub. No.: WO2020/204152
PCT Pub. Date: Oct. 8, 2020

(65) Prior Publication Data
US 2022/0185885 A1  Jun. 16, 2022

(30) Foreign Application Priority Data

Apr. 4, 2019 (JP) .................................. 2019-071840
Feb. 13, 2020 (JP) .................................. 2020-022256

(51) Int. Cl.
C07K 16/28 (2006.01)
A61K 39/00 (2006.01)

(52) U.S. Cl.
CPC ...... *C07K 16/2803* (2013.01); *C07K 16/2818* (2013.01); *A61K 2039/505* (2013.01); *C07K 2317/31* (2013.01); *C07K 2317/33* (2013.01)

(58) Field of Classification Search
None
See application file for complete search history.

(56) References Cited

U.S. PATENT DOCUMENTS

2006/0034826 A1   2/2006  Carreno et al.
2008/0025979 A1   1/2008  Honjo et al.
(Continued)

FOREIGN PATENT DOCUMENTS

CN       106939050 A      7/2017
EP        2193146         6/2010
(Continued)

OTHER PUBLICATIONS

Office Action dated Aug. 21, 2024, issued by Singapore Patent Center in Singapore Patent Application No. 11202110993Q.
(Continued)

*Primary Examiner* — Amy E Juedes
*Assistant Examiner* — Hilary Ann Petrash
(74) *Attorney, Agent, or Firm* — Sughrue Mion, PLLC

(57) ABSTRACT

An agent for preventing, suppressing the progression of symptoms of, suppressing the recurrence of or treating autoimmune diseases, comprising a bispecific antibody or an antibody fragment thereof, having a first arm specifically binding to PD-1 and a second arm specifically binding to CD19, as described herein.

6 Claims, 14 Drawing Sheets

Specification includes a Sequence Listing.

| Common Light Chain | SEQ ID No. | Amino Acid Sequence |
|---|---|---|
| Variable Region | 25 | DIQMTQSPSSLSASVGDRVTITCRASQSISSYLNWYQQKPGKAPK LLIYAASSLQSGVPSRFSGSGSGTDFTLTISSLQPEDFATYYCQQS YSTPPTFGQGTKVEIK |
| Constant Region | 29 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |

(56) References Cited

U.S. PATENT DOCUMENTS

| | | |
|---|---|---|
| 2009/0053240 A1 | 2/2009 | Lazar et al. |
| 2009/0076250 A1 | 3/2009 | Honjo et al. |
| 2009/0263865 A1 | 10/2009 | Honjo et al. |
| 2010/0298542 A1 | 11/2010 | Igawa et al. |
| 2011/0280878 A1 | 11/2011 | Honjo et al. |
| 2013/0164294 A1 | 6/2013 | Honjo et al. |
| 2014/0220021 A1 | 8/2014 | Shibayama et al. |
| 2015/0118234 A1 | 4/2015 | Honjo et al. |
| 2017/0320949 A1 | 11/2017 | Shibayama et al. |
| 2018/0312604 A1 | 11/2018 | Throsby et al. |
| 2020/0317783 A1 | 10/2020 | Shibayama et al. |
| 2020/0325227 A1 | 10/2020 | Geuijen et al. |
| 2021/0214441 A1 | 7/2021 | Shibayama et al. |
| 2021/0332134 A1 | 10/2021 | Shibayama et al. |

FOREIGN PATENT DOCUMENTS

| | | |
|---|---|---|
| JP | 2008-537941 A | 10/2008 |
| JP | 2011-525808 A | 9/2011 |
| JP | 2019-500405 A | 1/2019 |
| SG | 11202007531 A1 | 9/2020 |
| WO | 03/011911 A1 | 2/2003 |
| WO | 2004/072286 A1 | 8/2004 |
| WO | 2006/105338 A2 | 10/2006 |
| WO | 2008/092117 A2 | 7/2008 |
| WO | 2009/036379 A2 | 3/2009 |
| WO | 2009/041613 A1 | 4/2009 |
| WO | 2009/157771 A2 | 12/2009 |
| WO | 2013/022091 A1 | 2/2013 |
| WO | 2019/009726 A1 | 1/2019 |
| WO | 2019/070047 A1 | 4/2019 |
| WO | 2019/156199 A1 | 8/2019 |

OTHER PUBLICATIONS

Office Action issued Mar. 22, 2024 by the European Patent Office in European Patent Application No. 18865322.4.
Spiess et al., "Alternative molecular formats and therapeutic applications for bispecific antibodies", Molecular Immunology, Jan. 27, 2015, pp. 95-106, 12 pages total.
Brinkmann et al., "The making Of bispecific antibodies", MABS, Jan. 10, 2017, pp. 182-212, 32 pages total.
Related U.S. Appl. No. 16/753,159.
International Search Report dated Nov. 6, 2018 issued by the International Searching Authority in related International Application No. PCT/JP2018/037311 (PCT/ISA/210).
Written Opinion dated Nov. 6, 2018 issued by the International Searching Authority related International Application No. PCT/JP2018/037311 (PCT/ISA/237).
Extended European Search Report dated May 31, 2021, issued by the European Patent Office in related European patent Application No. 18865322.4.
International Search Report dated Jun. 23, 2020 issued by the International Searching Authority in counterpart International Application No. PCT/JP2020/015266 (PCT/ISA/210).
International Written Opinion dated Jun. 23, 2020 issued by the International Searching Authority in counterpart International Application No. PCT/JP2020/015266 (PCT/ISA/237).
Sebastian Kobold et al., "Rationale for Combining Bispecific T Cell Activating Antibodies With Checkpoint Blockade for Cancer Therapy", Frontiers in Oncology, vol. 8, Article 285, Jul. 2018, 8 pages total.
Office Action dated May 5, 2023, issued by the Indonesian Intellectual Property Office in Indonesian Patent Application No. P00202108261).
Communication dated Oct. 2, 2024, issued by Intellectual Property Corporation of Malaysia in Malaysian Application No. PI2021005829.
Office Action dated Jan. 30, 2024, issued by Japanese Patent Office in Japanese Patent Application No. 2023-020514.
Communication issued on Jun. 21, 2024 by the New Zealand Patent Office in NZ Patent Application No. 780860.
Office Action dated Jun. 16, 2023, issued by the United States Patent and Trademark Office in U.S. Appl. No. 16/753,159.
Rudikoff et al., "Single amino acid substitutions altering antigen-binding specificity," Proceedings of the National Academy of Sciences of the United States of America, vol. 79, pp. 1979-1983, Mar. 1982.
Colman, "Effects of amino acid sequence changes on antibody-antigen interactions," Research in Immunology, vol. 145, No. 1, 1994, Total 5 pages.
D'Angelo et al., "Many Routes to an Antibody Heavy-Chain CDR3: Necessary, Yet Insufficient, for Specific Binding," Frontiers in Immunology, vol. 9, Article 395, Mar. 2018; Total 13 pages, doi:10.3389/fimmu.2018.00395.
Piche-Nicholas et al., "Changes in complemetarity-determining regions significantly alter IgG binding to the neonatal Fc receptor (FcRN) and pharmacokinetics," MABS, vol. 10, No. 1, pp. 81-94, 2018, doi.org/10.1080/19420862.2017.1389355.
Office Action dated Dec. 22, 2023, issued by the United States Patent and Trademark Office in U.S. Appl. No. 16/753,159.
Communication dated Nov. 22, 2022 issued by the European Patent Office in EP application No. 20782232.1.
Camilla De Nardis et al., "A new approach for generating bispecific antibodies based on a common light chain format and the stable architecture of human immunoglobulin G1", J. Biol. Chem., 2017, vol. 292(35), pp. 14706-14717.
Suya Dai et al., "The PD-1/PD-Ls pathway and autoimmune diseases", Cellular Immunology, 2014, vol. 290, Issue 1, pp. 72-79.
Office Action issued on Jul. 26, 2023 by the Russian Patent Office in corresponding RU Patent Application No. 2021128262.
Office Action issued on Jul. 20, 2023 by the Singapore Patent Office in corresponding SG Patent Application No. 11202110993Q.
Communication issued Jul. 26, 2022 by the Japanese Patent Office for Japanese Patent Application No. 2019-547025.
Office Action issued on Nov. 6, 2023 by the Chinese Patent Office in corresponding CN Patent Application No. 202080026225.8.
Nora Hornig et al., "Production of Bispecific Antibodies: Diabodies and Tandem scFv", Chapter 40, Patrick Chames (ed.), Antibody Engineering: Methods and Protocols, Second Edition, Methods in Molecular Biology, vol. 907, 2012, pp. 713-727, DOI: 10.1007/978-1-61779-974-7_40.
Fa Yang et al., "Bispecific Antibodies as a Development Platform for New Concepts and Treatment Strategies", International Journal of Molecular Sciences, 2017 (published Dec. 28, 2016), vol. 18, No. 1, Article No. 48, 21 pages, DOI: 10.3390/ijms18010048.
Office Action issued on May 20, 2024 by the United States Patent and Trademark Office for the U.S. Appl. No. 16/753,159.
Communication dated Nov. 26, 2024, issued by the Japanese Patent Office in Japanese Application No. 2023-198746.
Office Action dated Dec. 20, 2024, issued by the United States Patent and Trademark Office in U.S. Appl. No. 16/753,159.
Shimpei Kasagi et al., "Anti-Programmed Cell Death 1 Antibody Reduces $CD4^+PD-1^+$ T Cells and Relieves the Lupus-Like Nephritis of NZB/W F1 Mice," The Journal of Immunology (2010) 184:2337-47. doi: 10.4049/jimmunol.0901652 (Year: 2010), total 11 pages.
Maida Wong et al., "Blockade of Programmed Death-1 in Young (New Zealand Black x New Zealand White)$F_1$ Mice Promotes the Activity of Suppressive $CD8^+$T Cells That Protect from Lupus-Like Disease," The Journal of Immunology (2010) 185:6563-71. doi: 10.4049/jimmunol.0903401 (Year: 2010). total 9 pages.
Maida Wong et al., "Blockade of Programmed Death-1 in young (New Zealand Black x New Zealand White)$F_1$ Mice Promotes the Suppressive Capacity of $CD4^+$ Regulatory T Cells Protecting from Lupus-Like Disease," The Journal of Immunology (2013) 190:5402-10. doi: 10.4049/jimmunol.1202382 (Year: 2013), total 9 pages.
Communication dated Jan. 23, 2025, issued by the Intellectual Property Office of Vietnam in Vietnamese Application No. 1-2021-06036.
Substantive Examination Report issued on Mar. 7, 2025 by the Intellectual Property Office of the Philippines Bureau of Patents in Philippines Patent Application No. 1/2021/552501.

[Figure 1]

| Common Light Chain | SEQ ID No. | Amino Acid Sequence |
|---|---|---|
| Variable Region | 25 | DIQMTQSPSSLSASVGDRVTITCRASQSISSYLNWYQQKPGKAPK LLIYAASSLQSGVPSRFSGSGSGTDFTLTISSLQPEDFATYYCQQS YSTPPTFGQGTKVEIK |
| Constant Region | 29 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |

[Figure 2]

| Common Light Chain | SEQ ID No. | CDR1 | SEQ ID No. | CDR2 | SEQ ID No. | CDR3 |
|---|---|---|---|---|---|---|
| CDRs | 26 | RASQSISSYLN | 27 | AASSLQS | 28 | QQSYSTPPT |

[Figure 3]

| Germline V gene | SEQ ID No. | Amino Acid Sequence |
|---|---|---|
| IGHV7-4-1 | 21 | QVQLVQSGSELKKPGASVKVSCKASGYTFTSYAMNWVRQ APGQGLEWMGWINTNTGNPTYAQGFTGRFVFSLDTSVST AYLQICSLKAEDTAVYYCAR |
| IGHV5-51 | 22 | EVQLVQSGAEVKKPGESLKISCKGSGYSFTSYWIGWVRQM PGKGLEWMGIYPGDSDTRYSPSFQGQVTISADKSISTAYLQ WSSLKASDTAMYYCAR |

[Figure 4]

Alignment between the respective VH of PD1-1 to PD1-5 and IGHV7-4-1/JH6c

```
                         ---------FR1---------  -CDR1-  ---FR2----  -----CDR2-----
IGHV7-4-1 (SEQ ID No.21) QVQLVQSGSELKKPGASVKVSCKASGYTFT  STAMN   WVRQAPGQGLEWMG  WINTNTGNPTYAQGFTG
PD1-1 VH (SEQ ID No. 1)  |------------Q-------------|   |-GLH|  |H-GLH|         |-L-----E-----F--|
PD1-2 VH (SEQ ID No. 2)  |------------Q--Y----------|   |----|  |H-GLH|         |----------------|
PD1-3 VH (SEQ ID No. 3)  |----------------M---------|   |----|  |H--LH|         |------E---------|
PD1-4 VH (SEQ ID No. 4)  |------------Q-------------|   |----|  |H--LH|  |-L-|  |-L----E-----F---|
PD1-5 VH (SEQ ID No. 5)  |------------Q-------------|   |----|  |H--LH|  |-L-|  |------E-----F---|

-----------FR3-----------  -------CDR3-------  ---FR4---
IGHV7-4-1 (SEQ ID No.21) RFVFSLDTSVSTAYLQICSLKAEDTAVYYCAR
D gene (unknown)                                     HYYYYYMDV
JH6c                                                                     WGRGTTVTVSS
PD1-1 VH(SEQ ID No. 1)   |--------T-------S---------|  |GDMVPTTIWN--HF--|  |--N--L--|
PD1-2 VH(SEQ ID No. 2)   |----------------S---------|  |GDLVPTTIWN--H-E-|  |------L-|
PD1-3 VH(SEQ ID No. 3)   |--------T-------S---------|  |GDMVPTTIWN--HF--|  |--------|
PD1-4 VH(SEQ ID No. 4)   |--------T-------S---------|  |GDMVPTTIWN--HF--|  |--N-----|
PD1-5 VH(SEQ ID No. 5)   |--------T-------S---------|  |GDMVPTTIWN--HF--|  |-----Q--|
```

[Figure 5]

Alignment between each VH of CD19-1 to CD19-6 and IGHV5-51

```
                         -------FR1-------            -CDR1-     --FR2--          ---CDR2---
IGHV5-51  (SEQ ID No. 22) |EVQLVQSGAEVKKPGESLKISCKGSGYSFT| |SYWIG| |WVRQMPGKGLEWMG| |IIYPGDSDTRYSPSFQG|
CD19-5 VH (SEQ ID No. 30) |Q-----------------------------| |-----| |--------------| |-----------------|
CD19-1 VH (SEQ ID No. 31) |------------------------------| |-----| |--------------| |-----------------|
CD19-4 VH (SEQ ID No. 32) |Q-------------S-------------F-| |-----| |-------A------| |-----------------|
CD19-2 VH (SEQ ID No. 33) |Q----------------------------I| |-----| |--------------| |---W-------------|
CD19-3 VH (SEQ ID No. 34) |------------------------------| |-----| |--------------| |-----------------|
CD19-6 VH (SEQ ID No. 30) |Q-----------------------------| |-----| |--------------| |-----------------|

---------FR3---------              ----CDR3----    --FR4---
IGHV5-51  (SEQ ID No. 22) |QVTISADKSISTAYLQWSSLKASDTAMYYCAR|
CD19-5 VH (SEQ ID No. 30) |-----------------------I-------| |RTIYGVVMTAFDI| |WGQGTMVTVSS|
CD19-1 VH (SEQ ID No. 31) |--------------------------V----| |QTIVATVMNAFDI| |WGQGTTVTVSS|
CD19-4 VH (SEQ ID No. 32) |-------FT-----N-------------I--| |RTIVATIYNAFDF| |WGQGTMVTVSS|
CD19-2 VH (SEQ ID No. 33) |--------NV--------L---V--------| |QTIVATTGLAFDI| |WGQGTLVTVSS|
CD19-3 VH (SEQ ID No. 34) |--------------N----------------| |RTIVATDWASDY| |WGQGTMVTVSS|
CD19-6 VH (SEQ ID No. 30) |-------------------------------I| |KTIYGVVMTAFDI| |WGRGTMVTVSS|
```

[Figure 6]

| Clone No. | SEQ ID No. | Amino Acid Sequence |
|---|---|---|
| PD1-1 | 1 | QVQLVQSGSELKQPGASVKVSCKASGYTFTHYGLHWVRQAPGQGLEWMGWLNTNTENPTFAQGFTGRFVFSLDTSVTTAYLQISSLKAEDTAVYYCARGDMVVPTTIWNYYHFMDVWGNGTLVTVSS |
| PD1-2 | 2 | QVQLVQSGSELKQPGVSVKVSCKASGYTFTHYGLHWVRQAPGQGLEWMGWINTNTGNPTYAQGFTGRFVFSLDTSVSTAYLQISSLKAEDTAVYYCARGDLVVPTTIWNYYHYMEVWGKGTLVTVSS |
| PD1-3 | 3 | QVQLVQSGSELKKPGASVMVSCKASGYTFTHYALHWVRQAPGQGLEWMGWLNTNTENPTYAQGFTGRFVFSLDTSVTTAYLQINSLKAEDTAVYYCARGDMVVPTTIWNYYYYMDVWGKGTTVTVSS |
| PD1-4 | 4 | QVQLVQSGSELKQPGASVKVSCKASGYTFTHYALHWLRQAPGQGLEWMGWLNTNTENPTFAQGFTGRFVFSLDTSVTTAYLQISSLKAEDTAVYYCARGDMVVPTTIWNYYHFMDVWGNGTTVTVSS |
| PD1-5 | 5 | QVQLVQSGSELKQPGASVKVSCKASGYTFTHYALHWLRQAPGQGLEWMGWLNTNTENPTFAQGFTGRFVFSLDTSVTTAYLQISSLKAEDTAVYYCARGDMVVPTTIWNYYHFMDVWGQGTTVTVSS |

[Figure 7]

| Clone No. | SEQ ID No. | CDR1 | SEQ ID No. | CDR2 | SEQ ID No. | CDR3 |
|---|---|---|---|---|---|---|
| PD1-1 | 6 | HYGLH | 7 | WLNTNTENPTFAQGFTG | 8 | GDMVVPTTIWNYYHFMDV |
| PD1-2 | 9 | HYGLH | 10 | WINTNTGNPTYAQGFTG | 11 | GDLVVPTTIWNYYHYMEV |
| PD1-3 | 12 | HYALH | 13 | WLNTNTENPTYAQGFTG | 14 | GDMVVPTTIWNYYYYMDV |
| PD1-4 | 15 | HYALH | 16 | WLNTNTENPTFAQGFTG | 17 | GDMVVPTTIWNYYHFMDV |
| PD1-5 | 18 | HYALH | 19 | WLNTNTENPTFAQGFTG | 20 | GDMVVPTTIWNYYHFMDV |

[Figure 8]

| Clone No. | SEQ ID No. | Amino Acid Sequence |
|---|---|---|
| CD19-5 | 30 | QVQLVQSGAEVKKPGESLKISCKGSGYSFTSYWIGWVRQMPGKGLEWMGIIYPGDSDTRYSPSFQGQVTISADKSISTAYLQWSSLKASDTAIYYCARKTIVGVVMTAFDIWGQGTMVTVSS |
| CD19-1 | 31 | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCVRQTIVATVMNAFDIWGQGTTVTVSS |
| CD19-4 | 32 | QVQLVQSGAEVKKSGESLKISCKGSGFSFTSYWIAWVRQMPGKGLEWMGIIYPGDSDTRYSPSFQGQVTISADKSFTTAYLQWNSLKASDTAIYYCARHTIVATIYNAFDFWGQGTMVTVSS |
| CD19-2 | 33 | QVQLVQSGAEVKKPGESLKISCKGSGYSFISYWIGWVRQMPGKGLEWMGIIWPGDSDTRYSPSFQGQVTISADKSINVAYLQWSSLKASDTALYYCVRQTIVATTGLAFDIWGQGTLVTVSS |
| CD19-3 | 34 | EVQLVQSGAEVKKPGESLKISCKGSGYSFTSYWIGWVRQMPGKGLEWMGIIYPGDSDTRYSPSFQGQVTISADKSINTAYLQWSSLKASDTAMYYCARRTIVATIHWASDYWGQGTMVTVSS |
| CD19-6 | 62 | QVQLVQSGAEVKKPGESLKISCKGSGYSFTSYWIGWVRQMPGKGLEWMGIIYPGDSDTRYSPSFQGQVTISADKSISTAYLQWSSLKASDTAIYYCARKTIVGVVMTAFDIWGRGTMVTVSS |

[Figure 9]

| Clone No. | SEQ ID No. | CDR1 | SEQ ID No. | CDR2 | SEQ ID No. | CDR3 |
|---|---|---|---|---|---|---|
| CD19-5 | 35 | SYWIG | 36 | IIYPGDSDTRYSPSFQG | 37 | KTIVGVVMTAFDI |
| CD19-1 | 38 | SYWIG | 39 | IIYPGDSDTRYSPSFQG | 40 | QTIVATVMNAFDI |
| CD19-4 | 41 | SYWIA | 42 | IIYPGDSDTRYSPSFQG | 43 | HTIVATIYNAFDF |
| CD19-2 | 44 | SYWIG | 45 | IIWPGDSDTRYSPSFQG | 46 | QTIVATTGLAFDI |
| CD19-3 | 47 | SYWIG | 48 | IIYPGDSDTRYSPSFQG | 49 | RTIVATIHWASDY |

[Figure 10]

| | SEQ ID No. | Amino Acid Sequence |
|---|---|---|
| Heavy chain constant region having the VH of the first arm specifically binding to PD-1 | 23 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPP CPAPELGRGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISK AKGQPREPQVYTDPPSREEMTKNQVSLTCEVKGFYPSDIAVEWESNGQPENNYK TTPPVLDSDGSFFLYSKLTVDKSRWQQGNVFSCSVMHEALHNHYTQKSLSLSPG |
| Heavy chain constant region having the VH of the second arm specifically binding to CD19 | 24 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPP CPAPELGRGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISK AKGQPREPQVYTKPPSREEMTKNQVSLKCLVKGFYPSDIAVEWESNGQPENNYK TTPPVLDSDGSFFLYSKLTVDKSRWQQGNVFSCSVMHEALHNHYTQKSLSLSPG |
| Heavy chain constant region having the VH of the second arm specifically binding to CD19 | 71 | ASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPP CPAPELGRGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISK AKGQPREPQVYTKPPSREEMTKNQVSLKCLVKGFYPSDIAVEWESNGQPENNYK TTPPVLDSDGSFFLYSKLTVDKSRWQQGNVFSCSVMHEALHNHYTQKSLSLSPGK GKKA |

[Figure 11]

| | Human CD19 | Human PD-1 |
|---|---|---|
| Clone No. | Kd (nmol/L) | Kd (nmol/L) |
| CD19-1(Bi) | 11.3 | 7.6 |
| CD19-2(Bi) | 13.6 | 6.7 |
| CD19-3(Bi) | 5.7 | 6.8 |
| CD19-4(Bi) | 12.5 | 6.7 |
| CD19-5(Bi) | 6.6 | 7.6 |
| CD19-6(Bi) | 3.1 | 1.4 |

[Figure 12]
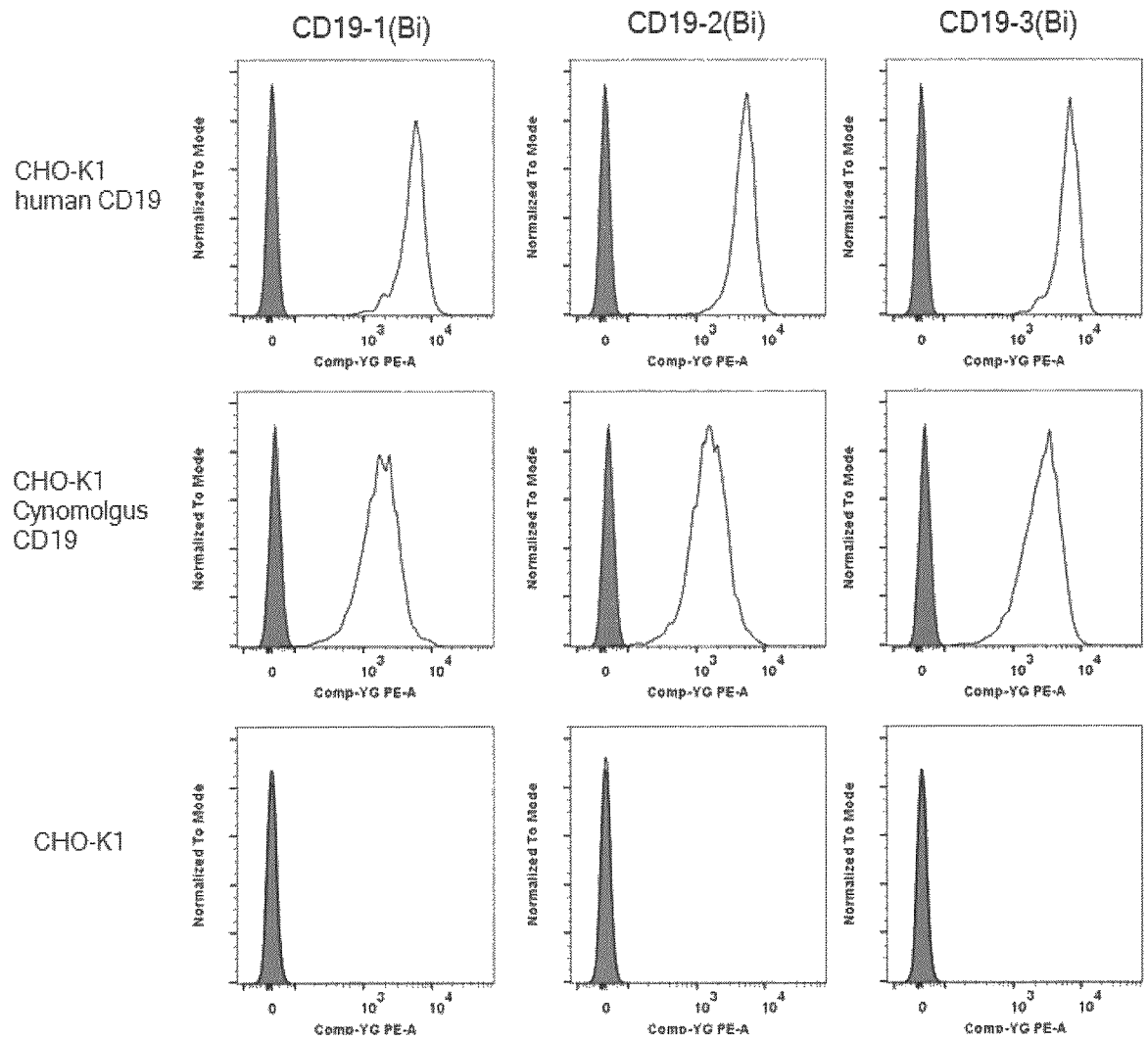

[Figure 13]
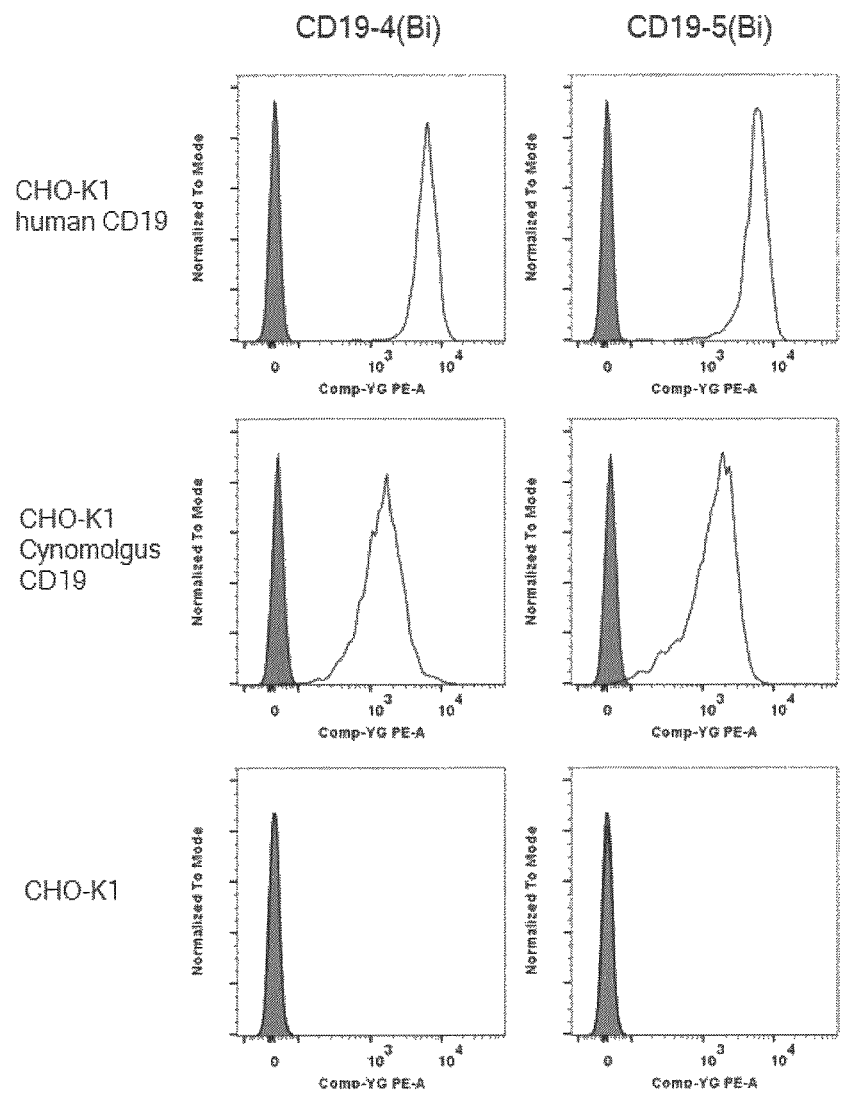

[Figure 14]
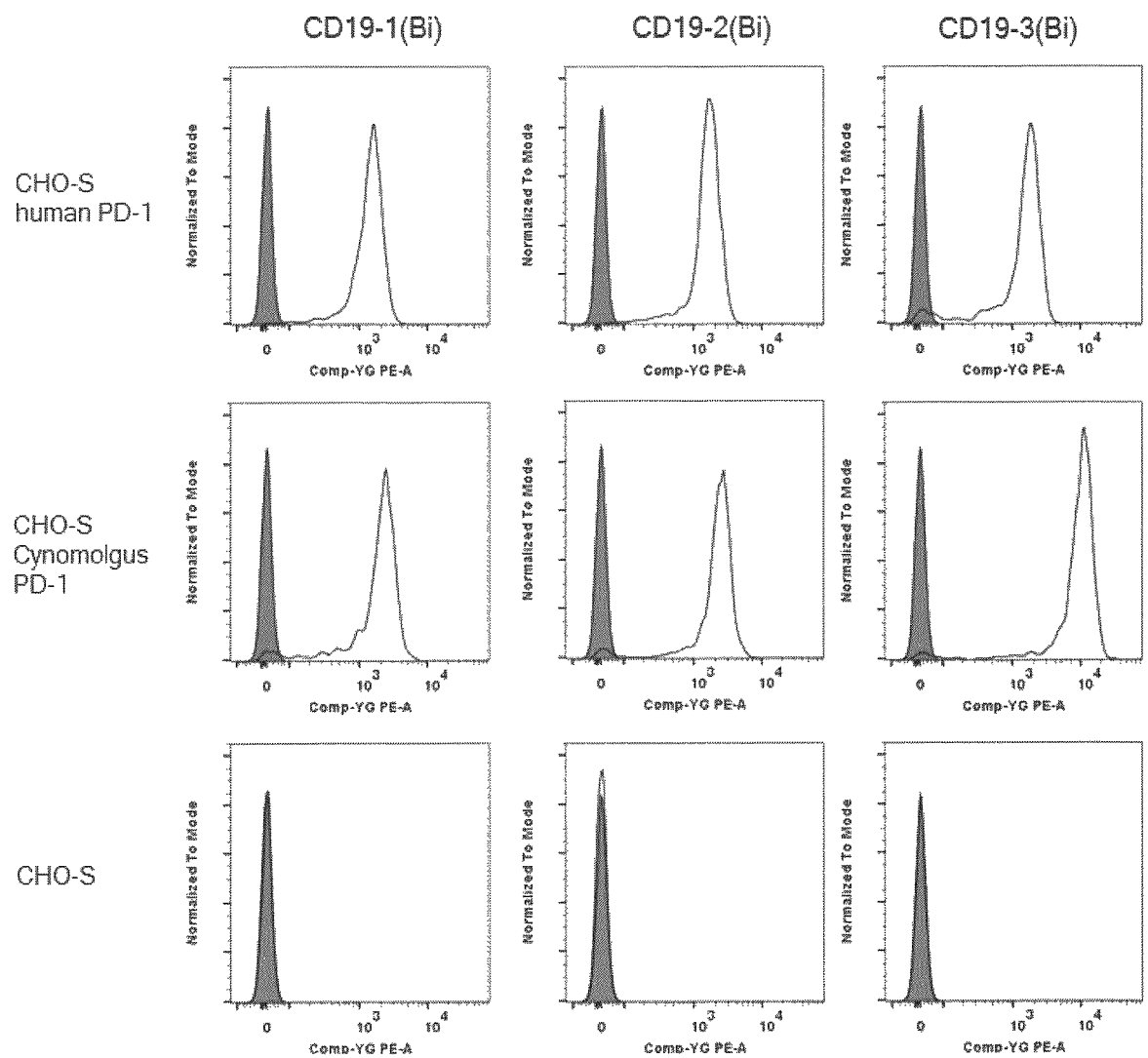

[Figure 15]
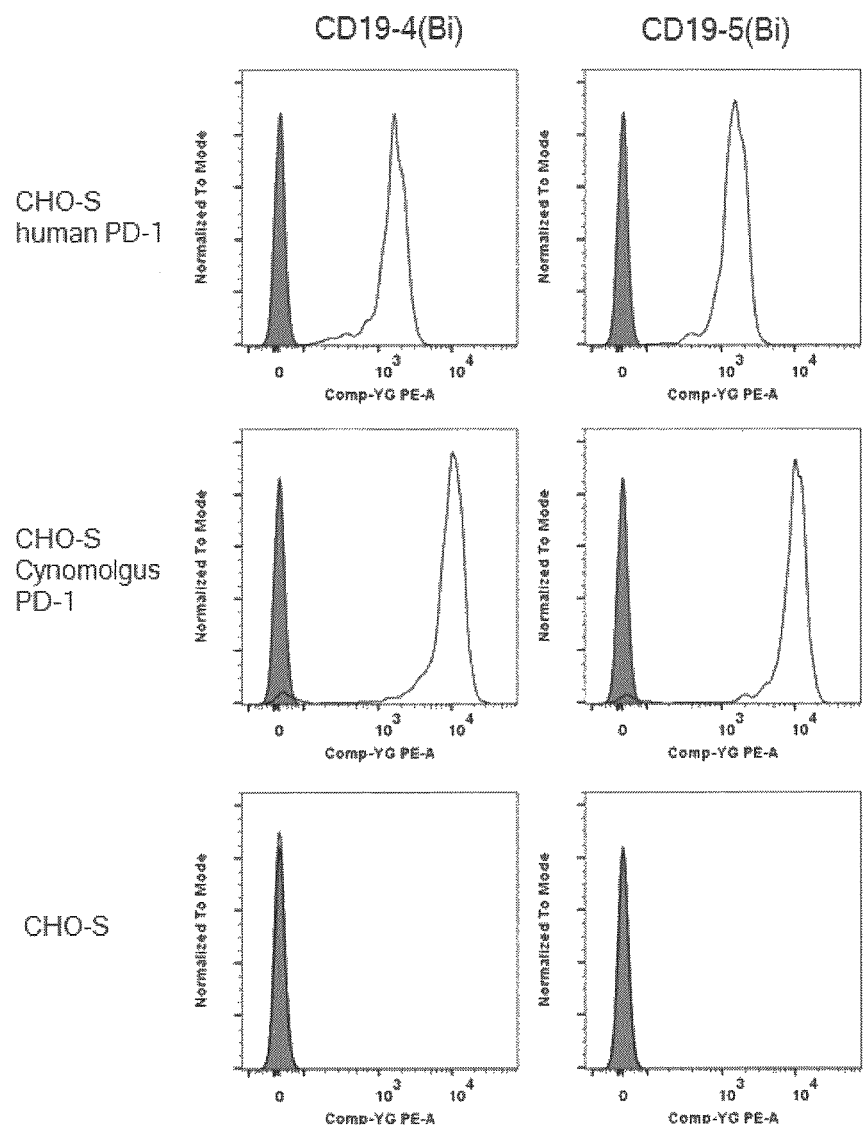

[Figure 16]
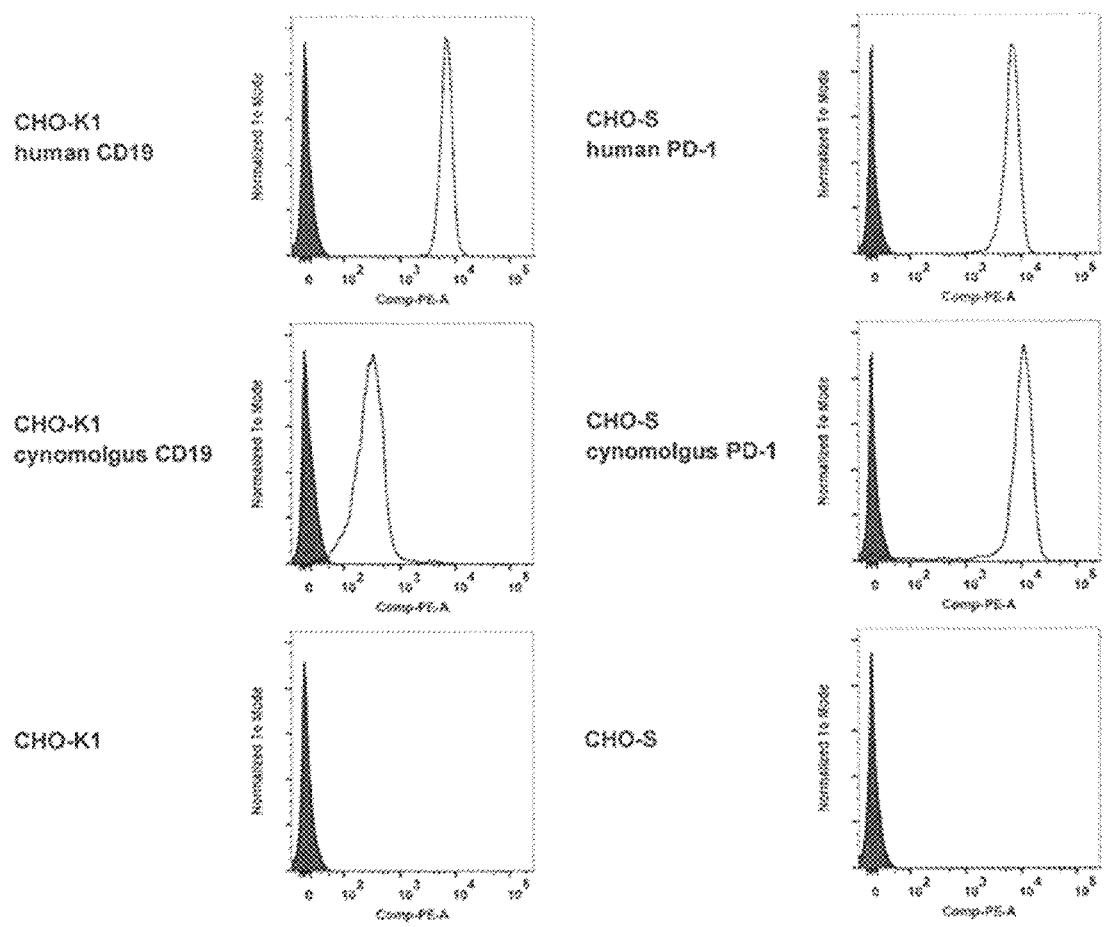

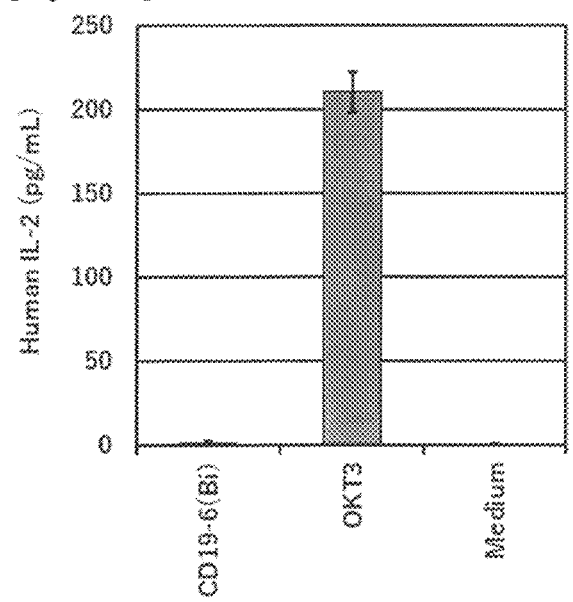
[Figure 22]

BISPECIFIC ANTIBODY

CROSS-REFERENCE TO RELATED APPLICATIONS

This application is a National Stage of International Application No. PCT/JP2020/015266 filed Apr. 3, 2020, claiming priority based on Japanese Patent Application No. 2019-071840, filed Apr. 4, 2019, and Japanese Patent Application No. 2020-022256, filed Feb. 13, 2020, the contents of all of which are incorporated herein by reference in their entirety.

TECHNICAL FIELD

The present invention relates to a bispecific antibody capable of specifically binding to PD-1 and CD19, respectively (hereinafter, may be abbreviated as a "PD-1/CD19 bispecific antibody") or an antibody fragment thereof (hereinafter, may be abbreviated as a "PD-1/CD19 bispecific antibody or the like"), and a pharmaceutical composition containing the same as an active ingredient, as well as pharmaceutical therapeutic uses thereof.

BACKGROUND ART

PD-1 is an immunosuppressive receptor belonging to an immunoglobulin family and is a molecule having a function of suppressing the immune activation signals of B-cells activated by stimulation through an antigen receptor. From analysis of PD-1 knock-out mice or the like, it is known that PD-1 signals play important roles in suppression of autoimmune diseases such as autoimmune dilated cardiomyopathy, lupus-like syndrome, autoimmune encephalomyelitis, systemic lupus erythematosus, graft-versus-host disease, type I diabetes mellitus, and rheumatoid arthritis. Accordingly, it is pointed out that a substance enhancing the PD-1 signals could be a prophylactic or therapeutic agent for autoimmune diseases.

CD19 is a membrane protein expressing on B cells and a molecular transferring stimulations into B cell along with B cell receptor complex.

There are several reports regarding PD-1 bispecific antibodies to treat autoimmune diseases so far (Patent Literatures 1 to 3), but one target of which is CD3 that is a member of T cell receptor complex.

Further, there is the report regarding a bispecific antibody targeting PD-1 and CD19 to treat tumor (Patent Literature 4), but no report about PD-1/CD19 bispecific antibodies to prevent, suppress the progression of symptoms of or the recurrence of, or treat autoimmune disease at all.

CITATION LIST

Patent Literature

Patent Literature 1: International Publication No. WO2003/011911
Patent Literature 2: International Publication No. WO2004/072286
Patent Literature 3: International Publication No. WO2013/022091
Patent Literature 4: Chinese Patent Publication No. 106939050

SUMMARY OF INVENTION

Technical Problem

The purpose of the present invention is to provide a new pharmaceutical agent for preventing, suppressing the progression of symptoms of or the recurrence of, or treating autoimmune diseases and the like.

Solution to Problem

The present inventors diligently studied and focused on the PD-1/CD19 bispecific antibody of the present invention as a substance capable of solving the above-mentioned problem, and have completed the present invention.

Furthermore, the inventors of the present invention confirmed that the PD-1/CD19 bispecific antibody has a feature of allowing the interaction between PD-1 and PD-L1 as its ligand. In addition, the inventors of the present invention found a PD-1/CD19 bispecific antibody which can be easily separated from by-products thereof in the purification process by one or more amino acid substitutions or additions to the heavy chain of the second arm specifically binding to CD19, constituting the same PD-1/CD19 bispecific antibody.

That is, the present invention relates to the followings.

[1] A bispecific antibody or an antibody fragment thereof, having the first arm specifically binding to PD-1 and the second arm specifically binding to CD19, and specifically binding to PD-1 and CD19, respectively,
wherein the first arm specifically binding to PD-1 has any one of VH selected from
(A) a heavy chain variable region (hereinafter, the "heavy chain variable region" may be abbreviated as "VH") having
(a) a complementary determining region 1 of the heavy chain variable region (hereinafter, the "complementary determining region 1 of the heavy chain variable region" may be abbreviated as "VH-CDR1") comprising the amino acid sequence set forth in SEQ ID No. 6,
(b) a complementary determining region 2 of the heavy chain variable region (hereinafter, the "complementary determining region 2 of the heavy chain variable region" may be abbreviated as "VH-CDR2") comprising the amino acid sequence set forth in SEQ ID No. 7, and
(c) a complementary determining region 3 of the heavy chain variable region (hereinafter, the "complementary determining region 3 of the heavy chain variable region" may be abbreviated as "VH-CDR3") comprising the amino acid sequence set forth in SEQ ID No. 8,
(B) a VH having
(a) a VH-CDR1 comprising the amino acid sequence set forth in SEQ ID No. 9,
(b) a VH-CDR2 comprising the amino acid sequence set forth in SEQ ID No. 10, and
(c) a VH-CDR3 comprising the amino acid sequence set forth in SEQ ID No. 11,
(C) a VH having
(a) a VH-CDR1 comprising the amino acid sequence set forth in SEQ ID No. 12, (b) a VH-CDR2 comprising the amino acid sequence set forth in SEQ ID No. 13, and
(c) a VH-CDR3 comprising the amino acid sequence set forth in SEQ ID No. 14,
(D) a VH having
(a) a VH-CDR1 comprising the amino acid sequence set forth in SEQ ID No. 15,
(b) a VH-CDR2 comprising the amino acid sequence set forth in SEQ ID No. 16, and
(c) a VH-CDR3 comprising the amino acid sequence set forth in SEQ ID No. 17, and
(E) a VH having
(a) a VH-CDR1 comprising the amino acid sequence set forth in SEQ ID No. 18,
(b) a VH-CDR2 comprising the amino acid sequence set forth in SEQ ID No. 19, and
(c) a VH-CDR3 comprising the amino acid sequence set forth in SEQ ID No. 20,
wherein the second arm specifically binding to CD19 has any one of VH selected from
(A) a VH having
(a) a VH-CDR1 comprising the amino acid sequence set forth in SEQ ID No. 35,
(b) a VH-CDR2 comprising the amino acid sequence set forth in SEQ ID No. 36, and
(c) a VH-CDR3 comprising the amino acid sequence set forth in SEQ ID No. 37,
(B) a VH having
(a) a VH-CDR1 comprising the amino acid sequence set forth in SEQ ID No. 38,
(b) a VH-CDR2 comprising the amino acid sequence set forth in SEQ ID No. 39, and
(c) a VH-CDR3 comprising the amino acid sequence set forth in SEQ ID No. 40,
(C) a VH having
(a) a VH-CDR1 comprising the amino acid sequence set forth in SEQ ID No. 41,
(b) a VH-CDR2 comprising the amino acid sequence set forth in SEQ ID No. 42, and
(c) a VH-CDR3 comprising the amino acid sequence set forth in SEQ ID No. 43,
(D) a VH having
(a) a VH-CDR1 comprising the amino acid sequence set forth in SEQ ID No. 44,
(b) a VH-CDR2 comprising the amino acid sequence set forth in SEQ ID No. 45, and
(c) a VH-CDR3 comprising the amino acid sequence set forth in SEQ ID No. 46, and
(E) a VH having
(a) a VH-CDR1 comprising the amino acid sequence set forth in SEQ ID No. 47,
(b) a VH-CDR2 comprising the amino acid sequence set forth in SEQ ID No. 48, and
(c) a VH-CDR3 comprising the amino acid sequence set forth in SEQ ID No. 49, and
wherein one to five arbitrary amino acid residues in any one or more of VH-CDRs selected from the VH-CDR1, VH-CDR2 and VH-CDR3 in the first arm specifically binding to PD-1 may be substituted with other amino acids, respectively, and/or one to five arbitrary amino acid residues in any one or more of VH-CDRs selected from the VH-CDR1, VH-CDR2 and VH-CDR3 in the second arm specifically binding to CD19 may be substituted with other amino acids, respectively.

[2] The PD-1/CD19 bispecific antibody or antibody fragment thereof according to the preceding item [1], wherein the first arm specifically binding to PD-1 has any one of VH selected from
(A) the VH having
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8,
(B) the VH having
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11,
(C) the VH having
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14,
(D) the VH having
(a) the VH-CDR1 comprising the amino acid sequence set forth in SEQ ID No. 15,
(b) the VH-CDR2 comprising the amino acid sequence set forth in SEQ ID No. 16, and
(c) the VH-CDR3 comprising the amino acid sequence set forth in SEQ ID No. 17, and
(E) the VH having
(a) the VH-CDR1 comprising the amino acid sequence set forth in SEQ ID No. 18,
(b) the VH-CDR2 comprising the amino acid sequence set forth in SEQ ID No. 19, and
(c) the VH-CDR3 comprising the amino acid sequence set forth in SEQ ID No. 20, and
wherein the second arm specifically binding to CD19 has any one of VH selected from
(A) the VH having
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37,
(B) the VH having
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40,
(C) the VH having
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43,
(D) the VH having
(a) the VH-CDR1 comprising the amino acid sequence set forth in SEQ ID No. 44,
(b) the VH-CDR2 comprising the amino acid sequence set forth in SEQ ID No. 45, and (c) the VH-CDR3 comprising the amino acid sequence set forth in SEQ ID No. 46, and
(E) the VH having
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[3] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8, and
(ii) the VH of the second arm specifically binding to CD19 is any one selected from
(A) the VH having
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37,
(B) the VH having
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40,
(C) the VH having
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43,
(D) the VH having
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46, and
(E) the VH having
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[4] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11, and
(ii) the VH of the second arm specifically binding to CD19 is any one selected from
(A) the VH having
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37,
(B) the VH having
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40,
(C) the VH having
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43,
(D) the VH having
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46, and
(E) the VH having
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[5] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD19 is any one selected from
(A) the VH having
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37,
(B) the VH having
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40,
(C) the VH having
(a) the VH-CDR1 comprising the amino acid sequence set forth in SEQ ID No. 41, (b) the VH-CDR2 comprising the amino acid sequence set forth in SEQ ID No. 42, and
(c) the VH-CDR3 comprising the amino acid sequence set forth in SEQ ID No. 43,
(D) the VH having
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46, and
(E) the VH having
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[6] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 15,
(b) the VH-CDR2 comprising the amino acid sequence set forth in SEQ ID No. 16, and
(c) the VH-CDR3 comprising the amino acid sequence set forth in SEQ ID No. 17, and
(ii) the VH of the second arm specifically binding to CD19 is any one selected from
(A) the VH having
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37,
(B) the VH having
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40,
(C) the VH having
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43,
(D) the VH having
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46, and
(E) the VH having
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[7] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 18,
(b) the VH-CDR2 comprising the amino acid sequence set forth in SEQ ID No. 19, and
(c) the VH-CDR3 comprising the amino acid sequence set forth in SEQ ID No. 20, and
(ii) the VH of the second arm specifically binding to CD19 is any one selected from
(A) the VH having
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37,
(B) the VH having
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40,
(C) the VH having
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43,
(D) the VH having
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46, and
(E) the VH having
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[8] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8, and
(ii) the VH of the second arm specifically binding to CD19 has
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37.

[9] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8, and
(ii) the VH of the second arm specifically binding to CD19 has
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40.

[10] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8, and
(ii) the VH of the second arm specifically binding to CD19 has
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43.

[11] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8, and
(ii) the VH of the second arm specifically binding to CD19 has
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46.

[12] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 6,
(b) the VH-CDR2 comprising the amino acid sequence set forth in SEQ ID No. 7, and
(c) the VH-CDR3 comprising the amino acid sequence set forth in SEQ ID No. 8, and
(ii) the VH of the second arm specifically binding to CD19 has
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[13] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11, and
(ii) the VH of the second arm specifically binding to CD19 has
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37.

[14] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11, and
(ii) the VH of the second arm specifically binding to CD19 has
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40.

[15] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11, and
(ii) the VH of the second arm specifically binding to CD19 has
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43.

[16] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 9, (b) the VH-CDR2 comprising the amino acid sequence set forth in SEQ ID No. 10, and
(c) the VH-CDR3 comprising the amino acid sequence set forth in SEQ ID No. 11, and
(ii) the VH of the second arm specifically binding to CD19 has
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46.

[17] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 9,
(b) the VH-CDR2 comprising the amino acid sequence set forth in SEQ ID No. 10, and
(c) the VH-CDR3 comprising the amino acid sequence set forth in SEQ ID No. 11, and
(ii) the VH of the second arm specifically binding to CD19 has
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[18] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD19 has
(a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37.

[19] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD19 has
(a) the VH-CDR1 comprising the amino acid sequence set forth in SEQ ID No. 38,
(b) the VH-CDR2 comprising the amino acid sequence set forth in SEQ ID No. 39, and
(c) the VH-CDR3 comprising the amino acid sequence set forth in SEQ ID No. 40.

[20] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD19 has
(a) the VH-CDR1 comprising the amino acid sequence set forth in SEQ ID No. 41,
(b) the VH-CDR2 comprising the amino acid sequence set forth in SEQ ID No. 42, and
(c) the VH-CDR3 comprising the amino acid sequence set forth in SEQ ID No. 43.

[21] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD19 has
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46.

[22] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 12,
(b) the VH-CDR2 comprising the amino acid sequence set forth in SEQ ID No. 13, and
(c) the VH-CDR3 comprising the amino acid sequence set forth in SEQ ID No. 14, and
(ii) the VH of the second arm specifically binding to CD19 has
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[23] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 15,
(b) the VH-CDR2 comprising the amino acid sequence set forth in SEQ ID No. 16, and
(c) the VH-CDR3 comprising the amino acid sequence set forth in SEQ ID No. 17, and
(ii) the VH of the second arm specifically binding to CD19 has (a) the VH-CDR1 comprising the amino acid sequence set forth in SEQ ID No. 35,
(b) the VH-CDR2 comprising the amino acid sequence set forth in SEQ ID No. 36, and
(c) the VH-CDR3 comprising the amino acid sequence set forth in SEQ ID No. 37.

[24] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 15,
  (b) the VH-CDR2 comprising the amino acid sequence set forth in SEQ ID No. 16, and
  (c) the VH-CDR3 comprising the amino acid sequence set forth in SEQ ID No. 17, and
(ii) the VH of the second arm specifically binding to CD19 has
  (a) the VH-CDR1 comprising the amino acid sequence set forth in SEQ ID No. 38,
  (b) the VH-CDR2 comprising the amino acid sequence set forth in SEQ ID No. 39, and
  (c) the VH-CDR3 comprising the amino acid sequence set forth in SEQ ID No. 40.

[25] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 15,
  (b) the VH-CDR2 comprising the amino acid sequence set forth in SEQ ID No. 16, and
  (c) the VH-CDR3 comprising the amino acid sequence set forth in SEQ ID No. 17 and
(ii) the VH of the second arm specifically binding to CD19 has
  (a) the VH-CDR1 comprising the amino acid sequence set forth in SEQ ID No. 41,
  (b) the VH-CDR2 comprising the amino acid sequence set forth in SEQ ID No. 42, and
  (c) the VH-CDR3 comprising the amino acid sequence set forth in SEQ ID No. 43.

[26] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 15,
  (b) the VH-CDR2 comprising the amino acid sequence set forth in SEQ ID No. 16, and
  (c) the VH-CDR3 comprising the amino acid sequence set forth in SEQ ID No. 17, and
(ii) the VH of the second arm specifically binding to CD19 has
  (a) the VH-CDR1 comprising the amino acid sequence set forth in SEQ ID No. 44,
  (b) the VH-CDR2 comprising the amino acid sequence set forth in SEQ ID No. 45, and
  (c) the VH-CDR3 comprising the amino acid sequence set forth in SEQ ID No. 46.

[27] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 15,
  (b) the VH-CDR2 comprising the amino acid sequence set forth in SEQ ID No. 16, and
  (c) the VH-CDR3 comprising the amino acid sequence set forth in SEQ ID No. 17, and
(ii) the VH of the second arm specifically binding to CD19 has
  (a) the VH-CDR1 comprising the amino acid sequence set forth in SEQ ID No. 47,
  (b) the VH-CDR2 comprising the amino acid sequence set forth in SEQ ID No. 48, and
  (c) the VH-CDR3 comprising the amino acid sequence set forth in SEQ ID No. 49.

[28] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 18,
  (b) the VH-CDR2 comprising the amino acid sequence set forth in SEQ ID No. 19, and
  (c) the VH-CDR3 comprising the amino acid sequence set forth in SEQ ID No. 20, and
(ii) the VH of the second arm specifically binding to CD19 has
  (a) the VH-CDR1 comprising the amino acid sequence set forth in SEQ ID No. 35,
  (b) the VH-CDR2 comprising the amino acid sequence set forth in SEQ ID No. 36, and
  (c) the VH-CDR3 comprising the amino acid sequence set forth in SEQ ID No. 37.

[29] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 18,
  (b) the VH-CDR2 comprising the amino acid sequence set forth in SEQ ID No. 19, and
  (c) the VH-CDR3 comprising the amino acid sequence set forth in SEQ ID No. 20, and
(ii) the VH of the second arm specifically binding to CD19 has
  (a) the VH-CDR1 comprising the amino acid sequence set forth in SEQ ID No. 38,
  (b) the VH-CDR2 comprising the amino acid sequence set forth in SEQ ID No. 39, and
  (c) the VH-CDR3 comprising the amino acid sequence set forth in SEQ ID No. 40.

[30] The PD-1/CD19 bispecific antibody or antibody fragment thereof according to the preceding item [1] or [2], wherein
(i) the VH of the first arm specifically binding to PD-1 has
  (a) the VH-CDR1 comprising the amino acid sequence set forth in SEQ ID No. 18,
  (b) the VH-CDR2 comprising the amino acid sequence set forth in SEQ ID No. 19, and
  (c) the VH-CDR3 comprising the amino acid sequence set forth in SEQ ID No. 20, and
(ii) the VH of the second arm specifically binding to CD19 has
  (a) the VH-CDR1 comprising the amino acid sequence set forth in SEQ ID No. 41,
  (b) the VH-CDR2 comprising the amino acid sequence set forth in SEQ ID No. 42, and
  (c) the VH-CDR3 comprising the amino acid sequence set forth in SEQ ID No. 43.

[31] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 18,
(b) the VH-CDR2 comprising the amino acid sequence set forth in SEQ ID No. 19, and
(c) the VH-CDR3 comprising the amino acid sequence set forth in SEQ ID No. 20, and
(ii) the VH of the second arm specifically binding to CD19 has
(a) the VH-CDR1 comprising the amino acid sequence set forth in SEQ ID No. 44,
(b) the VH-CDR2 comprising the amino acid sequence set forth in SEQ ID No. 45, and
(c) the VH-CDR3 comprising the amino acid sequence set forth in SEQ ID No. 46.

[32] The PD-1/CD19 bispecific antibody or antibody fragment thereof according to the preceding item [1] or [2], wherein
(i) the VH of the first arm specifically binding to PD-1 has
(a) the VH-CDR1 comprising the amino acid sequence set forth in SEQ ID No. 18,
(b) the VH-CDR2 comprising the amino acid sequence set forth in SEQ ID No. 19, and
(c) the VH-CDR3 comprising the amino acid sequence set forth in SEQ ID No. 20, and
(ii) the VH of the second arm specifically binding to CD19 has
(a) the VH-CDR1 comprising the amino acid sequence set forth in SEQ ID No. 47,
(b) the VH-CDR2 comprising the amino acid sequence set forth in SEQ ID No. 48, and
(c) the VH-CDR3 comprising the amino acid sequence set forth in SEQ ID No. 49.

[33] The PD-1/CD19 bispecific antibody or antibody fragment thereof according to any one of the preceding items [1] to [32], wherein the framework region 1 (hereinafter, may be abbreviated as "FR1"), the framework region 2 (hereinafter, may be abbreviated as "FR2") and the framework region 3 (hereinafter, may be abbreviated as "FR3") in a framework region (hereinafter, the "framework region" may be abbreviated as "FR") in the VH of the first arm specifically binding to PD-1 correspond to the amino acid sequences encoded by the germ-line V gene IGHV7-4-1 or gene thereof with somatic mutation(s), respectively.

[34] The PD-1/CD19 bispecific antibody or antibody fragment thereof according to the preceding item [33], wherein the framework region 4 (hereinafter, the "framework region 4" may be abbreviated as "FR4") in the VH of the first arm specifically binding to PD-1 comprises an amino acid sequence (excluding an amino acid sequence included in the VH-CDR3) encoded by the germ-line J gene JH6c or gene thereof with somatic mutation(s).

[35] The PD-1/CD19 bispecific antibody or antibody fragment thereof according to the preceding item [33] or [34], wherein the FR in the VH of the first arm specifically binding to PD-1 is encoded by the germ-line V gene IGHV7-4-1 which may have somatic mutation(s), and comprises the FR1 in which in the amino acid sequence set forth in SEQ ID No. 21, by the somatic mutation(s), lysine at position 13 was or may be substituted with glutamine, alanine at position 16 was or may be substituted with valine, or lysine at position 19 was or may be substituted with methionine, respectively, or which was or may be substituted with an arbitrary combination of a plurality thereof.

[36] The PD-1/CD19 bispecific antibody or antibody fragment thereof according to any one of the preceding items [33] to [35], wherein the FR in the VH of the first arm specifically binding to PD-1 is encoded by the germ-line V gene IGHV7-4-1 which may have somatic mutation(s), and comprises the FR2 in which in the amino acid sequence set forth in SEQ ID No. 21, valine at position 37 was or may be substituted with leucine.

[37] The PD-1/CD19 bispecific antibody or antibody fragment thereof according to any one of the preceding items [33] to [36], wherein the FR in the VH of the first arm specifically binding to PD-1 is encoded by the germ-line V gene IGHV7-4-1 which may have somatic mutation(s), and comprises the FR3 in which in the amino acid sequence set forth in SEQ ID No. 21, by the somatic mutation(s), serine at position 77 was or may be substituted with threonine or cysteine at position 84 was or may be substituted with serine or asparagine, respectively, or which was or may be substituted with an arbitrary combination of a plurality thereof.

[38] The PD-1/CD19 bispecific antibody or antibody fragment thereof according to any one of the preceding items [33] to [37], wherein the FR4 in the VH of the first arm specifically binding to PD-1 is encoded by the germ-line J gene JH6c which may have somatic mutation(s) (excluding the gene region encoding VH-CDR3), and wherein in the amino acid sequence (Trp-Gly-Lys-Gly-Thr-Thr*-Val-Thr-Val-Ser-Ser)(SEQ ID No. 61) of the FR4, lysine (Lys) was or may be substituted with glutamine or asparagine and/or threonine (Thr) marked with an asterisk was or may be substituted with leucine.

[39] The PD-1/CD19 bispecific antibody or antibody fragment thereof according to any one of the preceding items [1] to [38], wherein the FR1, FR2 and FR3 in the FR in the VH of the second arm specifically binding to CD19 correspond to the amino acid sequences encoded by the germ-line V gene IGHV5-51 or gene thereof with somatic mutation(s), respectively.

[40] The PD-1/CD19 bispecific antibody or antibody fragment thereof according to the preceding item [39], wherein the FR in the VH of the second arm specifically binding to CD19 is encoded by the germ-line V gene IGHV5-51 which may have somatic mutation(s), and comprises the FR1 in which in the amino acid sequence set forth in SEQ ID No. 22, by the somatic mutation(s), glutamic acid at position 1 was or may be substituted with glutamine, proline at position 14 was or may be substituted with serine, tyrosine at position 27 was or may be substituted with phenylalanine, or threonine at position 30 was or may be substituted with isoleucine, respectively, or which was or may be substituted with an arbitrary combination of a plurality thereof.

[41] The PD-1/CD19 bispecific antibody or antibody fragment thereof according to the preceding item [39] or [40], wherein the FR in the VH of the second arm specifically binding to CD19 comprises the FR2 encoded by the germ-line V gene IGHV5-51 which may have somatic mutation(s).

[42] The PD-1/CD19 bispecific antibody or antibody fragment thereof according to any one of the preceding items [39] to [41], wherein the FR in the VH of the second arm specifically binding to CD19 is encoded by the germ-line V gene IGHV5-51 which may have somatic mutation(s), and comprises the FR3 in which in the amino acid sequence set forth in SEQ ID No. 22, by the somatic mutation(s), isoleucine at position 76 was or may be substituted with phenylalanine, serine at position 77 was or may be substituted with threonine or asparagine, threonine at position 78 was or may be substituted with valine, serine at position 84 was or may be substituted with asparagine, methionine at position 93 was or may be substituted with isoleucine or leucine, or alanine at position 97 was or may be substituted with valine, respectively, or which was or may be substituted with an arbitrary combination of a plurality thereof.

[43] The PD-1/CD19 bispecific antibody or antibody fragment thereof according to any one of the preceding items [1] to [42], wherein the VH of the first arm specifically binding to PD-1 comprises the amino acid sequence set forth in any one selected from SEQ ID No. 1, SEQ ID No. 2, SEQ ID No. 3, SEQ ID No. 4 and SEQ ID No. 5, or an amino acid sequence having an identity of at least 80%, 90%, 95%, 98% or 99% to the same VH amino acid sequence.

[44] The PD-1/CD19 bispecific antibody or antibody fragment thereof according to any one of the preceding items [1] to [43], wherein the VH of the first arm specifically binding to PD-1 comprises the amino acid sequence set forth in any one selected from SEQ ID No. 1, SEQ ID No. 2, SEQ ID No. 3, SEQ ID No. 4 and SEQ ID No. 5.

[45] The PD-1/CD19 bispecific antibody or antibody fragment thereof according to any one of the preceding items [1] to [44], wherein the VH of the second arm specifically binding to CD19 comprises the amino acid sequence set forth in any one selected from SEQ ID No. 30, SEQ ID No. 31, SEQ ID No. 32, SEQ ID No. 33 and SEQ ID No. 34, or an amino acid sequence having an identity of at least 80%, 90%, 95%, 98% or 99% to the same VH amino acid sequence.

[46] The PD-1/CD19 bispecific antibody or antibody fragment thereof according to any one of the preceding items [1] to [45], wherein the VH of the second arm specifically binding to CD19 comprises the amino acid sequence in which, glutamine at position 114 in the amino acid sequence set forth in any one selected from SEQ ID No. 30, SEQ ID No. 31, SEQ ID No. 32, SEQ ID No. 33 and SEQ ID No. 34 was or may be substituted with arginine.

[47] The PD-1/CD19 bispecific antibody or antibody fragment thereof according to any one of the preceding items [1] to [45], wherein the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[48] The PD-1/CD19 bispecific antibody or antibody fragment thereof according to the preceding item [1] or [2], wherein the VH of the first arm specifically binding to PD-1 comprises the amino acid sequence set forth in any one selected from SEQ ID No. 1, SEQ ID No. 2, SEQ ID No. 3, SEQ ID No. 4 and SEQ ID No. 5, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[49] A PD-1/CD19 bispecific antibody or an antibody fragment thereof, having the first arm specifically binding to PD-1 and the second arm specifically binding to CD19, wherein the VH of the first arm specifically binding to PD-1 comprises the amino acid sequence set forth in any one selected from SEQ ID No. 1, SEQ ID No. 2, SEQ ID No. 3, SEQ ID No. 4 and SEQ ID No. 5, or an amino acid sequence having an identity of at least 80%, 90%, 95%, 98% or 99% to the same VH amino acid sequence, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, or an amino acid sequence having an identity of at least 80%, 90%, 95%, 98% or 99% to the same VH amino acid sequence.

[50] The PD-1/CD19 bispecific antibody or antibody fragment thereof according to the preceding item [1] or [2], wherein the VH of the first arm specifically binding to PD-1 comprises the amino acid sequence set forth in SEQ ID No. 1, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[51] The PD-1/CD19 bispecific antibody or antibody fragment thereof according to the preceding item [1] or [2], wherein the VH of the first arm specifically binding to PD-1 comprises the amino acid sequence set forth in SEQ ID No. 2, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[52] The PD-1/CD19 bispecific antibody or antibody fragment thereof according to the preceding item [1] or [2], wherein the VH of the first arm specifically binding to PD-1 comprises the amino acid sequence set forth in SEQ ID No. 3, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[53] The PD-1/CD19 bispecific antibody or antibody fragment thereof according to the preceding item [1] or [2], wherein the VH of the first arm specifically binding to PD-1 comprises the amino acid sequence set forth in SEQ ID No. 4, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[54] The PD-1/CD19 bispecific antibody or antibody fragment thereof according to the preceding item [1] or [2], wherein the VH of the first arm specifically binding to PD-1 comprises the amino acid sequence set forth in SEQ ID No. 5, and the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[55] The PD-1/CD19 bispecific antibody or antibody fragment thereof according to the preceding item [1], [2] or [8], wherein the VH of the first arm specifically binding to PD-1 comprises the amino acid sequence set forth in SEQ ID No. 1, and the VH of the second arm specifically binding to CD19 comprises the amino acid sequence set forth in SEQ ID No. 30 or SEQ ID No. 62.

[56] The PD-1/CD19 bispecific antibody or antibody fragment thereof according to the preceding item [1], [2] or [9], wherein the VH of the first arm specifically binding to PD-1 comprises the amino acid sequence set forth in SEQ ID

[57] The PD-1/CD19 bispecific antibody or antibody fragment thereof according to the preceding item [1], [2] or [10], wherein the VH of the first arm specifically binding to PD-1 comprises the amino acid sequence set forth in SEQ ID No. 1, and the VH of the second arm specifically binding to CD19 comprises the amino acid sequence set forth in SEQ ID No. 32 or SEQ ID No. 64.

[58] The PD-1/CD19 bispecific antibody or antibody fragment thereof according to the preceding item [1], [2] or [11], wherein the VH of the first arm specifically binding to PD-1 comprises the amino acid sequence set forth in SEQ ID No. 1, and the VH of the second arm specifically binding to CD19 comprises the amino acid sequence set forth in SEQ ID No. 33 or SEQ ID No. 65.

[59] The PD-1/CD19 bispecific antibody or antibody fragment thereof according to the preceding item [1], [2] or [12], wherein the VH of the first arm specifically binding to PD-1 comprises the amino acid sequence set forth in SEQ ID No. 1, and the VH of the second arm specifically binding to CD19 comprises the amino acid sequence set forth in SEQ ID No. 34 or SEQ ID No. 66.

[60] The PD-1/CD19 bispecific antibody or antibody fragment thereof according to the preceding item [1], [2] or [13], wherein the VH of the first arm specifically binding to PD-1 comprises the amino acid sequence set forth in SEQ ID No. 2, and the VH of the second arm specifically binding to CD19 comprises the amino acid sequence set forth in SEQ ID No. 30 or SEQ ID No. 62.

[61] The PD-1/CD19 bispecific antibody or antibody fragment thereof according to the preceding item [1], [2] or [14], wherein the VH of the first arm specifically binding to PD-1 comprises the amino acid sequence set forth in SEQ ID No. 2, and the VH of the second arm specifically binding to CD19 comprises the amino acid sequence set forth in SEQ ID No. 31 or SEQ ID No. 63.

[62] The PD-1/CD19 bispecific antibody or antibody fragment thereof according to the preceding item [1], [2] or [15], wherein the VH of the first arm specifically binding to PD-1 comprises the amino acid sequence set forth in SEQ ID No. 2, and the VH of the second arm specifically binding to CD19 comprises the amino acid sequence set forth in SEQ ID No. 32 or SEQ ID No. 64.

[63] The PD-1/CD19 bispecific antibody or antibody fragment thereof according to the preceding item [1], [2] or [16], wherein the VH of the first arm specifically binding to PD-1 comprises the amino acid sequence set forth in SEQ ID No. 2, and the VH of the second arm specifically binding to CD19 comprises the amino acid sequence set forth in SEQ ID No. 33 or SEQ ID No. 65.

[64] The PD-1/CD19 bispecific antibody or antibody fragment thereof according to the preceding item [1], [2] or [17], wherein the VH of the first arm specifically binding to PD-1 comprises the amino acid sequence set forth in SEQ ID No. 2, and the VH of the second arm specifically binding to CD19 comprises the amino acid sequence set forth in SEQ ID No. 34 or SEQ ID No. 66.

[65] The PD-1/CD19 bispecific antibody or antibody fragment thereof according to the preceding item [1], [2] or [18], wherein the VH of the first arm specifically binding to PD-1 comprises the amino acid sequence set forth in SEQ ID No. 3, and the VH of the second arm specifically binding to CD19 comprises the amino acid sequence set forth in SEQ ID No. 30 or SEQ ID No. 62.

[66] The PD-1/CD19 bispecific antibody or antibody fragment thereof according to the preceding item [1], [2] or [19], wherein the VH of the first arm specifically binding to PD-1 comprises the amino acid sequence set forth in SEQ ID No. 3, and the VH of the second arm specifically binding to CD19 comprises the amino acid sequence set forth in SEQ ID No. 31 or SEQ ID No. 63.

[67] The PD-1/CD19 bispecific antibody or antibody fragment thereof according to the preceding item [1], [2] or [20], wherein the VH of the first arm specifically binding to PD-1 comprises the amino acid sequence set forth in SEQ ID No. 3, and the VH of the second arm specifically binding to CD19 comprises the amino acid sequence set forth in SEQ ID No. 32 or SEQ ID No. 64.

[68] The PD-1/CD19 bispecific antibody or antibody fragment thereof according to the preceding item [1], [2] or [21], wherein the VH of the first arm specifically binding to PD-1 comprises the amino acid sequence set forth in SEQ ID No. 3, and the VH of the second arm specifically binding to CD19 comprises the amino acid sequence set forth in SEQ ID No. 33 or SEQ ID No. 65.

[69] The PD-1/CD19 bispecific antibody or antibody fragment thereof according to the preceding item [1], [2] or [22], wherein the VH of the first arm specifically binding to PD-1 comprises the amino acid sequence set forth in SEQ ID No. 3, and the VH of the second arm specifically binding to CD19 comprises the amino acid sequence set forth in SEQ ID No. 34 or SEQ ID No. 66.

[70] The PD-1/CD19 bispecific antibody or antibody fragment thereof according to the preceding item [1], [2] or [23], wherein the VH of the first arm specifically binding to PD-1 comprises the amino acid sequence set forth in SEQ ID No. 4, and the VH of the second arm specifically binding to CD19 comprises the amino acid sequence set forth in SEQ ID No. 30 or SEQ ID No. 62.

[71] The PD-1/CD19 bispecific antibody or antibody fragment thereof according to the preceding item [1], [2] or [24], wherein the VH of the first arm specifically binding to PD-1 comprises the amino acid sequence set forth in SEQ ID No. 4, and the VH of the second arm specifically binding to CD19 comprises the amino acid sequence set forth in SEQ ID No. 31 or SEQ ID No. 63.

[72] The PD-1/CD19 bispecific antibody or antibody fragment thereof according to the preceding item [1], [2] or [25], wherein the VH of the first arm specifically binding to PD-1 comprises the amino acid sequence set forth in SEQ ID No. 4, and the VH of the second arm specifically binding to CD19 comprises the amino acid sequence set forth in SEQ ID No. 32 or SEQ ID No. 64.

[73] The PD-1/CD19 bispecific antibody or antibody fragment thereof according to the preceding item [1], [2] or [26], wherein the VH of the first arm specifically binding to PD-1 comprises the amino acid sequence set forth in SEQ ID No. 4, and the VH of the second arm specifically binding to CD19 comprises the amino acid sequence set forth in SEQ ID No. 33 or SEQ ID No. 65.

[74] The PD-1/CD19 bispecific antibody or antibody fragment thereof according to the preceding item [1], [2] or [27], wherein the VH of the first arm specifically binding to PD-1 comprises the amino acid sequence set forth in SEQ ID No. 4, and the VH of the second arm specifically binding to CD19 comprises the amino acid sequence set forth in SEQ ID No. 34 or SEQ ID No. 66.

[75] The PD-1/CD19 bispecific antibody or antibody fragment thereof according to the preceding item [1], [2] or [28], wherein the VH of the first arm specifically binding to PD-1 comprises the amino acid sequence set forth in SEQ ID No. 5, and the VH of the second arm specifically binding to CD19 comprises the amino acid sequence set forth in SEQ ID No. 30 or SEQ ID No. 62.

[76] The PD-1/CD19 bispecific antibody or antibody fragment thereof according to the preceding item [1], [2] or [29], wherein the VH of the first arm specifically binding to PD-1 comprises the amino acid sequence set forth in SEQ ID No. 5, and the VH of the second arm specifically binding to CD19 comprises the amino acid sequence set forth in SEQ ID No. 31 or SEQ ID No. 63.

[77] The PD-1/CD19 bispecific antibody or antibody fragment thereof according to the preceding item [1], [2] or [30], wherein the VH of the first arm specifically binding to PD-1 comprises the amino acid sequence set forth in SEQ ID No. 5, and the VH of the second arm specifically binding to CD19 comprises the amino acid sequence set forth in SEQ ID No. 32 or SEQ ID No. 64.

[78] The PD-1/CD19 bispecific antibody or antibody fragment thereof according to the preceding item [1], [2] or [31], wherein the VH of the first arm specifically binding to PD-1 comprises the amino acid sequence set forth in SEQ ID No. 5, and the VH of the second arm specifically binding to CD19 comprises the amino acid sequence set forth in SEQ ID No. 33 or SEQ ID No. 65.

[79] The PD-1/CD19 bispecific antibody or antibody fragment thereof according to the preceding item [1], [2] or [32], wherein the VH of the first arm specifically binding to PD-1 comprises the amino acid sequence set forth in SEQ ID No. 5, and the VH of the second arm specifically binding to CD19 comprises the amino acid sequence set forth in SEQ ID No. 34 or SEQ ID No. 66.

[80] The PD-1/CD19 bispecific antibody or antibody fragment thereof according to any one of the preceding items [1] to [79], wherein the first arm specifically binding to PD-1 and/or the second arm specifically binding to CD19 have/has a light chain variable region (hereinafter, the "light chain variable region" may be abbreviated as "VL") having
 (a) a complementary determining region 1 of light chain variable region (hereinafter, the "complementary determining region 1 of light chain variable region" may be abbreviated as "VL-CDR1") comprising the amino acid sequence set forth in SEQ ID No. 26,
 (b) a complementary determining region 2 of light chain variable region (hereinafter, the "complementary determining region 2 of light chain variable region" may be abbreviated as "VL-CDR2") comprising the amino acid sequence set forth in SEQ ID No. 27, and
 (c) a complementary determining region 3 of light chain variable region (hereinafter, the "complementary determining region 3 of light chain variable region" may be abbreviated as "VL-CDR3") comprising the amino acid sequence set forth in SEQ ID No. 28.

[81] The PD-1/CD19 bispecific antibody or antibody fragment thereof according to any one of the preceding items [1] to [80], wherein the first arm specifically binding to PD-1 and/or the second arm specifically binding to CD19 have/has the VL comprising the amino acid sequence set forth in SEQ ID No. 25, respectively.

[82] A bispecific antibody or an antibody fragment thereof, having the first arm specifically binding to PD-1 and the second arm specifically binding to CD19, and specifically binding to PD-1 and CD19, respectively, wherein (A) the first arm specifically binding to PD-1 has a VH comprising the amino acid sequence set forth in any one selected from SEQ ID No. 1, SEQ ID No. 2, SEQ ID No. 3, SEQ ID No. 4 and SEQ ID No. 5, and a VL comprising the amino acid sequence set forth in SEQ ID No. 25, and (B) the second arm specifically binding to CD19 has a VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and a VL comprising the amino acid sequence set forth in SEQ ID No. 25.

[83] A bispecific antibody or an antibody fragment thereof, having the first arm specifically binding to PD-1 and the second arm specifically binding to CD19, and specifically binding to PD-1 and CD19, respectively, wherein the first arm specifically binding to PD-1 cross-competes for (1) the binding to PD-1 with the first arm specifically binding to PD-1 having a VH comprising the amino acid sequence set forth in any one selected from SEQ ID No. 1, SEQ ID No. 2, SEQ ID No. 3, SEQ ID No. 4 and SEQ ID No. 5, and a VL comprising the amino acid of SEQ ID No. 25, or (2) the binding to PD-1 with a variable region of a monoclonal antibody specifically binding to PD-1 comprising the same VH and VL.

[84] A bispecific antibody or an antibody fragment thereof, having the first arm specifically binding to PD-1 and the second arm specifically binding to CD19, and specifically binding to PD-1 and CD19, respectively, wherein the binding to PD-1 with the first arm specifically binding to PD-1 is cross-competed by (1) the first arm specifically binding to PD-1 having a VH comprising the amino acid sequence set forth in any one selected from SEQ ID No. 1, SEQ ID No. 2, SEQ ID No. 3, SEQ ID No. 4 and SEQ ID No. 5, and a VL comprising the amino acid of SEQ ID No. 25, or (2) a variable region of a monoclonal antibody specifically binding to PD-1 having the same VH and VL.

[85] The PD-1/CD19 bispecific antibody or antibody fragment thereof according to the preceding item [83] or [84], wherein the second arm specifically binding to CD19 further cross-competes for (1) the binding to CD19 with the second arm specifically binding to CD19 having the VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and the VL comprising the amino acid sequence set forth in SEQ ID No. 25, or (2) the binding to CD19 with the variable region of monoclonal antibody specifically binding to CD19 having the same VH and VL.

[86] The PD-1/CD19 bispecific antibody or antibody fragment thereof according to the preceding item [83] or [84], wherein the binding to CD19 with the second arm specifically binding to CD19 is further cross-competed by (1) the second arm specifically binding to CD19 having an VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and the VL comprising the amino acid of SEQ ID No. 25, or (2) a variable region of monoclonal antibody specifically binding to CD19 having the same VH and VL.

[87] The PD-1/CD19 bispecific antibody or antibody fragment thereof according to the preceding item [83] or [84], wherein the second arm specifically binding to CD19 has any one of VH selected from
 (A) the VH having
  (a) the VH-CDR1 comprising the amino acid sequence set forth in SEQ ID No. 35,
  (b) the VH-CDR2 comprising the amino acid sequence set forth in SEQ ID No. 36, and (c) the VH-CDR3 comprising the amino acid sequence set forth in SEQ ID No. 37,
(B) the VH having
   (a) the VH-CDR1 comprising the amino acid sequence set forth in SEQ ID No. 38,
   (b) the VH-CDR2 comprising the amino acid sequence set forth in SEQ ID No. 39, and
   (c) the VH-CDR3 comprising the amino acid sequence set forth in SEQ ID No. 40,
(C) the VH having
   (a) the VH-CDR1 comprising the amino acid sequence set forth in SEQ ID No. 41,
   (b) the VH-CDR2 comprising the amino acid sequence set forth in SEQ ID No. 42, and
   (c) the VH-CDR3 comprising the amino acid sequence set forth in SEQ ID No. 43,
(D) the VH having,
   (a) the VH-CDR1 comprising the amino acid sequence set forth in SEQ ID No. 44,
   (b) the VH-CDR2 comprising the amino acid sequence set forth in SEQ ID No. 45, and
   (c) the VH-CDR3 comprising the amino acid sequence set forth in SEQ ID No. 46, and
(E) the VH having
   (a) the VH-CDR1 comprising the amino acid sequence set forth in SEQ ID No. 47,
   (b) the VH-CDR2 comprising the amino acid sequence set forth in SEQ ID No. 48, and
   (c) the VH-CDR3 comprising the amino acid sequence set forth in SEQ ID No. 49.

[88] The PD-1/CD19 bispecific antibody or antibody fragment thereof according to the preceding item [83] or [84], wherein the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, or an amino acid sequence having an identity of at least 80%, 90%, 95%, 98% or 99% to the same VH amino acid sequence.

[89] The PD-1/CD19 bispecific antibody or antibody fragment thereof according to the preceding item [83] or [84], wherein the VH of the second arm specifically binding to CD19 comprises the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66.

[90] The PD-1/CD19 bispecific antibody or antibody fragment thereof according to any one of the preceding items [83] to [89], wherein the first arm specifically binding to PD-1 and/or the second arm specifically binding to CD19 have/has the VL having
   (a) the VL-CDR1 comprising the amino acid sequence set forth in SEQ ID No. 26,
   (b) the VL-CDR2 comprising the amino acid sequence set forth in SEQ ID No. 27, and
   (c) the VL-CDR3 comprising the amino acid sequence set forth in SEQ ID No. 28.

[91] The PD-1/CD19 bispecific antibody or antibody fragment thereof according to any one of the preceding items [83] to [89], wherein the first arm specifically binding to PD-1 and/or the second arm specifically binding to CD19 have/has the VL comprising the amino acid sequence set forth in SEQ ID No. 25.

[92] The PD-1/CD19 bispecific antibody or antibody fragment thereof according to any one of the preceding items [1] to [91], wherein the PD-1/CD19 bispecific antibody is an IgG antibody.

[93] The PD-1/CD19 bispecific antibody or antibody fragment thereof according to the preceding item [92], wherein the IgG antibody in the preceding item [92] is an $IgG_1$ or $IgG_4$ antibody.

[94] The PD-1/CD19 bispecific antibody or antibody fragment thereof according to the preceding item [92], wherein the IgG antibody in the preceding item [92] is an $IgG_1$ antibody.

[95] The PD-1/CD19 bispecific antibody or antibody fragment thereof according to the preceding item [92], wherein the IgG antibody in the preceding item [92] is an $IgG_4$ antibody.

[96] The PD-1/CD19 bispecific antibody or antibody fragment thereof according to the preceding item [94], wherein in two heavy chain constant regions of the $IgG_1$ antibody in the preceding item [94], leucine at position 235 according to the EU numbering system was substituted with glycine, respectively, and/or glycine at position 236 according to the EU numbering system was substituted with arginine, respectively.

[97] The PD-1/CD19 bispecific antibody or antibody fragment thereof according to the preceding item [94] or [96], wherein in a constant region of heavy chain having the VH of the first arm specifically binding to PD-1, both of leucine at position 351 and threonine at position 366 according to the EU numbering system were substituted with lysine, and in a constant region of heavy chain having the VH of the second arm specifically binding to CD19, leucine at position 351 was substituted with aspartic acid and leucine at position 368 was substituted with glutamic acid.

[98] The PD-1/CD19 bispecific antibody or antibody fragment thereof according to the preceding item [94] or [96], wherein in a constant region of heavy chain having the VH of the first arm specifically binding to PD-1, leucine at position 351 according to the EU numbering system was substituted with aspartic acid and leucine at position 368 was substituted with glutamic acid, and in a constant region of heavy chain having the VH of the second arm specifically binding to CD19, both of leucine at position 351 and threonine at position 366 were substituted with lysine.

[99] The PD-1/CD19 bispecific antibody or antibody fragment thereof according to any one of the preceding items [94] and [96] to [98], wherein in two heavy chain constant regions of the $IgG_1$ antibody in any one of the preceding items [94] and [96] to [98], lysine at position 447 according to the EU numbering system was deleted, respectively.

[100] The PD-1/CD19 bispecific antibody or antibody fragment thereof according to the preceding item [95], wherein in two heavy chain constant regions of the $IgG_4$ antibody in the preceding item [95], serine at position 228 according to the EU numbering system was substituted with proline, respectively.

[101] The PD-1/CD19 bispecific antibody or antibody fragment thereof according to any one of the preceding items [94] and [96] to [99], wherein the heavy chain having the VH of the second arm specifically binding to CD19 further has Gly (glycine), Gly-Lys-Lys-Ala (SEQ ID No. 67), Gly-Lys-Ala-Lys-Ala (SEQ ID No. 68), Gly-Arg-Arg-Ala (SEQ ID No. 69) or Gly-Arg-Ala-Arg-Ala (SEQ ID No. 70) at its C-terminus.

[102] The PD-1/CD19 bispecific antibody or antibody fragment thereof according to any one of the preceding items [1] to [94], [96], [98], [99] and [101], wherein the heavy chain having the VH of the first arm specifically binding to PD-1 has the heavy chain constant region comprising the amino acid sequence set forth in SEQ ID No. 23.

[103] The PD-1/CD19 bispecific antibody or antibody fragment thereof according to any one of the preceding items [1] to [94], [96], [98], [99], [101] and [102], wherein the heavy chain having the VH of the second arm specifically binding to CD19 has the heavy chain constant region comprising the amino acid sequence set forth in any one selected from SEQ ID No. 24, SEQ ID No. 71, SEQ ID No. 72, SEQ ID No. 73, SEQ ID No. 74 and SEQ ID No. 75.

[104] The PD-1/CD19 bispecific antibody or antibody fragment thereof according to any one of the preceding items [1] to [103], wherein the light chain having the VL of the first arm specifically binding to PD-1 and/or the light chain having the VL of the second arm specifically binding to CD19 contain(s) a light chain constant region comprising the amino acid sequence set forth in SEQ ID No. 29.

[105] A bispecific antibody or an antibody fragment thereof, having the first arm specifically binding to PD-1 and the second arm specifically binding to CD19, and specifically binding to PD-1 and CD19, respectively, wherein
(A) a heavy chain having a VH of the first arm specifically binding to PD-1 has a VH comprising the amino acid sequence set forth in any one selected from SEQ ID No. 1, SEQ ID No. 2, SEQ ID No. 3, SEQ ID No. 4 and SEQ ID No. 5, and the heavy chain constant region comprising the amino acid sequence set forth in SEQ ID No. 23,
(B) a light chain having a VL of the first arm specifically binding to PD-1 has a VL comprising the amino acid sequence set forth in SEQ ID No. 25, and the light chain constant region comprising the amino acid sequence set forth in SEQ ID No. 29,
(C) a heavy chain having a VH of the second arm specifically binding to CD19 has a VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and the heavy chain constant region comprising the amino acid sequence set forth in SEQ ID No. 24, and
(D) a light chain having a VL of the second arm specifically binding to CD19 has a VL comprising the amino acid sequence set forth in SEQ ID No. 25, and the light chain constant region comprising the amino acid sequence set forth in SEQ ID No. 29.

[106] The PD-1/CD19 bispecific antibody or antibody fragment thereof according to any one of the preceding items [1] to [105], wherein the first arm specifically binding to PD-1 allows the interaction between PD-1 and PD-L1.

[107] The PD-1/CD19 bispecific antibody or antibody fragment thereof according to any one of the preceding items [1] to [106], wherein a complex consisting of the heavy chain and light chain of the first arm specifically binding to PD-1 has an isoelectric point between about 7.4 and about 7.7 (preferably, between about 7.5 and about 7.6).

[108] The PD-1/CD19 bispecific antibody or antibody fragment thereof according to any one of the preceding items [1] to [107], wherein a complex consisting of the heavy chain and light chain of the second arm specifically binding to CD19 has an isoelectric point between about 8.3 and about 8.8 (preferably, between about 8.4 and about 8.6).

[∩] The PD-1/CD19 bispecific antibody or antibody fragment thereof according to any one of the preceding items [1] to [108], wherein cytokine production in blood or tissue is sufficiently reduced during administration or within 24 hours after administration.

[110] The PD-1/CD19 bispecific antibody or antibody fragment thereof according to any one of the preceding items [1] to [108], wherein the first arm specifically binding to PD-1 allows the interaction between PD-1 and PD-L1, and wherein cytokine production is sufficiently reduced.

[111] The PD-1/CD19 bispecific antibody or antibody fragment thereof according to the preceding item [109] or [110], wherein the cytokine is at least IL-2, IFN-γ or TNF-α.

[112] The PD-1/CD19 bispecific antibody or antibody fragment thereof according to any one of the preceding items [1] to [111], which suppresses B-cell activation by binding to PD-1 and CD19 expressed on the same B cell, respectively.

[113] The PD-1/CD19 bispecific antibody or antibody fragment thereof according to any one of the preceding items [1] to [111], which suppresses activation of T-cell (preferably, memory T-cell).

[114] The PD-1/CD19 bispecific antibody or antibody fragment thereof according to the preceding item [113], which suppresses T-cell activation by binding to CD19 expressed on B cell and PD-1 expressed on T cell, respectively.

[115] The PD-1/CD19 bispecific antibody or antibody fragment thereof according to any one of the preceding items [1] to [114], wherein PD-1 is human PD-1, and CD19 is human CD19, respectively.

[116] The PD-1/CD19 bispecific antibody or antibody fragment thereof according to any one of the preceding items [1] to [115], wherein the PD-1/CD19 bispecific antibody is a monoclonal antibody.

[117] The PD-1/CD19 bispecific antibody or antibody fragment thereof according to any one of the preceding items [1] to [116], wherein the PD-1/CD19 bispecific antibody is an isolated antibody.

[1-1] A pharmaceutical composition containing the PD-1/CD19 bispecific antibody or antibody fragment thereof of any one selected from the preceding items [1] to [117], as an active ingredient.

[1-2] The pharmaceutical composition according to the preceding item [1-1], further containing at least a pharmaceutically acceptable carrier.

[2-1] An agent for preventing, suppressing the progression of symptoms of, suppressing the recurrence of, and/or treating autoimmune disease, containing the PD-1/CD19 bispecific antibody or antibody fragment thereof of any one selected from the preceding items [1] to [117] as an active ingredient.

[2-2] The agent according to the preceding item [2-1], wherein autoimmune disease is Behcet's disease, systemic lupus erythematosus, chronic discoid lupus erythematosus, multiple sclerosis (systemic scleroderma and progressive systemic sclerosis), scleroderma, polymyositis, dermatomyositis, periarteritis nodosa (polyarteritis nodosa and microscopic polyangiitis), aortitis syndrome (Takayasu's arteritis), malignant rheumatoid arthritis, rheumatoid arthritis, juvenile idiopathic arthritis, spondyloarthritis, mixed connective tissue disease, Sjogren's syndrome, adult Still's disease, vasculitis, allergic granulomatous vasculitis, hypersensitivity vasculitis, rheumatoid vasculitis, large vessel vasculitis, ANCA associated vasculitis (e.g., granulomatosis with polyangiitis and eosinophilic granulomatosis with polyangiitis), Cogan's syndrome, RS3PE syndrome, temporal arteritis, polymyalgia rheumatica, fibromyalgia, antiphospholipid antibody syndrome, eosinophilic fasciitis, IgG₄-related disease (e.g., primary sclerosing cholangitis and autoimmune insulitis, etc.), Guillain-Barre syndrome, myasthenia gravis, chronic atrophic gastritis, autoimmune hepatitis, non-alcoholic steatohepatitis, primary biliary cirrhosis, Goodpasture's syndrome, rapidly progressive glomerulonephritis, megaloblastic anemia, autoimmune hemolytic anemia, pernicious anemia, autoimmune neutropenia, idiopathic thrombocytopenic purpura, Basedow disease (Graves' disease (hyperthyroidism)), Hashimoto disease, autoimmune adrenal insufficiency, primary hypothyroidism, Addison's disease (chronic hypoadrenocorticism), idiopathic Addison's disease, type I diabetes mellitus, slowly progressive type I diabetes mellitus (latent autoimmune diabetes in adult), focal scleroderma, psoriasis, psoriatic arthritis, bullous pemphigoid, pemphigus, pemphigoid, gestational herpes, linear IgA bullous dermatosis, acquired epidermolysis bullosa, alopecia areata, vitiligo, vitiligo vulgaris, neuromyelitis optica, chronic inflammatory demyelinating polyneuropathy, multifocal motor neuropathy, sarcoidosis, giant cell arteritis, amyotrophic lateral sclerosis, Harada disease, autoimmune optic neuropathy, idiopathic azoospermia, habitual abortion, inflammatory bowel disease (e.g., ulcerative colitis and Crohn's disease), celiac disease, ankylosing spondylitis, severe asthma, chronic urticaria, transplantation immunity, familial mediterranean fever, eosinophilic chronic rhinosinusitis, dilated cardiomyopathy, systemic mastocytosis, or inclusion body myositis.

[2-3] An agent for preventing, suppressing the progression of symptoms of, suppressing the recurrence of, and/or treating graft-versus-host disease (GVHD), containing the PD-1/CD19 bispecific antibody or antibody fragment thereof according to any one of the preceding items [1] to [117] as an active ingredient.

[2-4] An agent for preventing, suppressing the progression of symptoms of, suppressing the recurrence of, and/or treating type I diabetes mellitus, containing the PD-1/CD19 bispecific antibody or antibody fragment thereof of any one selected from the preceding items [1] to [117] as an active ingredient, and being administered along with any one or more drugs selected from an insulin formulation (e.g., human insulin, insulin glargine, insulin lispro, insulin detemir and insulin aspart, etc.), sulfonylurea agent (e.g., glibenclamide, gliclazide and glimepiride, etc.), quick-acting insulin secretion promoter (e.g., nateglinide etc.), biguanide preparation (e.g., metformin etc.), insulin resistance improving agent (e.g., pioglitazone etc.), α-glucosidase inhibitor (e.g., acarbose and voglibose, etc.), diabetic neuropathy therapeutic agent (e.g., epalrestat, mexiletine and imidapril, etc.), GLP-1 analog preparation (e.g., liraglutide, exenatide and lixisenatide, etc.) and DPP-4 inhibitor (e.g., sitagliptin, vildagliptin and alogliptin, etc.).

[2-5] An agent for preventing, suppressing the progression of symptoms of, suppressing the recurrence of, and/or treating multiple sclerosis, containing the PD-1/CD19 bispecific antibody or antibody fragment thereof of any one selected from the preceding items [1] to [117] as an active ingredient, and being administered along with any one or more drugs selected from a steroid agent (e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamsinolone, triamsinolone acetate, triamsinolone acetonide, dexamethasone, dexamethasone acetate, dexamethasone sodium phosphate, dexamethasone palmitate, paramethasone acetate and betamethasone, etc.), interferon β-1a, interferon β-1b, glatiramer acetate, mitoxantrone, azathioprine, cyclophosphamide, cyclosporin, methotrexate, cladribine, adrenocorticotropic hormone (ACTH), corticotropin, mizoribine, tacrolimus, fingolimod, and alemtuzumab.

[2-6] An agent for preventing, suppressing the progression of symptoms of, suppressing the recurrence of, and/or treating systemic lupus erythematosus, containing the PD-1/CD19 bispecific antibody or antibody fragment thereof of any one selected from the preceding items [1] to [117] as an active ingredient, and being administered along with any one or more selected from a steroid agent (e.g., the steroid agents mentioned in the preceding item [2-5]), immunosuppressive agent (e.g., cyclosporin, tacrolimus and fingolimod, etc.) and belimumab.

[2-7] An agent for preventing, suppressing the progression of symptoms of, suppressing the recurrence of, and/or treating rheumatoid arthritis, containing the PD-1/CD19 bispecific antibody or antibody fragment thereof of any one selected from the preceding items [1] to [117] as an active ingredient, and being administered along with any one or more drugs selected from a steroid agent (e.g., the steroid agents mentioned in the preceding item [2-5]), anti-rheumatic agent (e.g., methotrexate, sulfasalazine, bucillamine, leflunomide, mizoribine and tacrolimus, etc.), anti-cytokine agent (e.g., infliximab, adalimumab, tocilizumab, etanercept, golimumab and certolizumab, etc.) and abatacept.

[2-8] An agent for preventing, suppressing the progression of symptoms of, suppressing the recurrence of, and/or treating autoimmune disease, containing the PD-1/CD19 bispecific antibody or antibody fragment thereof of any one selected from the preceding items [1] to [117] as an active ingredient, and being administered along with any one or more of agents listed in the preceding items [2-4] to [2-7].

[2-9] The agent for preventing, suppressing the progression of symptoms of, suppressing the recurrence of, and/or treating diseases according to the preceding items [2-4] to [2-8], being administered to the patient to which any one or more of drugs listed in the preceding items [2-4] to [2-7] is/are administered.

[2-10] The agent for preventing, suppressing the progression of symptoms of, suppressing the recurrence of, and/or treating diseases according to the preceding items [2-4] to [2-8], being administered after administration of any one or more of drugs listed in the preceding items [2-4] to [2-7].

[2-11] The agent for preventing, suppressing the progression of symptoms of, suppressing the recurrence of, and/or treating diseases according to the preceding items [2-4] to [2-8], being administered prior to administration of any one or more of drugs listed in the preceding items [2-4] to [2-7].

[3-1] An intravenous injection formulation containing the PD-1/CD19 bispecific antibody or antibody fragment thereof according to any one of the preceding items [1] to [117] and at least a pharmaceutically acceptable carrier.

[3-2] The intravenous injection formulation according to the preceding item [3-1] for use in preventing, suppressing the progression of symptoms of, suppressing the recurrence of, and/or treating autoimmune disease.

[3-3] The intravenous injection formulation according to the preceding item [3-1] or [3-2] for use in drip infusion.

[4-1] An isolated polynucleotide or a fragment thereof, encoding a heavy chain having a VH of the second arm specifically binding to CD19 constituting the PD-1/CD19 bispecific antibody of any one selected from the preceding items [1] to [117].

[4-2] An isolated polynucleotide or a fragment thereof, encoding a VH of the second arm specifically binding to CD19 constituting the PD-1/CD19 bispecific antibody of any one selected from the preceding items [1] to [117].

[4-3] The isolated polynucleotide or fragment thereof according to the preceding item [4-1] or [4-2], wherein the VH of the second arm specifically binding to CD19 is encoded by a polynucleotide comprising the base sequence set forth in any one selected from SEQ ID Nos. 56 to 60 and SEQ ID Nos. 76 to 80.

[4-4] An isolated polynucleotide or a fragment thereof, containing a polynucleotide comprising the base sequence set forth in any one selected from SEQ ID Nos. 56 to 60 and SEQ ID Nos. 76 to 80.

[5-1] An expression vector having a polynucleotide of any one of the preceding items [4-1] to [4-4].

[6-1] An animal cell, into which the expression vector of the preceding item [5-1] is transfected, or which was transformed by the same vector.

[7-1] A method for preventing, suppressing the progression of symptoms of, suppressing the recurrence of, and/or treating autoimmune disease, comprising administering to a patient an effective amount of the PD-1/CD19 bispecific antibody or antibody fragment thereof of any one selected from the preceding items [1] to [117].

[8-1] A PD-1/CD19 bispecific antibody or an antibody fragment thereof of any one selected from the preceding items [1] to [117] for use in preventing, suppressing the progression of symptoms of, suppressing the recurrence of, and/or treating autoimmune disease.

[9-1] Use of the PD-1/CD19 bispecific antibody or antibody fragment thereof of any one selected from the preceding items [1] to [117] for manufacturing a drug for preventing, suppressing the progression of symptoms of, suppressing the recurrence of, and/or treating autoimmune disease.

[10-1] An isolated anti-CD19 monoclonal antibody or an antibody fragment thereof, which cross-competes for binding to CD19 with an antibody specifically binding to CD19 having a VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and a VL comprising the amino acid sequence set forth in SEQ ID No. 25.

[10-2] An isolated anti-CD19 monoclonal antibody or an antibody fragment thereof, wherein the binding to CD19 with the antibody or antibody fragment thereof is cross-competed by an antibody specifically binding to CD19 having a VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and a VL comprising the amino acid sequence set forth in SEQ ID No. 25.

[10-3] An isolated anti-CD19 monoclonal antibody or an antibody fragment thereof, having any one of VH selected from
  (A) a VH having
    (a) a VH-CDR1 comprising the amino acid sequence set forth in SEQ ID No. 35,
    (b) a VH-CDR2 comprising the amino acid sequence set forth in SEQ ID No. 36, and
    (c) a VH-CDR3 comprising the amino acid sequence set forth in SEQ ID No. 37,
  (B) a VH having
    (a) a VH-CDR1 comprising the amino acid sequence set forth in SEQ ID No. 38,
    (b) a VH-CDR2 comprising the amino acid sequence set forth in SEQ ID No. 39, and
    (c) a VH-CDR3 comprising the amino acid sequence set forth in SEQ ID No. 40,
  (C) a VH having
    (a) a VH-CDR1 comprising the amino acid sequence set forth in SEQ ID No. 41,
    (b) a VH-CDR2 comprising the amino acid sequence set forth in SEQ ID No. 42, and
    (c) a VH-CDR3 comprising the amino acid sequence set forth in SEQ ID No. 43,
  (D) a VH having
    (a) a VH-CDR1 comprising the amino acid sequence set forth in SEQ ID No. 44,
    (b) a VH-CDR2 comprising the amino acid sequence set forth in SEQ ID No. 45, and
    (c) a VH-CDR3 comprising the amino acid sequence set forth in SEQ ID No. 46, and
  (E) a VH having
    (a) a VH-CDR1 comprising the amino acid sequence set forth in SEQ ID No. 47,
    (b) a VH-CDR2 comprising the amino acid sequence set forth in SEQ ID No. 48, and
    (c) a VH-CDR3 comprising the amino acid sequence set forth in SEQ ID No. 49, and
  a VL having
    (a) a VL-CDR1 comprising the amino acid sequence set forth in SEQ ID No. 26,
    (b) a VL-CDR2 comprising the amino acid sequence set forth in SEQ ID No. 27, and
    (c) a VL-CDR3 comprising the amino acid sequence set forth in SEQ ID No. 28.

[10-4] An isolated anti-CD19 monoclonal antibody or an antibody fragment thereof, having any one of VH selected from
  (A) a VH having
    (a) a VH-CDR1 comprising the amino acid sequence set forth in SEQ ID No. 35,
    (b) a VH-CDR2 comprising the amino acid sequence set forth in SEQ ID No. 36, and
    (c) a VH-CDR3 comprising the amino acid sequence set forth in SEQ ID No. 37,
  (B) a VH having
    (a) a VH-CDR1 comprising the amino acid sequence set forth in SEQ ID No. 38,
    (b) a VH-CDR2 comprising the amino acid sequence set forth in SEQ ID No. 39, and
    (c) a VH-CDR3 comprising the amino acid sequence set forth in SEQ ID No. 40,
  (C) a VH having
    (a) a VH-CDR1 comprising the amino acid sequence set forth in SEQ ID No. 41,
    (b) a VH-CDR2 comprising the amino acid sequence set forth in SEQ ID No. 42, and
    (c) a VH-CDR3 comprising the amino acid sequence set forth in SEQ ID No. 43,
  (D) a VH having
    (a) a VH-CDR1 comprising the amino acid sequence set forth in SEQ ID No. 44,
    (b) a VH-CDR2 comprising the amino acid sequence set forth in SEQ ID No. 45, and
    (c) a VH-CDR3 comprising the amino acid sequence set forth in SEQ ID No. 46, and (E) a VH having
  (a) a VH-CDR1 comprising the amino acid sequence set forth in SEQ ID No. 47,
  (b) a VH-CDR2 comprising the amino acid sequence set forth in SEQ ID No. 48, and
  (c) a VH-CDR3 comprising the amino acid sequence set forth in SEQ ID No. 49, and
a VL having
  (a) a VL-CDR1 comprising the amino acid sequence set forth in SEQ ID No. 26,
  (b) a VL-CDR2 comprising the amino acid sequence set forth in SEQ ID No. 27, and
  (c) a VL-CDR3 comprising the amino acid sequence set forth in SEQ ID No. 28,
wherein one to five arbitrary amino acid residues in any one or more of the CDRs selected from the VH-CDR1, VH-CDR2 and VH-CDR3 in the VH may be substituted with other amino acids.

[10-5] The isolated anti-CD19 monoclonal antibody or antibody fragment thereof according to any one of the preceding items [10-1] to [10-4], having the VH comprising the amino acid sequence set forth in any one selected from SEQ ID No. 30, SEQ ID No. 31, SEQ ID No. 32, SEQ ID No. 33 and SEQ ID No. 34, or a VH comprising the amino acid sequence having at least 80%, 90%, 95%, 98% or 99% identity of the same VH amino acid sequence, and the VL comprising the amino acid sequence set forth in SEQ ID No. 25.

[10-6] The isolated anti-CD19 monoclonal antibody or antibody fragment thereof according to any one of the preceding items [10-1] to [10-4], having the VH comprising the amino acid sequence in which glutamine at position 114 in the amino acid sequence set forth in any one selected from SEQ ID No. 30, SEQ ID No. 31, SEQ ID No. 32, SEQ ID No. 33 and SEQ ID No. 34 was or may be substituted with arginine, and the VL comprising the amino acid sequence set forth in SEQ ID No. 25.

[10-7] The isolated anti-CD19 monoclonal antibody or antibody fragment thereof according to any one of the preceding items [10-1] to [10-4], having the VH comprising the amino acid sequence set forth in any one selected from SEQ ID No. 30, SEQ ID No. 31, SEQ ID No. 32, SEQ ID No. 33, SEQ ID No. 34, SEQ ID No. 62, SEQ ID No. 63, SEQ ID No. 64, SEQ ID No. 65 and SEQ ID No. 66, and the VL comprising the amino acid sequence set forth in SEQ ID No. 25.

[10-8] The isolated anti-CD19 monoclonal antibody or antibody fragment thereof according to any one of the preceding items [10-1] to [10-7], wherein CD19 is human CD19.

[10-9] The isolated anti-CD19 monoclonal antibody or antibody fragment thereof according to any one of the preceding items [10-1] to [10-8], wherein the anti-CD19 antibody is an IgG antibody.

[10-10] The isolated anti-CD19 monoclonal antibody or antibody fragment thereof according to the preceding item [10-9], wherein the IgG antibody described in the preceding item [10-9] is an $IgG_1$ antibody or $IgG_4$ antibody.

[10-11] The isolated anti-CD19 monoclonal antibody or antibody fragment thereof according to the preceding item [10-9], wherein the IgG antibody described in the preceding item [10-9] is an $IgG_1$ antibody.

[10-12] The isolated anti-CD19 monoclonal antibody or antibody fragment thereof according to the preceding item [10-9], wherein the IgG antibody described in the preceding item [10-9] is an $IgG_4$ antibody.

[10-13] The isolated anti-CD19 monoclonal antibody or antibody fragment thereof according to any one of the preceding items [10-1] to [10-11], wherein in the constant region of heavy chain, (1) leucine at position 351 was substituted with aspartic acid and leucine at position 368 was substituted with glutamic acid or (2) both of leucine at position 351 and threonine at position 366 in the constant region of heavy chain were substituted with lysine.

[10-14] The isolated anti-CD19 monoclonal antibody or antibody fragment thereof according to any one of the preceding items [10-1] to [10-13], further having Gly (glycine), Gly-Lys-Lys-Ala (SEQ ID No. 67), Gly-Lys-Ala-Lys-Ala (SEQ ID No. 68), Gly-Arg-Arg-Ala (SEQ ID No. 69) or Gly-Arg-Ala-Arg-Ala (SEQ ID No. 70) at the C-terminus of the heavy chain.

[10-15] The isolated anti-CD19 monoclonal antibody or antibody fragment thereof according to any one of the preceding items [10-1] to [10-14], wherein the heavy chains have the heavy chain constant regions comprising the amino acid sequence set forth in any one selected from SEQ ID No. 24, SEQ ID No. 71, SEQ ID No. 72, SEQ ID No. 73, SEQ ID No. 74 and SEQ ID No. 75.

[11-1] An agent for preventing, suppressing the progression of symptoms of, suppressing the recurrence of, and/or treating autoreactive B cell-mediated disease, containing the PD-1/CD19 bispecific antibody or antibody fragment thereof of any one selected from the preceding items [1] to [117] as an active ingredient.

[11-2] The agent for preventing, suppressing the progression of symptoms of, suppressing the recurrence of, and/or treating autoreactive B cell-mediated disease according to the preceding item [11-1], wherein autoreactive B cell-mediated disease is systemic lupus erythematodes, Graves' disease, myasthenia gravis, autoimmune hemolytic anemia, autoimmune thrombocytopenia, asthma, cryoglobulinemia, primary sclerosing cholangitis or malignant anemia.

[12-1] An agent for suppressing autoreactive B cells, containing the PD-1/CD19 bispecific antibody or antibody fragment thereof of any one selected from the preceding items [1] to [117] as an active ingredient.

[12-2] The agent for suppressing autoreactive B cells according to the preceding item [12-1], wherein the suppression of autoreactive B cells is that of immunoglobulin production.

[12-3] The agent for suppressing autoreactive B cells according to the preceding item [12-2], wherein the immunoglobulin is IgG or IgM.

[13-1] An agent for suppressing T-cell activation, containing the PD-1/CD19 bispecific antibody or antibody fragment thereof of any one selected from the preceding items [1] to [117] as an active ingredient.

[13-2] The agent for suppressing T-cell activation according to the preceding item [13-1], wherein the suppression of T-cell activation is that of cytokine production.

[13-3] The agent for suppressing T-cell activation according to the preceding item [13-1] or [13-2], wherein the suppression of T-cell activation is that of memory T-cell activation.

[14-1] A method for suppressing autoreactive B cells or T-cells activation, comprising administering to a patient an effective amount of the PD-1/CD19 bispecific antibody or antibody fragment thereof of any one selected from the preceding items [1] to [117].

[15-1] The PD-1/CD19 bispecific antibody or antibody fragment thereof of any one selected from the preceding items [1] to [117] for use in suppressing autoreactive B cells or T-cell activation.

[16-1] Use of the PD-1/CD19 bispecific antibody or antibody fragment thereof of any one selected from the preceding items [1] to [117] for manufacturing an agent for suppressing autoreactive B cells or T-cell activation.

Advantage Effects of Invention

The PD-1/CD19 bispecific antibody of the present invention allows the interaction between PD-1 and PD-L1, and is expected to enhance or sustain the effect on the prevention of, suppression of the progression of symptoms of, suppression of the recurrence of, and/or therapy for autoimmune disease.

BRIEF DESCRIPTION OF THE DRAWINGS

FIG. 1 It shows the amino acid sequences of the VL and constant region of common light chain.

FIG. 2 It shows the amino acid sequences of the respective CDRs in the VL of common light chain.

FIG. 3 It shows the amino acid sequences encoded by germ-line V genes: IGHV7-4-1 and IGHV5-51, respectively.

FIG. 4 It shows a sequence alignment among the VH of the respective clones of the antibodies specifically binding to PD-1 (hereinafter, may be abbreviated as an "anti-PD-1 antibody"), germ-line genes IGHV7-4-1 and JH6c. In this figure, "-" in the amino acid sequences of clones represents the same amino acid as that of the corresponding germ-line gene IGHV7-4-1 or JH6c, and abbreviations for amino acids represent amino acids different from that of the same germ-line gene.

FIG. 5 It shows a sequence alignment among the VH of the respective clones of antibodies specifically binding to CD19 (hereafter, may be abbreviated as an "anti-CD19 antibody".) and the amino acid sequence coded by the germ-line gene IGHV5-51. Each symbol in this figure represents the same meaning as that in FIG. 4.

FIG. 6 It shows the VH amino acid sequences of the respective anti-PD-1 antibody clones.

FIG. 7 It shows the respective CDR amino acid sequences in the VH of the respective anti-PD-1 antibody clones.

FIG. 8 It shows the VH amino acid sequences of the respective anti-CD19 antibody clones.

FIG. 9 It shows the respective CDR amino acid sequences in the VH of the respective anti-CD19 antibody clones.

FIG. 10 It shows the amino acid sequences of the respective heavy chain constant regions of the PD-1/CD19 bispecific monoclonal antibody.

FIG. 11 It shows the results from Biacore measurement, demonstrating the binding activities to PD-1 and CD19 of the respective PD-1/CD19 bispecific antibody clones.

FIG. 12 It shows flow cytometry demonstrating the binding properties to CD19 of the respective PD-1/CD19 bispecific antibody clones CD19-1(Bi) to CD19-3(Bi), respectively.

FIG. 13 It shows flow cytometry demonstrating the binding properties to CD19 of the respective PD-1/CD19 bispecific antibody clones CD19-4(Bi) and CD19-5(Bi), respectively.

FIG. 14 It shows flow cytometry demonstrating the binding properties to PD-1 of the respective PD-1/CD19 bispecific antibody clones CD19-1(Bi) to CD19-3(Bi), respectively.

FIG. 15 It shows flow cytometry demonstrating the binding properties to PD-1 of the respective PD-1/CD19 bispecific antibody clones CD19-4(Bi) and CD19-5(Bi), respectively.

FIG. 16 It shows flow cytometry demonstrating the binding properties to PD-1 and CD19 of the PD-1/CD19 bispecific antibody clone CD19-6(Bi), respectively.

FIG. 22 It shows effects on cytokine production from human peripheral-blood mononuclear cells of the PD-1/CD19 bispecific antibody clone CD19-6(Bi). Note here that in this figure, "Medium" represents control group.

DESCRIPTION OF EMBODIMENTS

Figure 17:
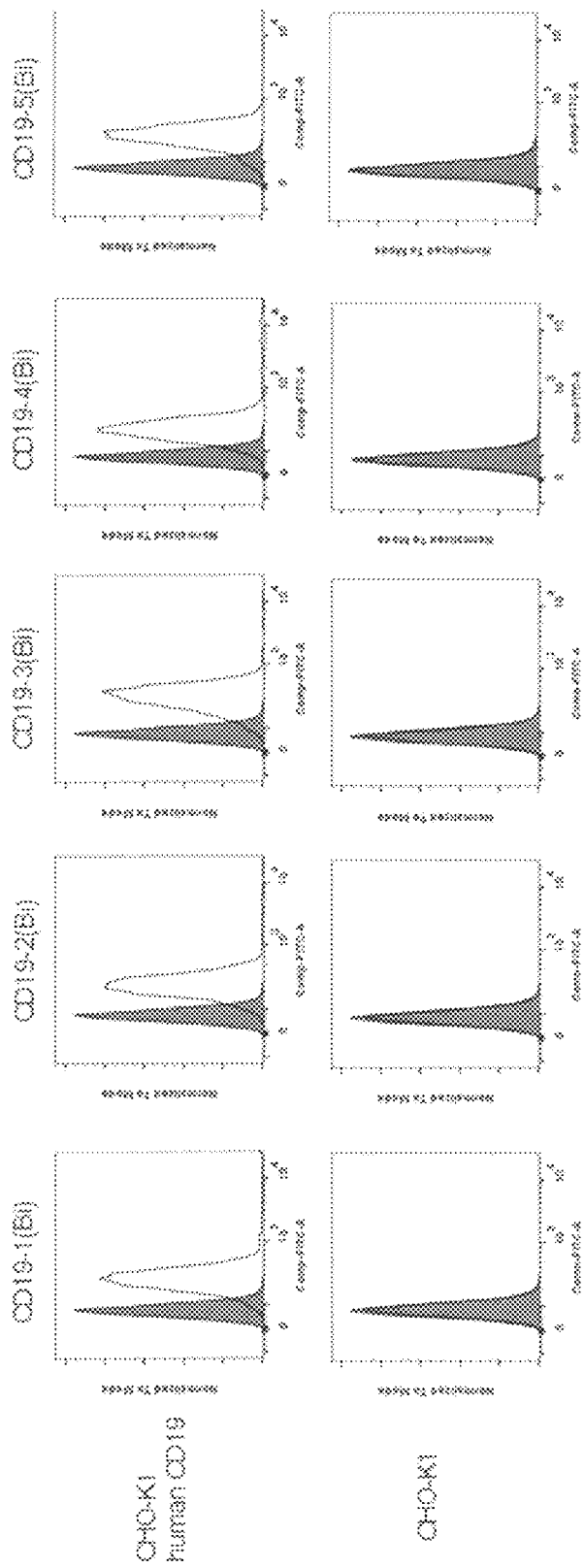
FIG. 17 It shows flow cytometry demonstrating the simultaneous binding properties to PD-1 and CD19 of the respective PD-1/CD19 bispecific antibody clones, respectively.

PD-1 (Programmed Cell Death-1) is a membrane-type protein composed of the amino acid sequence represented by GenBank accession number NP_005009 in human. In the present specification, the term "PD-1", unless specifically defined otherwise, may be used as a meaning including all of the isoforms thereof and further variants thereof in which an epitope for the "first arm specifically binding to PD-1" of the present invention has been conserved. In the present invention, PD-1 is preferably human PD-1.

CD19 is a membrane protein on B cells composed of the amino acid sequence represented by GenBank accession number NP_001171569 or NP_001761 in human, and a molecular transferring stimulations into B cell along with B cell receptor complex. In the present specification, the term "CD19", unless specifically defined otherwise, may be used as a meaning including variants thereof in which an epitope of the "second arm specifically binding to CD19" of the present invention has been conserved. In the present invention, CD19 is preferably human CD19.

In the present specification, the term "isolate" means becoming a single substantially pure component by being identified, separated and/or purified from impurities containing a plurality of or myriad number of components extracted from host cells.

In the present specification, the term "monoclonal antibody" means an antibody obtained from a substantially homogeneous antibody group binding to the same specific antigen.

In the present specification, the term "bispecific antibody" means an antibody having the binding specificity to two different antigen molecules or epitopes on one molecule. Furthermore, the term "bispecific monoclonal antibody" means a bispecific antibody obtained from a substantially homogeneous antibody group.

The present invention relates to a bispecific antibody capable of specifically binding to PD-1 and CD19, respectively (in the present specification, may be abbreviated as a "PD-1/CD19 bispecific antibody"). In the present invention, the PD-1/CD19 bispecific antibody is preferably a PD-1/CD19 bispecific monoclonal antibody, more preferably an isolated PD-1/CD19 bispecific monoclonal antibody, and furthermore preferably an isolated human PD-1/human CD19 bispecific monoclonal antibody. Herein, the "isolated human PD-1/human CD19 bispecific monoclonal antibody" means an isolated bispecific monoclonal antibody to human PD-1 and human CD19.

Herein, examples of forms of the bispecific antibodies include a diabody, bispecific sc(Fv)$_2$, bispecific minibody, bispecific F(ab')2, bispecific hybrid antibody, covalent diabody (bispecific DART), bispecific (FvCys)$_2$, bispecific F(ab'-zipper)$_2$, bispecific (Fv-zipper)$_2$, bispecific three-chain antibody and bispecific mAb$^2$ and the like.

The diabody is a dimer of single-chain peptides in which a VH and VL recognizing different antigens are linked to each other with a peptide linker (see Proc. Natl. Acad. Sci. USA (1993), Vol. 90, No. 14, pp. 6444-6448).

The bispecific sc(Fv)$_2$ is a low-molecular antibody modified such that two pairs of VH/VL of two antibodies recognizing different antigens are linked with a peptide linker to form a continuous single chain form (see J. Biological Chemistry (1994), 269: pp. 199-206).

The bispecific F(ab')2 is a low-molecular antibody in which Fab' fragments of antibodies recognizing two different antigens were covalently bonded through a disulfide bond or the like.

The bispecific minibody is a low-molecular antibody in which the low-molecular antibody fragments modified in such a manner that the constant region CH3 domains of the antibodies are linked to scFv recognizing different antigens, respectively, was covalently bonded by disulfide bonds or the like on the CH3 domains (see Biochemistry (1992), Vo. 31, No 0.6, pp. 1579-1584).

The bispecific hybrid antibody is an intact antibody in which heavy chain/light chain complexes of antibody, recognizing two different antigens were covalently bound each other through a disulfide bond or the like.

In the present invention, the form of the bispecific antibody is preferably a bispecific hybrid antibody.

The bispecific hybrid antibody can be produced from a hybridoma produced by, for example, hybrid hybridoma method (see U.S. Pat. No. 4,474,893). Alternatively, the bispecific hybrid antibody can be produced by having mammal animal cells co-express four kinds of cDNAs encoding a heavy chain and light chain of antibody recognizing different antigens, respectively, and secrete it.

The monoclonal antibodies used in the present invention can be produced by hybridoma method (see, e.g., Kohler and Milstein et al., Nature (1975), Vol. 256, p. 495-97, Hongo et al., Hybridoma (1995), Vol. 14, No. 3, pp. 253-260, Harlow et al., Antibodies: A Laboratory Manual, (Cold Spring Harbor Laboratory Press (1988), Vol. 2) and Hammerling et al., Monoclonal Antibodies and T-Cell Hybridomas, pp. 563-681 (Elsevier, N.Y., 1981)), recombinant DNA method (see, e.g., U.S. Pat. No. 4,816,567), phage display method (see, e.g., Ladner et al., U.S. Pat. Nos. 5,223,409, 5,403,484 and 5,571,698, Dower et al., U.S. Pat. Nos. 5,427,908 and 5,580,717, McCafferty et al., U.S. Pat. Nos. 5,969,108 and 6,172,197, and Griffiths et al., U.S. Pat. Nos. 5,885,793, 6,521,404, 6,544,731, 6,555,313, 6,582,915 and 6,593,081).

An antibody or monoclonal antibody, when being administered to human, can be produced in a form of a chimeric antibody, humanized antibody, or complete human antibody in order to reduce or eliminate its antigenicity.

The term "chimeric antibody" means an antibody of which the variable region sequence and constant region sequence are derived from different mammalian. Examples thereof include an antibody of which the variable region sequence is derived from a mouse antibody and the constant region sequence is derived from a human antibody. The chimeric antibody can be produced by linking a gene encoding an antibody variable region isolated from antibody-producing hybridomas isolated by the above-mentioned hybridoma method, recombinant DNA method or phage display method, by well-known techniques, to a gene encoding the constant region of human-derived antibody using well-known methods (see, e.g., Cabilly et al., U.S. Pat. No. 4,816,567).

The term "humanized antibody" means an antibody of which complementarity determining region (CDR) sequences derived from a germ line of other mammals such as mouse was grafted into human framework region sequences. The humanized antibody can also be produced by linking genes encoding the CDRs of antibody isolated from antibody-producing hybridomas isolated according to the above-mentioned method, by well-known techniques, to a gene encoding a framework region of the human-derived antibody using well-known methods (see, e.g., Winter, U.S. Pat. Nos. 5,225,539 and 5,530,101; Queen et al., U.S. Pat. Nos. 5,585,089 and 6,180,370).

The term "human antibody" or "complete human antibody" means an antibody in which both of variable regions composed of framework regions and CDR regions and constant regions are derived from human germline immunoglobulin sequences. The human antibody to be used in the present invention can be produced by a method using mice transformed to produce a human antibody, for example, Humab mice (see, e.g., Lonberg and Kay et al. U.S. Pat. Nos. 5,545,806, 5,569,825, 5,625,126, 5,633,425, 5,789,650, 5,877,397, 5,661,016, 5,814,318, 5,874,299 and 5,770,429), KM mice (see, e.g., Ishida et al., WO2002/43478), Xeno mice (see, e.g., U.S. Pat. Nos. 5,939,598, 6,075,181, 6,114,598, 6,150,584 and 6,162,963), or Tc mice (see, e.g., Tomizuka et al., Proc. Natl. Acad. Sci. USA (2000), pp. 722-727). It can also be prepared using SCID mice into which human immune cells have been reconstructed such that the human antibody response is made upon immunization (see, e.g., Wilson et al., U.S. Pat. Nos. 5,476,996 and 5,698,767). Furthermore, the human antibody to be used in the present invention can also be produced according to the above-mentioned phage display method.

In the present specification, the term "antibody fragment" of the PD-1/CD19 bispecific antibody is a part of the full-length antibody and is an antibody having an antigen binding part to PD-1 and an antigen binding part to CD19. Examples thereof include F(ab')2, and the like. Herein, the antigen binding part means a minimum unit of an antibody which can bind to an antigen thereof, for example, it is composed of three CDRs in the respective VH and VL and framework regions for arranging CDRs such that the target antigen can be recognized by combination of those CDRs.

In the present specification, the term "common light chain" means a light chain which can be associated with two or more different heavy chains and can exhibit the binding ability to each antigen (De Wildt R M, J. Mol. Biol. (1999), Vol. 285, pp. 895-901, De Kruif et al., J. Mol. Biol. (2009), Vol. 387, pp. 548-58, WO2004/009618, WO2009/157771 and WO2014/051433). Preferable examples of such common light chains include a light chain encoded by human κ light chain IgVκ1-39*01/IGJκ1*01 (nomenclatures of IMGT database) germ-line gene (hereinafter, may be abbreviated as "IGVK1-39/JK1 common light chain"). More preferable examples thereof include a light chain having a VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and further preferable examples thereof include a light chain having the VL comprising the amino acid sequence set forth in SEQ ID No. 25. Furthermore, preferable examples of the constant regions of common light chain include the light chain constant region comprising the amino acid sequence set forth in SEQ ID No. 29. The respective amino acid sequences of the VL and the constant region of common light chain used in the present invention are shown in FIG. 1, and the respective amino acid sequences of CDRs of the variable region are shown in FIG. 2.

In the present specification, the term "isotype" means the antibody class (e.g., IgM or IgG) which is encoded by heavy chain constant region genes. The isotype for the PD-1/CD19 bispecific antibody of the present invention is preferably IgG, more preferably $IgG_1$ or $IgG_4$. Herein, $IgG_1$ is preferably of which the binding to Fc receptor is eliminated or decreased. Specifically, the $IgG_1$ antibody of which the binding to Fc receptor is eliminated or decreased can be obtained by substituting, deleting or inserting arbitrary amino acids of the heavy chain constant region thereof. Examples thereof include an antibody in which leucine at position 235 according to the EU numbering system was substituted with glycine and/or glycine at position 236 was substituted with arginine on two heavy chain constant regions or hinge regions thereof, respectively. Further, in order to reduce the heterogeneity of antibody, an antibody in which an amino acid at the C-terminus, for example, lysine at position 447 according to the EU numbering system has been deleted is preferable. Furthermore, when the bispecific antibody is $IgG_4$, in order to suppress the swapping in an antibody molecule, a variant in which an arbitrary amino acid in a heavy chain constant region thereof was substituted, deleted or inserted is more preferable. For example, the antibody of which serine at position 228 according to the EU numbering system, located in the hinge region, was substituted with proline is preferable. Note herein that in the present specification, amino acid positions assigned to CDRs and framework regions in variable regions of antibody may be specified according to Kabat's numbering system (see Sequences of Proteins of Immunological Interest, National Institute of Health, Bethesda, Md., (1987) and 1991)). Further, amino acids in the constant region are indicated according to the EU numbering system according to Kabat's amino acid positions (see Sequences of proteins of immunological interest, NIH Publication No. 91-3242).

In the Fc regions of the PD-1/CD19 bispecific antibody of the present invention, arbitrary amino acids therein may be substituted such that two different heavy chains are easily associated with each other. Examples of preferable embodiments thereof include a PD-1/CD19 bispecific antibody of which in the constant region of the heavy chain having the VH of the first arm specifically binding to PD-1, leucine at position 351 according to the EU numbering system was substituted with lysine, and threonine at position 366 was substituted with lysine and of which in the constant region of the heavy chain having the VH of the second arm specifically binding to CD19, leucine at position 351 was substituted with aspartic acid, and leucine at position 368 was substituted with glutamic acid. Further, examples thereof also include a PD-1/CD19 bispecific antibody of which in the constant region in the heavy chain having the VH of the first arm specifically binding to PD-1, leucine at position 351 according to the EU numbering system was substituted with aspartic acid, and leucine at position 368 was substituted with glutamic acid and of which in the constant region of the heavy chain having the VH of the second arm specifically binding to CD19, leucine at position 351 was substituted with lysine and threonine at position 366 was substituted with lysine.

The First Arm Specifically Binding to PD-1

In the present specification, the "first arm specifically binding to PD-1" (hereinafter, may be abbreviated as the "first arm") means a part of antibody having at least a VH of antibody specifically binding to PD-1 and capable of specifically binding to PD-1, regardless of whether it is contained in a part of antibody or antibody fragment thereof, or exists not as a part but as a simple substance. For example, the first arm like this is composed of a VH of the anti-PD-1 antibody and a VL of the common light chain which can constitute the same anti-PD-1 antibody, and further examples thereof also include a Fab of antibody having the same VH and VL. Herein, the term "specifically binding to PD-1" is used as a feature of directly binding to PD-1 with higher binding activity than at least $1×10^{-5}$M, preferably $1×10^{-7}$ M, and more preferably $1×10^{-9}$ M affinity (dissociation constant (Kd value)), and not substantially binding to any receptor members belonging to a so-called CD28 family receptor, such as at least CD28, CTLA-4 and ICOS. Furthermore, an "antibody" in the "antibody specifically binding to PD-1" or in the "anti-PD-1 antibody" means a full-length antibody, that is, a full-length antibody consisting of two heavy chains and two light chains linked with disulfide bonds, and preferably a monoclonal antibody thereof.

Herein, examples of the "first arm specifically binding to PD-1" include those having the VH having
- (a) the VH-CDR1 comprising the amino acid sequence represented by $HYJ^1LH$ [wherein $J^1$ represents G (glycine) or A (alanine), and other alphabets represent one-letter amino acid abbreviations, respectively],
- (b) the VH-CDR2 comprising the amino acid sequence represented by $WJ^2NTNTU^2NPTX^2AQGFTG$ [wherein $J^2$ represents L (leucine) or I (isoleucine), $U^2$ represents E (glutamic acid) or G (glycine), $X^2$ represents F (phenylalanine) or Y (tyrosine), and other alphabets represent the same as the above, respectively], and
- (c) the VH-CDR3 comprising the amino acid sequence represented by $GDJ^3VVPTTIWNYYU^3X^3MZ^3V$ [wherein $J^3$ represents M (methionine) or L (leucine), $U^3$ represents H (histidine) or Y (tyrosine), $X^3$ represents F (phenylalanine) or Y (tyrosine), $Z^3$ represents D (aspartic acid) or E (glutamic acid), and other alphabets represent the same as the above, respectively].

Furthermore, examples of other embodiments of the "first arm specifically binding to PD-1" include those having any one of the VH selected from
- (1b) the VH having the VH-CDR1 comprising the amino acid sequence set forth in SEQ ID No. 6, the VH-CDR2 comprising the amino acid sequence set forth in SEQ ID No. 7, and the VH-CDR3 comprising the amino acid sequence set forth in SEQ ID No. 8,
- (2b) the VH having the VH-CDR1 comprising the amino acid sequence set forth in SEQ ID No. 9, the VH-CDR2 comprising the amino acid sequence set forth in SEQ ID No. 10, and the VH-CDR3 comprising the amino acid sequence set forth in SEQ ID No. 11,
- (3b) the VH having the VH-CDR1 comprising the amino acid sequence set forth in SEQ ID No. 12, the VH-CDR2 comprising the amino acid sequence set forth in SEQ ID No. 13, and the VH-CDR3 comprising the amino acid sequence set forth in SEQ ID No. 14, (4b) the VH having the VH-CDR1 comprising the amino acid sequence set forth in SEQ ID No. 15, the VH-CDR2 comprising the amino acid sequence set forth in SEQ ID No. 16, and the VH-CDR3 comprising the amino acid sequence set forth in SEQ ID No. 17, and (5b) the VH having the VH-CDR1 comprising the amino acid sequence set forth in SEQ ID No. 18, the VH-CDR2 comprising the amino acid sequence set forth in SEQ ID No. 19, and the VH-CDR3 comprising the amino acid sequence set forth in SEQ ID No. 20.

Furthermore, examples of the "first arm specifically binding to PD-1" of the present invention include those of which one to five arbitrary amino acid residues are substituted with other amino acids (preferably, conservative amino acids thereof) in the respective VH-CDRs of any one of the VH selected from the above-mentioned (1b) to (5b), and which have substantially the same binding activity to PD-1 as that of the original first arm without any substitutions with the same amino acids. Examples thereof include those of which one amino acid residue in the VH-CDR1 is substituted with other amino acids (preferably, conservative amino acids thereof), and one to five amino acid residues in the VH-CDR2 or VH-CDR3 are substituted with other amino acids (preferably, conservative amino acids thereof), respectively. Further, as shown in FIG. 4, in the respective CDRs of the anti-PD-1 antibody clones corresponding to the first arms specifically binding to PD-1, respectively, amino acids different among the clones or any combination of a plurality thereof can be exchangeable each other among the clones. Herein, the substitution with a conservative amino acid means the exchangeability with a residue having a similar side-chain. For example, a group of amino acids having an aliphatic side-chain includes glycine, alanine, valine, leucine, and isoleucine; a group of amino acids having an aliphatic hydroxyl side-chain includes serine and threonine; a group of amino acids having amide-containing side-chain includes asparagine and glutamine; a group of amino acids having an aromatic side-chain includes phenylalanine, tyrosine and tryptophan; a group of amino acids having a basic side-chain includes lysine, arginine and histidine; and a group of amino acids having a sulfur-containing side-chain includes cysteine and methionine. Examples of preferable substitutions with a conservative amino acid include that among valine, leucine and isoleucine, that between phenylalanine and tyrosine, that between lysine and arginine, that between alanine and valine, as well as that between asparagine and glutamine. Furthermore, herein, the sentence "which have substantially the same binding activity to PD-1 as that of the original first arm without any substitutions with the amino acids" mentioned above means that the binding activity to PD-1 of the first arm substituted with the same amino acids is 95% or more, preferably 98% or more, and more preferably 99% or more to that of the original first arm without any substitutions with the same amino acids.

Furthermore, examples of the "first arm specifically binding to PD-1" of the present invention include those having a VH which contains the respective VH-CDRs having the above-mentioned specific amino acid sequences therein, and of which the amino acid sequence of framework region is encoded by a specific germ-line gene or a gene thereof with somatic mutation(s). For example, the VH represented by any one selected from the above-mentioned (1b) to (5b) can be encoded by the VDJ recombinant gene or gene thereof with somatic mutation(s) in which the germ-line V gene is IGHV7-4-1 and the germ-line J gene is JH6c. Herein, the amino acid sequence encoded by the germ-line V gene IGHV7-4-1 corresponds to that set forth in SEQ ID No. 21 (FIG. 3).

The framework region in the VH of the first arm specifically binding to PD-1 of the present invention may be encoded by the germ-line VDJ recombinant gene with somatic mutation(s). For example, since the FR1, FR2, and FR3 in the VH represented by any one selected from the above-mentioned (1b) to (5b) of which a germ-line V gene is IGHV7-4-1 are different from the amino acid sequence encoded by the IGHV7-4-1 gene at the position of amino acid shown in FIG. 4, they have undergone somatic mutations at the respective same positions. For example, as to the FR1, in the amino acid sequence set forth in SEQ ID No. 21, lysine at position 13 may be substituted with glutamine, alanine at position 16 may be substituted with valine, or lysine at position 19 may be substituted with methionine, respectively, or which may be substituted in an arbitrary combination of a plurality thereof. As to the FR2, valine at position 37 in the amino acid sequence set forth in SEQ ID No. 21 may be substituted with leucine. As to the FR3, in the amino acid sequence set forth in SEQ ID No. 21, serine at position 77 may be substituted with threonine, or cysteine at position 84 may be substituted with serine or asparagine, respectively, or which may be substituted in an arbitrary combination of a plurality thereof. Furthermore, as to the FR4 of the VH represented by any one selected from the above-mentioned (1b) to (5b), in the amino acid sequence (Trp-Gly-Lys-Gly-Thr-Thr*-Val-Thr-Val-Ser-Ser) (SEQ ID No. 41) of the FR4 derived from the J gene JH6c, lysine (Lys) may be substituted with glutamine or asparagine, and/or threonine (Thr) marked with an asterisk may be substituted with leucine. The respective FR1, FR2, FR3 and FR4 having combination of any amino acid substitutions mentioned above have no substantial effect on the functions of the first arm specifically binding to PD-1, and can be used as framework regions.

Further, examples of the "first arm specifically binding to PD-1" of the present invention also include those which have the respective CDRs having the amino acid sequence specified as the above and in which the FR amino acid sequences in the VH are encoded by the specific germ-line gene or gene thereof with somatic mutation(s). Examples of such first arms include those having the VH comprising the amino acid sequence in any one selected from SEQ ID Nos. 1 to 5.

Furthermore, examples of such "first arms specifically binding to PD-1" also include those which have a VH comprising an amino acid sequence having at least 80% identity, preferably at least 90% identity, more preferably at least 95% identity, furthermore preferably at least 98% identity, and further more preferably at least 99% identity to the amino acid sequence set forth in any one selected from SEQ ID Nos. 1 to 5, and in which the difference from the VH amino acid sequence of the original first arm has no substantial effect on the binding activity to PD-1 (hereinafter, may be abbreviated as a "homologous first arm"). Herein, the term "% identity" used in comparison of the identity of amino acid sequences is defined as the percentage of amino acid sequence identical to the reference amino acid sequence (herein, when being needed to maximize the sequence identity, the reference amino acid sequence in which the gap has been introduced) when two sequences are aligned. Furthermore, herein, the sentence "the different from the VH amino acid sequence of the original first arm has no substantial effect on the binding activity to PD-1" means that the binding activity to PD-1 of the homologous first arm is 95% or more, preferably 98% or more, and more preferably 99% or more to that of the original first arm.

In a yet another embodiment, the "first arm specifically binding to PD-1" of the present invention also includes those having a variable region (herein, the variable region contains a VH and VL constituting it.) of the anti-PD-1 antibody cross-competing for (1) the binding to PD-1 with the first arm having the VH represented by any one selected from the above-mentioned (1b) to (5b) or the VH comprising the amino acid sequence set forth in any one selected from SEQ ID Nos. 1 to 5 and the VL of the common light chain of the present specification (preferably, the VL comprising the amino acid sequence set forth in SEQ ID No. 25), or (2) the binding to PD-1 with the variable region of monoclonal antibody specifically binding to PD-1 having the same VH and VL, and further includes those having the variable region of the anti-PD-1 antibody with which the binding to PD-1 is cross-competed by (3) the first arm having the VH represented by any one selected from the above-mentioned (1b) to (5b) or the VH comprising the amino acid sequence set forth in any one selected from SEQ ID Nos. 1 to 5 and the VL of the same common light chain, or (4) the variable region of monoclonal antibody specifically binding to PD-1 having the same VH and VL. Herein, the sentence "cross-competing for the binding to PD-1" means inhibiting the binding of the first arm to PD-1, regardless of the degree thereof, by binding to the epitope which is the same as or partially overlaps with that of the first arm exemplified in the present specification, or that the binding to PD-1 of the antibody binding to the epitope which is the same as or partially overlaps with that of the exemplified first arm is inhibited by the same exemplified first arm, regardless of the degree thereof. Whether it cross-competes or not can be evaluated by a competitive binding assay. For example, it can be determined using Biacore analysis, ELISA assay, flow cytometry, enzyme linked immunosorbent assay (ELISA), fluorescence energy transfer method (FRET) and fluorometric microvolume assay technology (FMAT (registered trademark)).

Examples of the first arm cross-competing for the binding to PD-1 by the first arm having the VH represented by the above-mentioned (5b) and the VL of common light chain include the first arm having the VH represented by any one selected from the above-mentioned (1b) to (4b) and the VL of common light chain (preferably, the VL having the VL-CDR1 comprising the amino acid sequence set forth in SEQ ID No. 26, the VL-CDR2 comprising the amino acid sequence set forth in SEQ ID No. 27 and the VL-CDR3 comprising the amino acid sequence set forth in SEQ ID No. 28), and further the first arm having the VH comprising the amino acid sequence set forth in any one selected from SEQ ID Nos. 1 to 4 and the VL of common light chain (preferably, the VL comprising the amino acid sequence set forth in SEQ ID No. 25).

Furthermore, examples of the first arm cross-competing for the binding to PD-1 with the first arm having the VH represented by any one selected from the above-mentioned (1b) to (4b) or the VH comprising the amino acid sequence set forth in any one selected from SEQ ID Nos. 1 to 4 and the VL of common light chain include the first arm having the VH represented by the above-mentioned (5b) and the VL of common light chain (preferably, the VL having the VL-CDR1 comprising the amino acid sequence set forth in SEQ ID No. 26, the VL-CDR2 comprising the amino acid sequence set forth in SEQ ID No. 27 and the VL-CDR3 comprising the amino acid sequence set forth in SEQ ID No. 28), and further the first arm having the VH comprising the amino acid sequence set forth in SEQ ID No. 5 and the VL of common light chain (preferably, the VL comprising the amino acid sequence set forth in SEQ ID No. 25).

Herein, preferable examples of the "first arm specifically binding to PD-1" of the present invention include the first arm having the VH represented by any one selected from the above-mentioned (1b) to (5b). Furthermore, as mentioned above, preferable examples of the first arm also include those having the VH of which one to five arbitrary amino acid residues are substituted with other amino acids (preferably, conservative amino acids thereof) in the respective CDRs and the same substitutions do not substantially affect the binding activity to PD-1. Furthermore, as mentioned above, they also include those having the VH in which the amino acid sequences of framework regions are encoded by the germ-line V gene IGHV7-4-1 or J gene JH6c or genes thereof with somatic mutation(s). Then, more preferable examples of the first arm include those having the VH comprising the amino acid sequence set forth in any one selected from SEQ ID Nos. 1 to 5.

Furthermore, the "first arm specifically binding to PD-1" of the present invention is preferably those having the VL of the common light chain of the present specification, and such a common light chain is preferably the IGVK1-39/JK1 common light chain. A more preferable example thereof is a light chain having the VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and a further preferable example thereof is the light chain containing the VL comprising the amino acid sequence set forth in SEQ ID No. 25. Furthermore, preferable examples of the constant regions of common light chain include the light chain constant region comprising the amino acid sequence set forth in SEQ ID No. 29.

Furthermore, the "first arm specifically binding to PD-1" is preferably one allowing the interaction between PD-1 and PD-L1, interaction between PD-1 and PD-L2, or both of interactions thereof. Herein, the sentence "allowing the interaction between PD-1 and PD-L1, interaction between PD-1 and PD-L2, or both of interactions thereof" means that even when there is the PD-1/CD19 bispecific antibody of the present invention at 20-fold excess over the concentration of the soluble form PD-L1 or PD-L2, the interaction between PD-L1 and PD-1, interaction between PD-L2 and PD-1 or both of interactions thereof is maintained 50% or more, preferably 70% or more, and more preferably 80% or more, compared with those when there is no PD-1/CD19 bispecific antibody of the present invention. Furthermore, the definition of "allowing the interaction between PD-1 and PD-L1, interaction between PD-1 and PD-L2, or both of interactions thereof" may have the same meaning as that of "which does not substantially inhibit the interaction between PD-1 and PD-L1, interaction between PD-1 and PD-L2, or both of interactions thereof".

The correspondence relations between the respective the anti-PD-1 monoclonal antibody clones obtained to construct the PD-1/CD19 bispecific antibody of the present invention and VH amino acid sequences thereof and SEQ ID numbers thereof are shown in FIG. 6. The correspondence relations between the CDR amino acid sequences in the VH of the respective anti-PD-1 monoclonal antibody clones and SEQ ID number thereof are shown in FIG. 7.

The Second Arm Specifically Binding to CD19

In the present specification, the "second arm specifically binding to CD19" (hereinafter, may be abbreviated as the "second arm") means a part of antibody having at least a VH of an antibody specifically binding to CD19 and capable of specifically binding to CD19, regardless of whether it is contained in a part of antibody or antibody fragment thereof, or exists not as a part but as a simple substance. For example, such a second arm is composed of a VH of the anti-CD19 antibody and the VL of common light chain which can constitute the same anti-CD19 antibody, and further examples thereof include a Fab part of antibody including the same VH and VL. Herein, the sentence "specifically binding to CD19" is used as a feature of directly binding to CD19 with higher binding activity than at least $1\times10^{-5}$ M, preferably $1\times10^{-7}$ M, and more preferably more than $1\times10^{-9}$ M affinity (dissociation constant (Kd value)), and does not substantially bind to any other proteins. Furthermore, the "antibody" in the "antibody specifically binding to CD19" or in the "anti-CD19 antibody" means a full-length antibody consisting of two heavy chains and two light chains linked with disulfide bonds, and preferably a monoclonal antibody thereof.

Herein, examples of the "second arm specifically binding to CD19" include those having the VH having (a) the VH-CDR1 comprising the amino acid sequence represented by SYWIJ$^4$ [wherein J$^4$ represents G (glycine) or A (alanine), and other alphabets represent one-letter amino acid abbreviations, respectively], (b) the VH-CDR2 comprising the amino acid sequence represented by IIU$^4$PGDSDTRYSPSFQG [wherein U$^4$ represents W (tryptophan) or Y (tyrosine), or other alphabets represent the same as the above, respectively], and (c) the VH-CDR3 comprising the amino acid sequence represented by X$^4$TIVZ$^4$J$^5$U$^5$X$^5$Z$^5$AJ$^6$DU$^6$ [wherein X$^4$ represents K (lysine), Q (glutamine), H (histidine) or R (arginine), Z$^4$ represents G (glycine) or A (alanine), J$^5$ represents T (threonine) or V (valine), U$^5$ represents V (valine), I (isoleucine) or T (threonine), X$^5$ represents M (methionine), Y (tyrosine), G (glycine) or H (histidine), Z$^5$ represents T (threonine), N (asparagine), L (leucine) or W (tryptophan), J$^6$ represents F (phenylalanine) or S (Serine), and U$^6$ represents I (isoleucine), F (phenylalanine) or Y (tyrosine) and other alphabets represent the same as the above, respectively].

Further, examples of other embodiments of the "second arm specifically binding to CD19" include those having any one of VH selected from
- (1d) a VH having the VH-CDR1 comprising the amino acid sequence set forth in SEQ ID No. 35, the VH-CDR2 comprising the amino acid sequence set forth in SEQ ID No. 36, and the VH-CDR3 comprising the amino acid sequence set forth in SEQ ID No. 37,
- (2d) a VH having the VH-CDR1 comprising the amino acid sequence set forth in SEQ ID No. 38, the VH-CDR2 comprising the amino acid sequence set forth in SEQ ID No. 39, and the VH-CDR3 comprising the amino acid sequence set forth in SEQ ID No. 40,
- (3d) a VH having the VH-CDR1 comprising the amino acid sequence set forth in SEQ ID No. 41, the VH-CDR2 comprising the amino acid sequence set forth in SEQ ID No. 42, and the VH-CDR3 comprising the amino acid sequence set forth in SEQ ID No. 43,
- (4d) a VH having the VH-CDR1 comprising the amino acid sequence set forth in SEQ ID No. 44, the VH-CDR2 comprising the amino acid sequence set forth in SEQ ID No. 45, and the VH-CDR3 comprising the amino acid sequence set forth in SEQ ID No. 46, and
- (5d) a VH having the VH-CDR1 comprising the amino acid sequence set forth in SEQ ID No. 47, the VH-CDR2 comprising the amino acid sequence set forth in SEQ ID No. 48, and the VH-CDR3 comprising the amino acid sequence set forth in SEQ ID No. 49.

Furthermore, examples of the "second arm specifically binding to CD19" of the present invention also include those in which one to five arbitrary amino acid residues are substituted with other amino acids (preferably, conservative amino acids thereof) in the respective VH-CDRs of any one of VH selected from the above-mentioned (1d) to (5d), and which have substantially the same binding activity to CD19 as that of the original second arm without any substitutions with the same amino acids. Examples thereof include those of which one amino acid residue in the VH-CDR1 is substituted with other amino acids (preferably, a conservative amino acid thereof), and one to five amino acid residues in the VH-CDR2 or VH-CDR3 are substituted with other amino acids (preferably, conservative amino acids thereof), respectively. Further, as shown in FIG. 5, in the respective CDRs of the anti-CD19 antibody clones corresponding to the first arms specifically binding to CD19, respectively, amino acids different among the clones or any combination of a plurality thereof can be exchangeable each other among the clones. Herein, the sentence "which have substantially the same binding activity to CD19 as that of the original second arm without any substitutions with the same amino acids" mentioned above means that the binding activity to CD19 of the second arm substituted with the same amino acids is 95% or more, preferably 98% or more, and more preferably 99% or more to that of the original second arm without any substitutions with the same amino acids. Note herein that examples of the "substitution with conservative amino acids" in the respective VH-CDRs of the second arm include those of the amino acid substitutions in the first arm mentioned above.

Furthermore, the "second arm specifically binding to CD19" in the present invention also includes those having a VH which contains the respective CDRs comprising the above-mentioned specific amino acid sequence, and of which the FR amino acid sequences are encoded by a specific germ-line gene or gene thereof with somatic mutation(s). For example, any one of the VH selected from the above-mentioned (1d) to (5d) can be encoded by a VDJ recombinant gene or gene thereof with somatic mutation(s) in which the germ-line V gene is IGHV5-51. Herein, the amino acid sequence encoded by the V gene IGHV5-51 of the germ line corresponds to the amino acid sequence set forth in SEQ ID No. 22 (FIG. 3).

The framework regions in the VH of the second arm specifically binding to CD19 of the present invention may be encoded by the germ-line VDJ recombinant gene with somatic mutation(s). For example, since the FR1 and FR3 in the VH represented by any one selected from the above-mentioned (1d) to (5d) of which the germ-line V gene is IGHV5-51 are different from an amino acid sequence encoded by the IGHV5-51 gene at the positions of the amino acid shown in FIG. 5, they have undergone somatic mutations at the respective same positions. For example, as to the FR1, in the amino acid sequence set forth in SEQ ID No. 22, glutamic acid at position 1 may be substituted with glutamine, proline at position 14 may be substituted with serine, tyrosine at position 27 may be substituted with phenylalanine, or threonine at position 30 may be substituted with isoleucine, respectively, or which may be substituted in an arbitrary combination of a plurality thereof. As to the FR3, in the amino acid sequence set forth in SEQ ID No. 22, isoleucine at position 76 may be substituted with phenylalanine, or serine at position 77 may be substituted with threonine or asparagine, threonine at position 78 may be substituted with valine, serine at position 84 may be substituted with asparagine, methionine at position 93 may be substituted with isoleucine or leucine, or alanine at position 97 may be substituted with valine, respectively, or which may be substituted in an arbitrary combination of a plurality thereof. The respective FR1 and FR3 having combination of any of the foregoing amino acid substitution have no substantial effect on the functions of the second arm specifically binding to CD19, and can be used as framework regions.

Furthermore, examples of the "second arm specifically binding to CD19" of the present invention also include those having the VH which contains the respective CDRs comprising the above-mentioned specific amino acid sequence, and of which the FR amino acid sequence is encoded by a specific germ-line gene or gene thereof with somatic mutation(s). Examples of such second arms include those having the VH comprising the amino acid sequence set forth in any one selected from SEQ ID Nos. 30 to 34.

Furthermore, examples of such "second arms specifically binding to CD19" also include those which have a VH comprising an amino acid sequence having at least 80%, preferably at least 90%, more preferably at least 95%, further more preferably at least 98%, and furthermore preferably at least 99% identity to the amino acid sequence set forth in any one selected from SEQ ID Nos. 30 to 34, and in which the difference from the VH amino acid sequence of the original second arm has no substantial effect on the binding activity to CD19 (hereinafter, may be abbreviated as a "homologous second arm"). Herein, the sentence "the difference from the VH amino acid sequence of the original second arm has no substantial effect on the binding activity to CD19" means that the binding activity of the homologous second arm to CD19 is 95% or more, preferably 98% or more, and more preferably 99% or more to that of the original second arm.

In a yet another embodiment, examples of the "second arm specifically binding to CD19" of the present invention also include those having a variable region (herein, the variable region contains the VH and VL constituting it) of the anti-CD19 antibody cross-competing for (1) the binding to CD19 with the second arm having the VH represented by any one selected from the above-mentioned (1d) to (5d), or the VH comprising the amino acid sequence set forth in any one selected from SEQ ID Nos. 30 to 34 and the VL of the common light chain of the present specification (preferably, the VL comprising the amino acid sequence set forth in SEQ ID No. 25), or (2) the binding to CD19 with the variable region of monoclonal antibody specifically binding to CD19 having the same VH and VL, and further include those having a variable region of the anti-CD19 antibody with which the binding to CD19 is cross-competed by (3) the second arm having the VH represented by any one selected from the above-mentioned (1d) to (5d), or the VH comprising the amino acid sequence set forth in any one selected from SEQ ID Nos. 30 to 34 and the same VL of common light chain, or (4) the variable region of monoclonal antibody specifically binding to CD19 having the same VH and VL. Herein, the "cross-competing for the binding to CD19" means inhibiting the binding of the second arm to CD19, regardless of the degree thereof, by binding to an epitope which is the same as or partially overlaps with the second arm exemplified in the present specification, or that the binding to CD19 of the antibody binding to the epitope which is the same as or partially overlaps with that of the exemplified second arm is inhibited by the same exemplified second arm, regardless of the degree thereof. Herein, whether it cross-competes or not can be similarly evaluated according to the same method as described in descriptions regarding the "first arm specifically binding to PD-1".

Herein, preferable examples of the "second arm specifically binding to CD19" of the present invention include the second arm having the VH represented by any one selected from the above-mentioned (1d) to (5d). Furthermore, as mentioned above, preferable examples of the second arm also include those having the VH of which one to five arbitrary amino acid residues are substituted with other amino acids (preferably, conservative amino acids thereof) in the respective CDRs and the same substitutions do not substantially affect the binding activity to CD19. Furthermore, as mentioned above, examples of the second arm include those having the VH in which the amino acid sequences of framework regions are encoded by the germ-line V gene IGHV5-51 or gene thereof with somatic mutation(s). Then, more preferable examples of the second arm include those having the VH comprising the amino acid sequence set forth in any one selected from SEQ ID Nos. 30 to 34.

Further, examples of other preferable embodiments of the second arm specifically binding to CD19" of the present invention include the second arm having the VH comprising any one of the amino acid sequence selected from SEQ ID No. 30 to 34 in which glutamine at position 114 was or may be substituted with arginine, more preferably, the second arm having the VH comprising any one of the amino acid sequence selected from SEQ ID No. 30 to 34 in which glutamine at position 114 was substituted by arginine, which correspond to the second arm having the VH comprising any one of the amino acid sequence selected from SEQ ID No. 62 to 66, respectively. These amino acid substitutions can increase the isoelectric point (pI value) of a complex consisting of the heavy chain and light chain having the second arm (hereafter, the second arm-heavy chain/light chain complex) and thereby makes easy to separate the bispecific antibody from, in particular, homodimers consisting of the second arm-heavy chain/light chain complexes, in the purification process of the PD-1/CD19 bispecific antibody of the present invention. The isoelectric point for the second arm-heavy chain/light chain complex is preferably between about 8.3 and about 8.9, and more preferably, between about 8.4 and about 8.8. And, the isoelectric point for a complex consisting of the heavy chain and light chain having the first arm (hereafter, the first arm-heavy chain/light chain complex) is preferably between about 7.4 and about 7.7, and more preferably, between about 7.5 and about 7.6.

The "second arm specifically binding to CD19" of the present invention is preferably those having the common light chain of the present specification, and such a common light chain is preferably the IGVK1-39/JK1 common light chain. A more preferable example thereof is the light chain having a VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and a further preferable example thereof is the light chain having the VL comprising the amino acid sequence set forth in SEQ ID No. 25. Furthermore, preferable examples of the constant region of the common light chain include the light chain constant region comprising the amino acid sequence set forth in SEQ ID No. 29.

Hereinafter, the correspondence relations between the respective anti-CD19 antibody clones to construct the PD-1/CD19 bispecific antibody of the present invention and the VH amino acid sequence thereof, and SEQ ID numbers thereof are shown in FIG. 8. The correspondence relations between the respective CDR amino acid sequences in the VH of the respective anti-CD19 antibody clones and SEQ ID number thereof are shown in FIG. 9.

On the other hand, examples of preferable embodiments of the PD-1/CD19 bispecific antibodies of the present invention include those of which the first arm specifically binding to PD-1 has (A) the VH in which one to five arbitrary amino acid residues may be substituted with other amino acids (preferably, conservative amino acids thereof) in any one or more of the CDRs selected from the VH-CDR1, VH-CDR2 and VH-CDR3 of the VH represented by any one selected from the above-mentioned (1b) to (5b), and (B) the VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and the second arm specifically binding to CD19 has (C) the VH in which one to five arbitrary amino acid residues may be substituted with other amino acids (preferably, conservative amino acids thereof) in any one or more of the CDRs selected from the VH-CDR1, VH-CDR2 and VH-CDR3 of the VH represented by any one selected from the above-mentioned (1d) to (5d), and (D) the VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28.

More preferable examples of the PD-1/CD19 bispecific antibodies of the present invention include those of which the first arm specifically binding to PD-1 has (A) the VH represented by any one selected from the above-mentioned (1b) to (5b), and (B) the VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28, and the second arm specifically binding to CD19 has (C) the VH represented by any one selected from the above-mentioned (1d) to (5d), and (D) the VL having the CDR1 comprising the amino acid sequence set forth in SEQ ID No. 26, the CDR2 comprising the amino acid sequence set forth in SEQ ID No. 27, and the CDR3 comprising the amino acid sequence set forth in SEQ ID No. 28.

Furthermore, examples of other preferable embodiments of the PD-1/CD19 bispecific antibodies of the present invention include those of which the first arm specifically binding to PD-1 has (A) the VH comprising the amino acid sequence set forth in any one selected from SEQ ID Nos. 1 to 5, or a VH comprising an amino acid sequence having at least 80% identity to the same VH amino acid sequence, and (B) the VL comprising the amino acid sequence set forth in SEQ ID No. 25, and the second arm specifically binding to CD19 has (C) the VH comprising the amino acid sequence set forth in any one selected from SEQ ID Nos. 30 to 34 and 62 to 66, or a VH comprising an amino acid sequence having an identity of at least 80% to the same VH amino acid sequence, and (D) the VL comprising the amino acid sequence set forth in SEQ ID No. 25.

Other more preferable examples thereof include the PD-1/CD19 bispecific antibody of which the first arm specifically binding to PD-1 has (A) the VH comprising the amino acid sequence set forth in any on selected from SEQ ID Nos. 1 to 5, and (B) the VL comprising the amino acid sequence set forth in SEQ ID No. 25, and the second arm specifically binding to CD19 has (C) the VH comprising the amino acid sequence set forth in any one selected from SEQ ID Nos. 30 to 34 and 62 to 66, and (D) the VL comprising the amino acid sequence set forth in SEQ ID No. 25.

Furthermore, other furthermore preferable examples thereof include the PD-1/CD19 bispecific antibody of which the first arm specifically binding to PD-1 has (A) the VH comprising the amino acid sequence set forth in any on selected from SEQ ID Nos. 1 to 5, and (B) the VL comprising the amino acid sequence set forth in SEQ ID No. 25, and wherein the second arm specifically binding to CD19 has (C) the VH comprising the amino acid sequence set forth in any one selected from SEQ ID Nos. 62 to 66, and (D) the VL comprising the amino acid sequence set forth in SEQ ID No. 25.

An isotype of the PD-1/CD19 bispecific antibody of the present invention is preferably an IgG antibody, further preferably, an IgG$_1$ antibody or IgG$_4$ antibody, and furthermore preferably, an IgG$_1$ antibody. When the antibody is an IgG$_1$ antibody, the IgG$_1$ antibody in which leucine at position 235 according to the EU numbering system was substituted with glycine, and/or glycine at position 236 was substituted with arginine on two heavy chain constant regions or hinge regions thereof is preferable. Further, the bispecific antibody of which the C-terminal amino acids of heavy chains, for example, lysine at position 447 according to the EU numbering system have been deleted is preferable. Furthermore, when the PD-1/CD19 bispecific antibody is an IgG$_4$ antibody, an antibody of which serine at position 228 according to the EU numbering system, located in the hinge region, was substituted with proline is preferable.

Furthermore, when the PD-1/CD19 bispecific antibody is an IgG$_1$ antibody, examples of preferable embodiments thereof include those of which in the constant region of the heavy chain having the VH of the first arm specifically binding to PD-1, leucine at position 351 according to the EU numbering system was substituted with lysine and threonine at position 366 was substituted with lysine, and in the constant region of the heavy chain having the VH of the second arm specifically binding to CD19, leucine at position 351 was substituted with aspartic acid and leucine at position 368 was substituted with glutamic acid. Furthermore, an IgG$_1$ antibody of which in the constant region of the heavy chain having the VH of the first arm specifically binding to PD-1, leucine at position 351 according to the EU numbering system was substituted with aspartic acid and leucine at position 368 was substituted with glutamic acid, and in the constant region of the heavy chain having the VH of the second arm specifically binding to CD19, leucine at position 351 was substituted with lysine and threonine at position 366 is substituted with lysine was also preferable, as well.

Examples of preferable embodiments of the PD-1/CD19 bispecific IgG$_1$ antibody in which all of the above-mentioned amino acid substitutions in the heavy chain constant region were taken include those in which the heavy chain having the VH of the first arm specifically binding to PD-1 has the heavy chain constant region comprising the amino acid sequence set forth in SEQ ID No. 23, and the heavy chain having the VH of the second arm specifically binding to CD19 has the heavy chain constant region comprising the amino acid sequence set forth in any one selected from SEQ ID No. 24 and SEQ ID No. 71 to 75. Those amino acid sequences are exemplified in FIG. 10.

Herein, the heavy chain having the VH of the second arm specifically binding to CD19 may further have Gly (glycine), Gly-Lys-Lys-Ala (SEQ ID No. 67), Gly-Lys-Ala-Lys-Ala (SEQ ID No. 68), Gly-Arg-Arg-Ala (SEQ ID No. 69) or Gly-Arg-Ala-Arg-Ala (SEQ ID No. 70), via amide binding to its C-terminal amino acid at its C-terminus. Addition of the amino acid or peptide can increase the isoelectric point (pI value) of the second arm-heavy chain/light chain complex, and thereby makes easy to separate the PD-1/CD19 bispecific antibody of the present invention from, in particular, a homodimer consisting of the second arm-heavy chain/light chain complexes, as with the case of the amino acid substitution in the VH of the second arm, mentioned above. Note here that the isoelectric point with regard to the second arm-heavy chain/light chain complex of which the amino acid or peptide was added to its C-terminus is preferably between about 8.3 and about 8.9, and more preferably, between about 8.4 and about 8.8.

Examples of the most preferable embodiments of the PD-1/CD19 bispecific antibody of the present invention include the clones CD19-1(Bi), CD19-2(Bi), CD19-3(Bi), CD19-4(Bi) and CD19-5(Bi) generated by the manner described in Example 12 of the present specification, as well as the clone CD19-6(Bi) generated by the manner described in Example 13.

Examples of preferable features of the PD-1/CD19 bispecific antibody of the present invention include allowing the interaction between PD-1 and PD-L1, interaction between PD-1 and PD-L2 or both of interactions thereof. Herein, the sentence "allowing the interaction between PD-1 and PD-L1, interaction between PD-1 and PD-L2 or both of interactions thereof" means the same as described in descriptions regarding the "first arm specifically binding to PD-1".

Further, examples of preferable features of the PD-1/CD19 bispecific antibody of the present invention include sufficiently reducing cytokine production. Herein, the sentence "sufficiently reducing cytokine production" means that, for example, during intravenous administration or by 24 hours after that administration, by drip infusion of the PD-1/CD19 bispecific antibody of the present invention, for example, concentration of cytokine including IL-2, IFN-γ and/or TNF-α in blood or tissue do not increase, or even if it increases, it is such a degree that it can be suppressed by steroid administration.

Further, examples of preferable features of the PD-1/CD19 bispecific antibody of the present invention include the suppressive effect against T cells (e.g., memory T cells) activation. The suppressive effect can be evaluated as the suppressive effect against cytokine (e.g., IL-2) production.
Method for Manufacturing and Purifying the PD-1/CD19 Bispecific Antibody The PD-1/CD19 bispecific antibody and antibody fragment thereof of the present invention can also be manufactured by the method disclosed in WO2014/051433, WO2013/157953 or WO2013/157954.

Specifically, the PD-1/CD19 bispecific antibody and antibody fragment thereof of the present invention can be manufactured by gene-transferring an expression vector in which (1) a polynucleotide encoding the heavy chain having the VH of the first arm specifically binding to PD-1, (2) a polynucleotide encoding the heavy chain having the VH of the second arm specifically binding to CD19, and (3) a polynucleotide encoding the common light chain have been inserted, respectively, into mammalian animal cells to transform them, and then by having them express and secret both of the heavy chain and the common light chain.

Herein, any host cells for expressing the PD-1/CD19 bispecific antibody of the present invention can be used as long as they can be gene-transferred by expression vectors to express them. Preferable examples of host cells include insect cells such as SF-9 and SF-21, more preferably, mammalian cells such as mouse cells including CHO cells, BHK cells, SP2/0 cells and NS-0 myeloma cells, primate cells such as COS and Vero cells and MDCK cells, BRL 3A cells, hybridoma, tumor cells, immortalized primary cells, W138, HepG2, HeLa, HEK293, HT1080 and embryonic retina cells such as PER.C6, and the like. Note here that in selection of the expression system, expression vectors for mammalian cells and host cells therefor may be used such that antibodies are appropriately glycosylated. Human cell lines, preferably, PER.C6 are advantageously used to obtain antibodies corresponding to glycosylated patterns for human.

Protein production in host cells transformed by gene-transferring the expression vectors can be carried out with reference to, for example, Current Protocols in Protein Science (1995), Coligan J E, Dunn B M, Ploegh H L, Speicher D W, Wingfield P T, ISBN 0-471-11184-8, Bendig, 1988. Furthermore, general guidelines, procedures and practical methods to maximize the productivity of host cell culture can be carried out with reference to Mammalian Cell Biotechnology: a Practical Approach (M. Butler, ed., IRL Press, 1991). Expression of antibodies in host cells is described in, for example, publications such as EP0120694, EP0314161, EP0481790, EP0523949, U.S. Pat. No. 4,816, 567, WO2000/63403 and the like.

Herein, culture conditions for host cells can be optimized by well-known methods, and the amount of protein production therein can be optimized. The culture can be carried out by batch culture, feeding culture, continuous culture or hollow-fiber culture in a petri dish, roller bottle or reaction chamber. In order to produce recombinant protein by cell culture in a large-scale and continuously, it is preferable to allow cells to proliferate in suspension. Furthermore, it is preferable to culture cells under a condition without any animal- or human-derived serum or animal- or human-derived serum components.

Antibodies expressed in host cells and recovered from them or culture thereof by well-known methods can be purified using well-known methods. Examples of purification methods include immunoprecipitation method, centrifugation method, filtration, size-exclusion chromatography, affinity chromatography, cation and/or anion exchange chromatography, hydrophobic interaction chromatography and the like. Furthermore, protein A or protein G affinity chromatography may be preferably used (see, e.g., U.S. Pat. Nos. 4,801,687 and 5,151,504).
Anti-CD19 Monoclonal Antibody The present invention includes a "monoclonal antibody specifically binding to CD19" (hereinafter, may be abbreviated as an "anti-CD19 monoclonal antibody") and an antibody fragment thereof to construct the PD-1/CD19 bispecific antibody of the present invention.

One embodiment of the anti-CD19 monoclonal antibody of the present invention is a monoclonal antibody capable of specifically binding to CD19 by association of a VH thereof with the VL of common light chain of the present invention. Herein, the sentence "specifically binding to CD19" is used as a feature of directly binding to CD19 with higher binding activity (dissociation constant (Kd value)) than at least $1\times10^{-5}$ M, preferably $1\times10^{-7}$ M, and more preferably $1\times10^{-9}$ M affinity, and does not substantially bind to any other proteins. Herein, the "antibody" in the "monoclonal antibody specifically binding to CD19" means a full-length antibody consisting of two heavy chains and two light chains linked with disulfide bonds. Furthermore, a "fragment of the monoclonal antibody specifically binding to CD19" is a part of the full-length antibody, including at least an antigen binding part, and examples thereof include Fab, Fab', Fv, scFv, F(ab')2 and the like.

Examples of the anti-CD19 monoclonal antibodies of the present invention include those having any one of the VH selected from the above-mentioned (1d) to (5d) constituting the VH of the "second arm specifically binding to CD19" or the VH comprising the amino acid sequence set forth in any one selected from SEQ ID Nos. 30 to 34 and the VL as the common light chain of the present specification (preferably, the VL comprising the amino acid sequence set forth in SEQ ID No. 25).

Further, examples of the anti-CD19 monoclonal antibodies of the present invention also include those in which one to five arbitrary amino acid residues are substituted with other amino acids (preferably, conservative amino acids thereof) in the respective CDRs of any one of the VH selected from the above-mentioned (1d) to (5d), and which have substantially the same binding activity to CD19 as that of the anti-CD19 monoclonal antibody having the original VH without any substitutions with the same amino acids. Examples thereof include those in which one amino acid residue in the CDR1 was substituted with other amino acids (preferably, conservative amino acids thereof) and one to five amino acid residues in the CDR2 or CDR3 were substituted with other amino acids (preferably, conservative amino acids thereof), respectively. Further, as shown in FIG. 5, in the respective CDRs of the anti-CD19 monoclonal antibody clones, amino acids different among the clones or any combination of a plurality thereof can be exchangeable each other among the clones. Herein, the sentence "which have substantially the same binding activity to CD19 as that of the anti-CD19 monoclonal antibody having the original VH without any substitutions with the same amino acids" means that the binding activity to CD19 of the anti-CD19 monoclonal antibody substituted with same amino acids is 95% or more, preferably 98% or more, and more preferably 99% or more to that of the anti-CD19 monoclonal antibody having the original VH without any substitutions with the same amino acids.

Furthermore, examples of the anti-CD19 monoclonal antibodies of the present invention include those which contain the respective CDRs comprising the above-mentioned specific amino acid sequence, and in which the amino acid sequences of the framework regions are encoded by a specific germ-line gene or gene thereof with somatic mutation(s). Examples thereof include a specific VH encoded by the specific germ-line gene or gene thereof with somatic mutation(s), described in the description regarding the above-mentioned "second arm specifically binding to CD19."

Furthermore, in the anti-CD19 monoclonal antibodies of the present invention, examples of those which contain the respective CDRs in any one of the VH selected from the above-mentioned (1d) to (5d), and in which the FR amino acid sequences thereof are encoded by a specific germ-line gene or gene thereof with somatic mutation(s) include those having the VH comprising the amino acid sequence set forth in any one selected from SEQ ID Nos. 30 to 34. Furthermore, examples of such anti-CD19 monoclonal antibodies include those having a VH amino acid sequence having at least 80%, preferably at least 90%, more preferably at least 95%, further preferably at least 98%, furthermore preferably at least 99% identity to the amino acid sequence set forth in any one selected from SEQ ID Nos. 30 to 34, and having the binding activity to CD19 which is substantially the same as that of the anti-CD19 monoclonal antibody having the original VH. Herein, the sentence "having the binding activity to CD19 that is substantially the same as that of the anti-CD19 monoclonal antibody having the original VH" means that it has 95% or more, preferably 98% or more, and more preferably 99% or more of the binding activity to CD19 to that of the anti-CD19 monoclonal antibody having the original VH.

Furthermore, other examples of the anti-CD19 monoclonal antibodies of the present invention also include (1) an anti-CD19 monoclonal antibody cross-competing for the binding to CD19 with an anti-CD19 monoclonal antibody having any one of the VH selected from the above-mentioned (1d) to (5d) or the VH comprising the amino acid sequence set forth in any one selected from SEQ ID Nos. 30 to 34, and the VL of the common light chain of the present specification (preferably, the VL comprising the amino acid sequence set forth in SEQ ID No. 25), and (2) an anti-CD19 monoclonal antibody with which the binding to CD19 is cross-competed by an anti-CD19 monoclonal antibody having any one of the VH selected from the above-mentioned (1d) to (5d) or the VH comprising the amino acid sequence set forth in any one selected from SEQ ID Nos. 30 to 34 and the same VL of the common light chain.

Furthermore, other examples of the anti-CD19 monoclonal antibodies of the present invention also include those having the VH comprising the amino acid sequence in which glutamine at position 114 in the amino acid sequence set forth in any one selected from SEQ ID No. 30 to 34 was or may be substituted with arginine, and the VL of the common light chain of the present specification (preferably, the VL comprising the amino acid sequence set forth in SEQ ID No. 25), and they are more preferably those having the VH comprising the amino acid sequence in which glutamine at position 114 in the amino acid sequence set forth in any one selected from SEQ ID No. 30 to 34 was substituted with arginine and the VL of the same common light chain, which correspond to the anti-CD19 monoclonal antibodies having the VH comprising any one of the amino acid sequence selected from SEQ ID No. 62 to 66 and the same VL of the common light chain, respectively.

Polynucleotide Encoding the PD-1/CD19 Bispecific Antibody

A polynucleotide encoding the PD-1/CD19 bispecific antibody comprises (1) a polynucleotide encoding the heavy chain having the VH of the first arm specifically binding to PD-1, (2) a polynucleotide encoding the heavy chain having the VH of the second arm specifically binding to CD19, and (3) polynucleotides encoding common light chains. Herein, the polynucleotide encoding the heavy chain having the VH of the first arm specifically binding to PD-1 comprises a polynucleotide encoding the VH of the first arm specifically binding to PD-1 and a polynucleotide encoding the constant region of the heavy chain having the same VH. Similarly, a polynucleotide encoding the heavy chain having the VH of the second arm specifically binding to CD19 comprises a polynucleotide encoding the VH of the second arm specifically binding to CD19 and a polynucleotide encoding the constant region of the heavy chain having the same VH.

The polynucleotide encoding the PD-1/CD19 bispecific antibody may be any polynucleotides as long as they encode parts constituting the PD-1/CD19 bispecific antibody, respectively, and may be any of genome DNA, cDNA, synthesis DNA, RNA and DNA-RNA hybrid. As codons encoding one amino acid, one to six types are known. For example, Phe corresponds to TTT or TTC, Leu corresponds to TTA, TTG, CTT, CTC, CTA or CTG, Ile corresponds to ATT, ATC or ATA, Met correspond to ATG, Val corresponds to GTT, GTC, GTA or GTG, Ser corresponds to TCT, TCC, TCA or TCG, Pro corresponds to CCT, CCC, CCA or CCG, Thr corresponds to ACT, ACC, ACA or ACG, Ala corresponds to GCT, GCC, GCA or GCG, Tyr corresponds to TAT or TAC, His corresponds to CAT or CAC, Gln corresponds to CAA or CAG, Asn corresponds to AAT or AAC, Lys corresponds to AAA or AAG, Asp corresponds to GAT or GAC, Glu corresponds to GAA or GAG, Cys corresponds to TGT or TGC, Trp corresponds to TGG, Arg corresponds to CGT, CGC, CGA or CGG, Ser corresponds to AGT or AGC, Arg corresponds to AGA or AGG, and Gly corresponds to GGT, GGC, GGA or GGG, respectively. Accordingly, examples of the polynucleotides encoding the PD-1/CD19 bispecific antibody include a polynucleotide constituted by which each codon corresponding to each amino acid was arbitrarily combined. Preferable examples of the polynucleotide encoding the VH of the first arm specifically binding to PD-1 include the polynucleotide comprising the base sequence set forth in any one selected from SEQ ID Nos. 50 to 54 encoding the VHs of the clones PD1-1 to PD1-5, respectively. Preferable examples of the polynucleotide encoding the VH of the second arm specifically binding to CD19 include a polynucleotide comprising the base sequence set forth in any one selected from SEQ ID Nos. 56 to 60 and SEQ ID Nos. 76 to 80 coding the VHs of the clones CD19-5, CD19-1, CD19-4, CD19-2 and CD19-3, respectively. Furthermore, examples of the polynucleotide encoding the variable region of the common light chain include the polypeptide comprising the base sequence set forth in SEQ ID No. 55.

Pharmaceutical Use

The PD-1/CD19 bispecific antibody and the like of the present invention is useful for preventing, suppressing the progression of symptoms of, suppressing the recurrence of, and/or treating autoimmune diseases or graft-versus-host diseases (GVHD).

Examples of autoimmune diseases which can be prevented, of which the progression of symptoms can be suppressed and/or which can be treated with the PD-1/CD19 bispecific antibody or the like of the present invention include Behcet's disease, systemic lupus erythematosus, chronic discoid lupus erythematosus, multiple sclerosis (systemic scleroderma and progressive systemic sclerosis), scleroderma, polymyositis, dermatomyositis, periarteritis nodosa (polyarteritis nodosa and microscopic polyangiitis), aortitis syndrome (Takayasu's arteritis), malignant rheumatoid arthritis, rheumatoid arthritis, juvenile idiopathic arthritis, spondyloarthritis, mixed connective tissue disease, Sjogren's syndrome, adult Still's disease, vasculitis, allergic granulomatous vasculitis, hypersensitivity vasculitis, rheumatoid vasculitis, large vessel vasculitis, ANCA associated vasculitis (e.g., granulomatosis with polyangiitis and eosinophilic granulomatosis with polyangiitis), Cogan's syndrome, RS3PE syndrome, temporal arteritis, polymyalgia rheumatica, fibromyalgia, antiphospholipid antibody syndrome, eosinophilic fasciitis, IgG$_4$-related disease (e.g., primary sclerosing cholangitis and autoimmune insulitis, etc.), Guillain-Barre syndrome, myasthenia gravis, chronic atrophic gastritis, autoimmune hepatitis, non-alcoholic steatohepatitis, primary biliary cirrhosis, Goodpasture's syndrome, rapidly progressive glomerulonephritis, megaloblastic anemia, autoimmune hemolytic anemia, pernicious anemia, autoimmune neutropenia, idiopathic thrombocytopenic purpura, Basedow disease (Graves' disease (hyperthyroidism)), Hashimoto disease, autoimmune adrenal insufficiency, primary hypothyroidism, Addison's disease (chronic hypoadrenocorticism), idiopathic Addison's disease, type I diabetes mellitus, slowly progressive type I diabetes mellitus (latent autoimmune diabetes in adult), focal scleroderma, psoriasis, psoriatic arthritis, bullous pemphigoid, pemphigus, pemphigoid, gestational herpes, linear IgA bullous dermatosis, acquired epidermolysis bullosa, alopecia areata, vitiligo, vitiligo vulgaris, neuromyelitis optica, chronic inflammatory demyelinating polyneuropathy, multifocal motor neuropathy, sarcoidosis, giant cell arteritis, amyotrophic lateral sclerosis, Harada disease, autoimmune optic neuropathy, idiopathic azoospermia, habitual abortion, inflammatory bowel disease (e.g., ulcerous colitis and Crohn's disease), celiac disease, ankylosing spondylitis, severe asthma, chronic urticaria, transplantation immunity, familial mediterranean fever, eosinophilic chronic rhinosinusitis, dilated cardiomyopathy, systemic mastocytosis, inclusion body myositis and the like.

In the present invention, the term "treating" means cure or improvement of certain disease or symptom thereof. The term "preventing" means that the onset of certain disease or symptom thereof is prevented or delayed for a certain period of time. The term "suppressing the progression of symptoms" means that the progress or aggravation of symptoms is suppressed to stop the progress of disease conditions. The meaning of "preventing" also includes suppressing the recurrence. The term "suppressing the recurrence" means that the recurrence of certain disease or syndrome thereof is prevented or a possibility of recurrence is reduced.

Furthermore, another embodiment of the PD-1/CD19 bispecific antibody and the like of the present invention is useful for preventing, suppressing the progression of symptoms of, suppressing the recurrence of and/or treating autoreactive B cell-mediated diseases. Examples of autoreactive B cell-mediated diseases include systemic lupus erythematosus, Graves' disease, myasthenia gravis, autoimmune hemolytic anemia, autoimmune thrombocytopenia, asthma, cryoglobulinemia, primary biliary sclerosis, pernicious anemia and the like. In the same pharmaceutical use, the PD-1/CD19 bispecific antibody or the like of the present invention acts via suppressive effects against autoreactive B cells. Herein, examples of the suppressive effects against autoreactive B cells include the suppressive effects against the production of immune globulin such as IgG and IgM. Furthermore, the PD-1/CD19 bispecific antibody or the like of the present invention has the suppressive effects against memory T cells activation. Herein, examples of the suppressive effects against memory T cells activation include the suppressive effects against cytokine production.

The PD-1/CD19 bispecific antibody or the like of the present invention is usually administered systemically or locally through parenteral administration. Specific examples of such administration methods include injection administration, intranasal administration, transpulmonary administration, percutaneous administration and the like. Examples of injection administration include intravenous injection, intramuscular injection, intraperitoneal injection and the like. For intravenous injection, drip intravenous infusion is preferable. The dose thereof varies depending on the age, body weight, symptoms, therapeutic effect, administration method, treating period and the like. The single dose thereof for an adult patient is usually within a range of 0.1 μg/kg to 300 mg/kg, particularly preferably, within a range of 0.1 mg/kg to 10 mg/kg, once to several times per day by parenteral administration, or within a range of 30 minutes to 24 hours per day by intravenous sustaining administration. Needless to say, as mentioned above, since the dose varies depending on various conditions, it may be lower than the above-mentioned dose, or may be needed to be more than the above.

Formulation

When the PD-1/CD19 bispecific antibody or the like of the present invention is formulated to be used as an injection or infusion solution for drip infusion, the injection or infusion solution may be in any form of an aqueous solution, suspension or emulsion, or may be formulated as a solid agent along with pharmaceutically acceptable carrier such that it will be dissolved, suspended or emulsified in adding a solvent at the time of use. Examples of solvents which can be used in the injection or the infusion solution for drip infusion include distilled water for injection, physiological saline, glucose solution and isotonic solution and the like (e.g., solutions in which sodium chloride, potassium chloride, glycerin, mannitol, sorbitol, boric acid, borax, propylene glycol or the like is dissolved.).

Herein, examples of the pharmaceutically acceptable carriers include a stabilizer, solubilizer suspending agent, emulsifier, soothing agent, buffering agent, preservative, antiseptic agent, pH adjuster, antioxidant and the like. As a stabilizer, for example, various amino acids, albumin, globulin, gelatin, mannitol, glucose, dextran, ethylene glycol, propylene glycol, polyethylene glycol, ascorbic acid, sodium bisulfite, sodium thiosulfate, sodium edetate, sodium citrate, dibutylhydroxytoluene or the like can be used. As a solubilizer, for example, alcohol (e.g., ethanol etc.), polyalcohol (e.g., propylene glycol and polyethylene glycol, etc.), nonionic surfactant (e.g., Polysorbate 20 (registered trademark), Polysorbate 80 (registered trademark) and HCO-50, etc.) or the like can be used. As a suspending agent, for example, glyceryl monostearate, aluminum monostearate, methyl cellulose, carboxymethyl cellulose, hydroxymethyl cellulose, sodium lauryl sulfate or the like can be used. As an emulsifier, for example, gum arabic, sodium alginate, tragacanth or the like can be used. As a soothing agent, for example, benzyl alcohol, chlorobutanol, sorbitol or the like can be used. As a buffering agent, for example, phosphate buffer, acetate buffer, borate buffer, carbonate buffer, citrate buffer, Tris buffer, glutamic acid buffer, epsilon aminocaproic acid buffer or the like can be used. As a preservative, for example, methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edeate, boric acid, borax or the like can be used. As an antiseptic agent, for example, benzalkonium chloride, parahydroxybenzoic acid, chlorobutanol or the like can be used. As a pH adjuster, for example, hydrochloric acid, sodium hydroxide, phosphoric acid, acetic acid or the like can be used. As an antioxidant, for example, (1) aqueous antioxidants such as ascorbic acid, cysteine hydrochloride, sodium bisulfate, sodium metabisulfite and sodium sulfite, (2) oil-soluble antioxidants such as ascorbyl palmitate, butylated hydroxy anisole, butylated hydroxy toluene, lecithin, propyl gallate and α-tocopherol, and (3) metal chelating agents such as citric acid, ethylenediaminetetraacetic acid, sorbitol, tartaric acid and phosphoric acid can be used.

The injection or infusion solution for drip infusion can be produced by performing sterilization in the final process, or sterilization by aseptic manipulation, for example, sterilization by filtration with a filter or the like and subsequently filling it to an aseptic container. The injection or infusion solution for drip infusion may be used by dissolving the vacuum dried or lyophilized aseptic powder (which may include a pharmaceutically acceptable carrier powder) in an appropriate solvent at the time of use.

Combination Use or Combination Formulation

Further, the PD-1/CD19 bispecific antibody and the like of the present invention may be used in combination with other agents which is used for preventing, suppressing the progression of symptoms of, suppressing the recurrence of and/or treating autoimmune disease. In the present invention, examples of administration forms in combinational use with other agents (combinational use) may include a form of combination formulation containing both of ingredients in one formulation and a form being administered in separate formulations. Such combinational uses can complement the effects on preventing, suppressing the progression of symptoms of, suppressing the recurrence of and/or treating by other agents, or can maintain or reduce the dose or frequency of administration of other agents. When separately administering the PD-1/CD19 bispecific antibody or the like of the present invention and other agents, they may be simultaneously administered for a certain period of time, and then only the PD-1/CD19 bispecific antibody or the like or other agents may be administered. Alternatively, the PD-1/CD19 bispecific antibody or the like of the present invention may be initially administered, and after completion of administration thereof, other agents may be administered. Other agents may be initially administered, and after completion of administration thereof, the PD-1/CD19 bispecific antibody or the like of the present invention may be administered. The respective administration methods may be the same as or different from each other. A kit containing a formulation containing the PD-1/CD19 bispecific antibody or the like of the present invention and a formulation containing other agents can also be provided. Herein, the doses of other agents can be appropriately selected based on the dose in clinical use. Further, other agents may be administered in combination of two or more kinds of arbitrary agents at an appropriate ratio. Furthermore, examples of other agents include not only those already known but also those newly discovered in the future.

For example, when the PD-1/CD19 bispecific antibody or the like of the present invention is applied for preventing, suppressing the progression of symptoms of or the recurrence of and/or treating type I diabetes mellitus, it may be used in combination with any one or more of agents selected from an insulin preparation (e.g., human insulin, insulin glargine, insulin lispro, insulin detemir and insulin aspart, etc.), sulfonylurea agent (e.g., glibenclamide, gliclazide and glimepiride, etc.), quick-acting insulin secretion promoter (e.g., nateglinide etc.), biguanide preparation (e.g., metformin etc.), insulin resistance improving agent (e.g., pioglitazone etc.), α-glucosidase inhibitor (e.g., acarbose and voglibose, etc.), diabetic neuropathy therapeutic agent (e.g., epalrestat, mexiletine and imidapril, etc.), GLP-1 analog preparation (e.g., liraglutide, exenatide and lixisenatide, etc.) and DPP-4 inhibitor (e.g., sitagliptin, vildagliptin and alogliptin, etc.) and the like.

Furthermore, for example, when the PD-1/CD19 bispecific antibody or the like of the present invention is applied for preventing, suppressing the progression of symptoms of or the recurrence of and/or treating multiple sclerosis, it may be used in combination with any one or more of agents selected from a steroid agent (e.g., cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamsinolone, triamsinolone acetate, triamsinolone acetonide, dexamethasone, dexamethasone acetate, dexamethasone sodium phosphate, dexamethasone palmitate, paramethasone acetate and betamethasone, etc.), interferon β-1a, interferon β-1b, glatiramer acetate, mitoxantrone, azathioprine, cyclophosphamide, cyclosporin, methotrexate, cladribine, adrenocorticotropic hormone (ACTH), corticotropin, mizoribine, tacrolimus, fingolimod, alemtuzumab and the like.

Furthermore, for example, when the PD-1/CD19 bispecific antibody or the like of the present invention is applied for preventing, suppressing the progression of symptoms of or the recurrence of and/or treating systemic lupus erythematosus, it may be used in combination with any one or more of agents selected from a steroid agent (e.g., steroid agents mentioned above), immunosuppressive agent (e.g., cyclosporin, tacrolimus, and fingolimod, etc.) and belimumab.

For example, when the PD-1/CD19 bispecific antibody or the like of the present invention is applied for preventing, suppressing the progression of symptoms of or the recurrence of and/or treating rheumatoid arthritis, it may be used in combination with any one or more of agents selected from a steroid agent (e.g., steroid agents mentioned above), anti-rheumatic agent (e.g., methotrexate, sulfasalazine, bucillamine, leflunomide, mizoribine and tacrolimus, etc.), anti-cytokine agent (e.g., infliximab, adalimumab, tocilizumab, etanercept, golimumab and certolizumab, etc.), abatacept and the like.

When being applied for preventing, suppressing the progression of symptoms of or the recurrence of and/or treating other autoimmune diseases, the PD-1/CD19 bispecific antibody or the like of the present invention may be used in combination with any one or more of the above-mentioned other agents.

The present invention will now be described in more detail by the following examples, but the scope of the present invention is not limited thereto. A person skilled in the art can make various changes and modifications, based on the description of the present invention, and such changes and modifications are also included in the present invention.

EXAMPLES

Example 1: Immunization of MeMo (Registered Trademark) Mice Using Recombinant Human PD-1-Fc Fusion Protein As a method for obtaining the first arm specifically binding to PD-1 of the present invention, a method for immunizing MeMo (registered trademark) mice (see WO2009/157771) with a recombinant human PD-1 protein was selected. The MeMo (registered trademark) mice are those genetically modified such that a gene fragment containing a non-recombinant human heavy chain V gene region, D gene region and J gene region, as well as the recombinant human κ light chain IgVκ1-39*01/IGJκ1*01 germ-line gene have been linked to a mouse constant region gene. By directly immunizing them with a target protein for antibody, antibodies composed of heavy chains and common light chains, with diversity, can be produced.

With recombinant human PD-1-Fc fusion protein (R&D Systems, serial number 1086-PD) emulsified using Gerbu adjuvant MM (Gerbu Biotechnik, serial number #3001), 12- to 16-week-old MeMo (registered trademark) mice were immunized at an interval of 14 days. On days 0, 14 and 28 after immunization, the recombinant human PD-1-Fc fusion protein was subcutaneously administered, and thereafter, the recombinant human PD-1-Fc fusion protein dissolved in PBS was administered subcutaneously. On days 21, 35, 56, 77 and 98 after immunization, the antibody titer in serum was evaluated by flow cytometry using human PD-1-forced expressed HEK293 T cell lines. When human PD-1-forced expressed HEK293T cell lines were stained in 1000-fold diluted serum, mouse lymph tissues of which the MFI value increased more than three times higher compared to that of human PD-1 non-expressing HEK293T cell lines as a control were used for constructing a phage display library. Mice meeting the criteria for constructing the library were additionally immunized with the recombinant PD-1-Fc fusion protein for three days from the evaluation date of the antibody titer, and of which the spleens and inguinal lymph nodes were collected. Spleens and radial lymph nodes were also collected from mice in which the antibody titer in serum to human PD-1 and cynomolgus monkey PD-1 was 1/100 or more, and the antibody titer did not increase by additional immunization. RNA was extracted from those lymphoid tissues, and then cDNA synthesis was carried out.

Example 2: Construction of Phage Display Library to Obtain Anti-PD-1 Antibody (Protein Immunization)

Using the DNA prepared in Example 1 and primers specific to immunoglobulin heavy chain variable region family, PCR reaction was carried out. The obtained PCR products were digested with restriction enzymes SfiI and XhoI, and inserted into phagemid vector [having the gene (human κ light chain IgVκ1-39*01/IGJκ1*01 germ-line gene) encoding the common light chain] digested with the same restriction enzymes to construct the library.

Example 3: Screening for Anti-PD-1 Antibody

Using plates coated with human PD-1-Fc fusion protein, human PD-1-His tag fusion protein, cynomolgus monkey PD-1-His tag fusion protein or mouse PD-1-His tag fusion protein, phage selection based on the binding property to PD-1 was carried out. When using human PD-1-Fc fusion protein, during incubation with phage, human IgG (SIGMA, serial number 14506) was added thereto to absorb Fc reactive clones. Binding phages capable of binding to human PD-1, cynomolgus monkey PD-1 and mouse PD-1 were enriched. Using selections on cynomolgus monkey PD-1-forced expressing HEK293 T cell lines, phages capable of binding to cynomolgus monkey PD-1 were enriched. *Escherichia coli* strain TG1 clones transformed with phages obtained by selection were obtained to produce a master plate.

Further, based on the binding property to PD-1 on a plate to which human PD-1-Fc fusion protein was adsorbed, the phage selection from periplasmic space extracts of the clones obtained by the above-mentioned selection was carried out. Note here that as the criteria for selection, clones with signals three times more than signal (OD$_{450}$ value) in a negative control well (PBS) were defined as positive clones.

Example 4: DNA Sequencing Candidate Clones for Anti-PD-1 Antibodies

DNA sequencing for heavy chain variable region genes of positive clones obtained by screening in Example 3 was carried out. Analyzed DNA sequences were classified into super clusters (a group having the same-length of the heavy chain CDR3, in which an amino acid sequence of the same CDR3 is 70% or more homologous each other) and clusters (a group in which the amino acid sequences of the heavy chain CDR3 are same). Hundreds clones were obtained, which were classified into super clusters and clusters.

Example 5: Screening Based on the Evaluation of the Binding Property to PD-1 Expressing Cells From the respective classified super clusters, anti-PD-1 monoclonal antibody clones meeting the following conditions were screened and isolated:
(1) having somatic mutations in CDRs with high frequency,
(2) having a germ-line gene of highly frequently used VH, and
(3) having a high signal in the screening based on the binding property to human PD-1-Fc fusion protein.

Using Fab fragments contained in those periplasmic space extracts, the binding properties to human PD-1-forced expressing CHO-S cell line and cynomolgus monkey PD-1-forced expressing CHO-S cell line were evaluated by detecting with anti-mouse IgG polyclonal antibodies. Among the evaluated 117 clones (105 types of clusters), in 22 clones including anti-PD-1 monoclonal antibody clones PD1-1, PD1-2, PD1-3 and PD1-4, the bindings to human PD-1 expressing CHO-S cell line were confirmed.

Example 6: Preparation of Amino Acid Substituted Products of Anti-PD-1 Monoclonal Antibody The clones PD1-1 and PD1-4 contain deamidation motifs (Asn-Gly) in the framework region 4 of heavy chain variable region thereof, respectively. In order to obtain a PD-1 arm with reduced risk of deamidation, a variant in which the deamidation motifs have been converted was produced. Asparagine (Asn) at position 119 according to the EU numbering system for the clone PD1-4 was altered to glutamine by a well-known site-specific mutation method, to prepare and isolate the clone PD1-5. The binding property to human PD-1-forced expressing CHO-S cells of that clone was equal to that of the clone PD1-4.

Example 7: Immunization to MeMo (Registered Trademark) Using CD19 Expressing Plasmid Vector As a method for obtaining the second arm specifically binding to CD19 of the present invention, a method for immunizing MeMo (registered trademark) mice (see WO2009/157771) with human CD19 expressing plasmid vectors and cynomolgus monkey CD19 expressing plasmid vectors was selected.

The MeMo (registered trademark) mice are those genetically modified such that a gene fragment containing a non-recombinant human heavy chain V gene region, D gene region, and J gene region and recombinant human κ light chain IgVκ1-39*01/IGJκ1*01 germ-line gene have been linked to a mouse constant region gene. By directly immunizing them with plasmid vectors expressing a target protein for antibody, antibodies composed of heavy chains and common light chains, with diversity, can be produced.

With human CD19 expressing plasmid vectors and/or cynomolgus monkey CD19 expressing plasmid vectors, 12- to 16-week-old MeMo (registered trademark) mice were immunized, respectively or alternately. On days 0, 3, 6, 14, 17, 28, 31, 42, 49, 63, and/or 70 after immunization, the expressing plasmid vectors were administered. The antibody titer in serum was evaluated by flow cytometry using human CD19 expressed cell lines. When the human CD19 expressed cell lines were stained in 100-fold diluted serum, mouse lymph tissues of which the MFI value increased more than three times higher than that of human CD19 non-expressing cell lines as a control were used to construct a phage display library. Mice meeting the criteria for constructing the library construct were additionally immunized, and of which spleens and inguinal lymph nodes were collected. RNA was extracted from those lymphoid tissues, and then cDNA synthesis was carried out by reverse transcription reaction using primers specific to IgG constant region.

Example 8: Construction of Phage Display Library to Obtain Anti-CD19 Antibody Using the DNA prepared in Example 7 and primers specific to immunoglobulin heavy chain variable region family, PCR reaction was carried out. The obtained PCR products were digested with restriction enzymes, and inserted into phagemid vector digested [having the gene (human κ light chain IgVκ1-39*01/IGJκ1*01 germ-line gene) encoding the common light chain] digested with the same restriction enzymes to construct the library.

Example 9: Screening for Anti-CD19 Antibody

Using human CD19-Fc fusion protein (R&D systems, Serial No. 9269-CD), cynomolgus monkey CD19-Fc fusion protein (NovoPro Bioscience, Serial No. 504385), human B cell lines Raji or cynomolgus monkey CD19-forced expressing HEK293T cell lines, phage selection based on the binding property to CD19 was carried out. *Escherichia coli* strain TG1 clones transformed with phages obtained by the selection were obtained to produce a master plate. Note here that as the criteria for the selection, clones with signals more than three times than signal (OD$_{450}$ value or MFI) obtained by a negative control were defined as positive clones.

Example 10: DNA Sequencing for Candidate Clones of Anti-CD19 Antibodies

DNA sequencing for the heavy chain variable region gene of positive clones obtained by screening in Example 9 was carried out. Analyzed DNA sequences were classified into super clusters (a group of which the length of heavy chain CDR3 is same and the amino acid sequence of heavy chain variable region is mutually 70% or more homologous) and clusters (a group of which the amino acid sequences of the heavy chain variable region and heavy chain CDR3 are mutually same, respectively).

At the first screening, hundreds clones were obtained, which were classified into super clusters, clusters and 4 types of germlines. At the second screening, hundreds clones were obtained, which were classified into super clusters, clusters and 8 types of germlines. 19 types of super clusters are different from those at the first screening.

Example 11: Screening Based on the Evaluation of the Binding Property to CD19

From the respective classified super clusters, anti-CD19 monoclonal antibody clones meeting the following conditions were screened and isolated:
(1) having somatic mutations in CDRs with high frequency,
(2) having a germ-line gene of highly frequently used VH, and
(3) having a high signal in the screening based on the binding property to CD19.

Using Fab fragments contained in these periplasmic space extracts, the binding property to CD19 was evaluated.

It was confirmed that among the evaluated clones, a number of clones including anti-CD19 monoclonal antibody clones CD19-1, CD19-2, CD19-3, CD19-4 and CD19-5 can bind to human CD19 expressing cell line.

Example 12: Preparation of the PD-1/CD19 Bispecific Antibody

Expression vectors expressing the respective heavy chains of the first arm specifically binding to PD-1 were prepared by linking DNAs encoding the respective heavy chain variable regions of anti-PD-1 monoclonal antibody clones PD1-1 to PD1-5 selected in Example 5 and 6, to DNAs encoding IgG$_1$ heavy chain constant region, respectively. On the other hand, expression vectors expressing the respective heavy chains of the second arm specifically binding to CD19 were prepared by linking DNAs encoding the respective heavy chain variable regions of anti-CD19 monoclonal antibody clones CD19-1 to CD19-5 selected in Example 11, to DNAs encoding IgG$_1$ heavy chain constant region, respectively. Herein, as genes expressing those heavy chain constant region, as to the first arm specifically binding to PD-1, a gene expressing Fc region having L351D/L368E variation (DE variation) was used, and as to the second arm specifically binding to CD19, a gene expressing Fc region having L351K/T366K variation (KK variation) was used. These expression vectors were constructed so as to further contain a gene encoding the IGVK1-39/JK1 common light chain such that it will be expressed together. Further, in order to eliminate the Fc effector activity, the genes expressing these heavy chain constant regions were modified so as to be expressed as those in which leucine at position 235 was substituted with glycine and further glycine at position 236 was substituted with arginine in the heavy chain constant region, and furthermore in order to avoid processing after translation, those modified so as to be expressed as those in which lysine at a position 447 at the C-terminus of the heavy chain constant region was deleted were used. Both of these expression vectors were gene-transferred into Free Style 293F cells to make them produce antibodies in culture supernatants. The culture supernatants were collected and then treated by protein A affinity chromatography, to purify the clones CD19-1(Bi), CD19-2(Bi), CD19-3(Bi), CD19-4(Bi) and CD19-5(Bi) as the PD-1/CD19 bispecific antibody of the present invention, respectively.

Note here that, in that having the second arms specifically binding to CD19 derived from anti-CD19 monoclonal antibody clones CD19-1, CD19-2, CD19-3, CD19-4 and CD19-5, used in preparation thereof, these PD-1/CD19 bispecific monoclonal antibody clones correspond to those anti-PD-1 monoclonal antibody clones, respectively. All of these PD-1/CD19 bispecific antibody clones have the first arm specifically binding to PD-1, derived from the clone PD1-5.

Example 13: Preparations of the Anti-CD19 Monoclonal Antibody Variants and PD-1/CD19 Bispecific Antibodies Thereof There is a possibility that the PD-1/CD19 bispecific antibody clones prepared in Example 12 cannot be sufficiently separated or purified from the first arm-heavy chain/light chain complexes, the second arm-heavy chain/light chain complexes and/or the respective homodimers consisting of them, as by-products. Therefore, for the purpose of improving the separation of the bispecific antibody from those by-products in purification by cation exchange chromatography, amino acid variants of the anti-CD19 monoclonal antibodies in which the isoelectric point increased were prepared.

A variant of which glutamine at position 114 in SEQ ID NO. 30 representing the VH amino acid sequence of the clone CD19-5 was substituted with arginine by a known site-directed mutagenesis method was produced. In the present invention, the variant was named as "CD19-6". The isoelectric points of antibodies were calculated using Genetyx (Genetics Inc.), software for analyzing gene and amino acid sequence.

Further, the respective variants having the forms in which glycine and the peptides represented by SEQ ID Nos. 67 to 70 were added to the C-terminus of the heavy chain having the VH of CD19-6 (hereinafter, collectively referred to as "CD19-6/C-terminal peptide adduct"), respectively, were prepared by a known genetic modification technique. In the present invention, the variant having the form in which the peptide represented by SEQ ID NO. 67 was added to the C-terminus of CD19-6 was named as "CD19-7".

According to the same method as in Example 12, the respective expression vectors described in the same Example into which the respective DNAs encoding the variants of these anti-CD19 monoclonal antibodies and a DNA encoding the clone PD1-5 have been inserted, respectively, were gene-transferred into Free Style 293F cells to make them produce antibodies in culture supernatant. The culture supernatants were collected and treated by protein A affinity chromatography to purify the bispecific antibodies of the present invention, derived from the respective variants prepared in this Example, respectively. Among these bispecific antibodies, the bispecific antibody clone derived from CD19-6 was named as "CD19-6 (Bi)", and the bispecific antibody clone derived from CD19-7 was named as "CD19-7 (Bi)".

Example 14: Purification and Separation of the PD-1/CD19 Bispecific Antibody and By-Products Thereof The success and failure in purification and separation from by-products which might be generated during the productions of the PD-1/CD19 bispecific antibodies prepared in Examples 12 and 13, respectively, was verified.

The culture supernatants containing the same bispecific antibodies collected in Examples 12 and 13, respectively, were separately processed by protein A affinity chromatography and size exclusion chromatography to purify the same bispecific antibodies, and the anti-PD-1 antibody and anti-CD19 antibody corresponding to by-products, respectively.

The solvents containing these respective purified antibodies were buffer-replaced by ultrafiltration so as to be at pH 6.0. The respective purified antibodies after buffer-replacement were applied to a cation exchange column TSKgel SP-STAT Column (Tosoh, Model No. 0021964) equilibrated with buffer A (pH 7.0). The respective purified antibodies bound to the column were eluted by salt gradient using buffer B (pH 7.0) containing 1 mol/L sodium chloride. The flow rate of mobile phase was 0.5 mL/min, and the elution was performed with a linear gradient from buffer A to buffer B. A ratio of Buffer B was set to 0% from 0 to 10 minutes after the beginning of applying the respective purified antibodies, and then linearly increased from 0 to 100%, from 10 to 40 minutes, and set to 100% from 40 to 50 minutes.

The retention times (minutes) in cation exchange chromatography of the clones CD19-2 (Isoelectric point: 8.32), CD19-6 (Ip: 8.49) and CD19-7 (Ip: 8.75) were 15.167, 15.749 and 17.521, respectively, and those of the clones CD19-6 and CD19-7 were elongated, respectively. On the other hand, the clones PD1-3 (Ip: 7.67) and PD1-5 (Ip: 7.52) were not bound to cation exchange column, and were eluted therefrom.

On the other hand, the PD-1/CD19 bispecific antibody clones CD19-2 (Bi) and CD19-2(Bi) were not bound to cation exchange column, and were eluted therefrom, but the retention times (minutes) of the clones CD19-6 (Bi) and CD19-7 (Bi) were 13.715 and 14.955, respectively.

As described above, by increasing the isoelectric point through a substitution of amino acid in the second arm or addition of specific peptide at the C-terminus of the heavy chain thereof, the separation of the bispecific antibody of the present invention as a target from anti-PD-1 antibody and anti-CD19 antibody as by-products in purification by cation exchange chromatography was improved, and thereby which made possible to provide the bispecific antibody of the present invention in which the contamination of by-products thereof was extremely reduced.

Example 15: Evaluation of the Binding Property of the PD-1/CD19 Bispecific Antibody By Biacore assay using human IgG1-Fc fused human PD-1 extracellular recombinant protein (R&D systems, Serial No. 1086-PD), the binding affinities to PD-1 recombinant protein of the first arm of the PD-1/CD19 bispecific monoclonal antibodies obtained in Examples 12 and 13 were evaluated, respectively. Note here that for immobilization of the recombinant proteins, Series S Sensor Chip CM5 Sensor Chip (GE Health Care, serial number 29-1049-88) was used.

Similarly, by Biacore assay using human IgG1-Fc fused CD19 extracellular recombinant protein (R&D systems, Serial No. 9269-CD), the binding affinities to CD19 of the second arm of the same antibodies were evaluated, respectively. FIG. 11 shows the binding affinities (Kd value) to PD-1 of the first arm and the binding affinities to CD19 of the second arm with respect to the respective clones. It was confirmed that the binding affinities to PD-1 and CD19 of CD19-6 (Bi) were improved, respectively, as compared with those of CD19-5 (Bi) without the amino acid substitution in Example 13.

Example 16: Verification of the Binding Property of the PD-1/CD19 Bispecific Antibody It was verified that the PD-1/CD19 bispecific antibodies obtained in Example 12 and 13 specifically bind to human PD-1, cynomolgus monkey PD-1, human CD19 and cynomolgus monkey CD19, respectively. The clones CD19-1(Bi) to CD19-6(Bi) were added to human PD-1-forced expressing CHO-S cell lines, cynomolgus monkey PD-1-forced expressing CHO-S cell lines, CHO-S cell lines, human CD19-forced expressing CHO-K1 cell lines, cynomolgus monkey CD19-forced expressing CHO-K1 cell lines and CHO-K1 cell lines, respectively, and which were incubated on ice for 20 minutes. After washing those cells, 100 µL of PE-labeled goat anti-human IgG-Fc F(ab')$_2$ fragment antibody (ThermoFisher, Serial No. H10104) was added thereto, and which were incubated on ice for 20 minutes. After washing those cells, the binding property to PD-1 of the first arm and the binding property to CD19 of the second arm of those antibodies were evaluated by flow cytometry, respectively. FIGS. 12 to 16 show results thereof in this assay.

All of the clones bind to human PD-1, cynomolgus monkey PD-1, human CD19 and cynomolgus monkey CD19. Note here that non-specific binding in this binding system was not detected.

It was verified that the PD-1/CD19 bispecific monoclonal antibodies obtained in Example 12 specifically bind to PD-1 and CD19 simultaneously, respectively. Initially, the clones CD19-1(Bi) to CD19-5(Bi) were added to human CD19-forced expressing CHO-K1 cell lines and CHO-K1 cell lines, respectively, and which were incubated on ice for 20 minutes. After those cells were washed, 100 µL of 6× His tag fused human PD-1 extracellular region recombinant protein (R&D systems, Serial No. 8986-PD) was added thereto, and which were incubated on ice for 20 minutes. After those cells were washed, 100 µL of Alexa Fluor 488-labeled mouse anti-His tag antibody (MBL, Serial No. D291-A48) was added thereto, and which were incubated on ice for 20 minutes. After those cells were washed, the binding amounts of the PD-1 extracellular region recombinant protein was evaluated by flow cytometry. FIG. 17 shows results thereof in this assay.

All of the clones bind to PD-1 and CD19, simultaneously. Note here that non-specific binding in this binding system was not detected.

Figure 18:
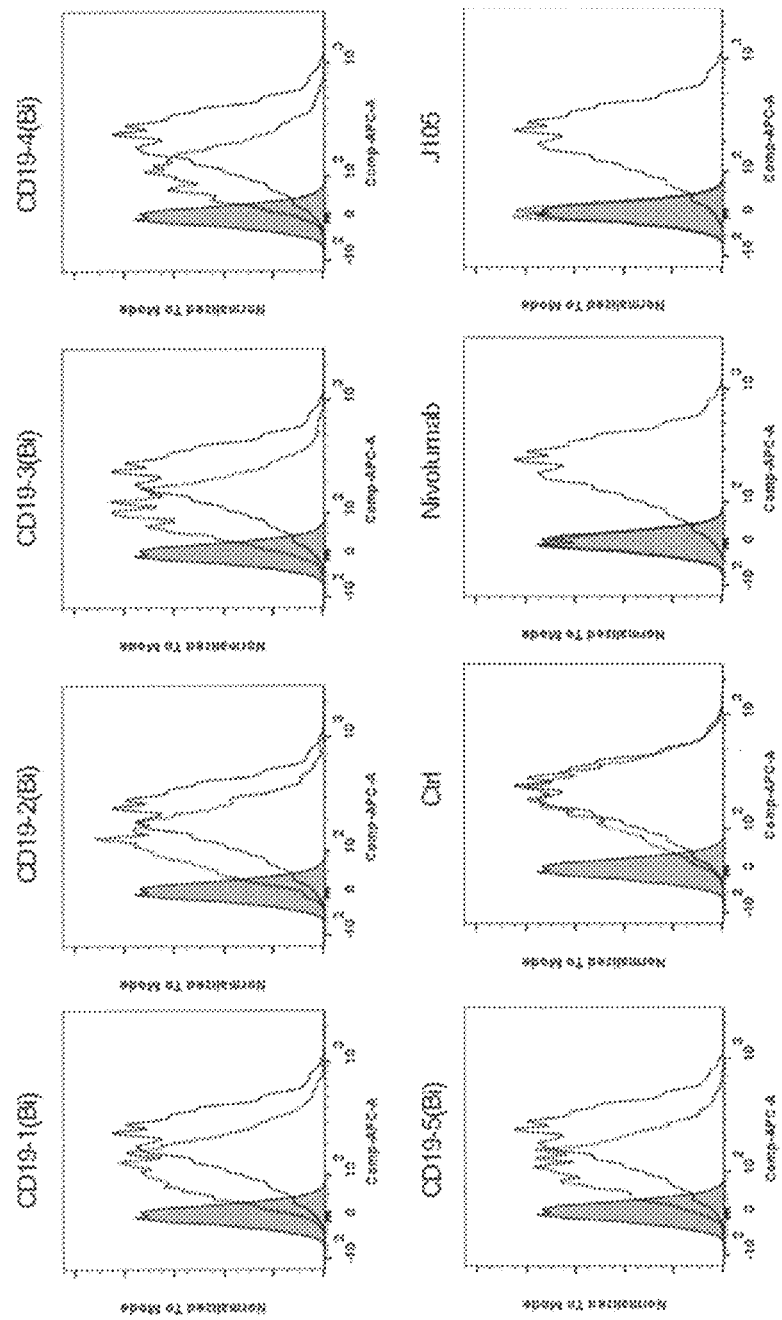
FIG. 18 It shows flow cytometry demonstrating influences on the PD-1/PD-L1 interaction of the respective PD-1/CD19 bispecific antibody clones, respectively.

Example 17: Evaluation of the Binding Property of the First Arm of the PD-1/CD19 Bispecific Antibody In order to evaluate effects on the PD-1/PD-L1 interaction of the first arms of the PD-1/CD19 bispecific antibodies obtained in Example 12, a competitive binding assay with respect to the binding to PD-1 of the same bispecific antibody clones and soluble PD-L1 recombinant proteins was carried out. Initially, the clones CD19-1(Bi) to CD19-5(Bi), Nivolumab and anti-human PD-1 antibody J105 (Immunology Letters, 2002, Vol. 83, Issue 3, p. 215-220) were added to human PD-1-forced expressing CHO-S cell lines on ice, respectively. Further, soluble PD-L1 recombinant proteins (R&D systems, Serial No. 156-B7) labeled with biotin using the kit for labeling biotin (Dojin, Serial No. LK03) was added thereto on ice. After those cells were washed, APC-labeled streptavidin (BioLegend, Serial No. 405207) was added thereto on ice. After those cells were washed, the binding amounts of soluble PD-L1 recombinant proteins was evaluated by flow cytometry. FIG. 18 shows results thereof in this assay.

The clones CD19-1(Bi) to CD19-5(Bi) allowed the binding of soluble PD-L1 recombinant protein to PD-1. On the other hand, Nivolumab and J105 completely inhibited the binding of soluble PD-L1 recombinant protein to PD-1 under the same condition.

It was demonstrated, by the same evaluation, that the bispecific antibodies having anti-PD-1 monoclonal antibody clones PD1-1 to PD1-4 obtained in Example 5, as the first arm, respectively, also allowed the binding of soluble PD-L1 recombinant protein to PD-1.

Figure 19:
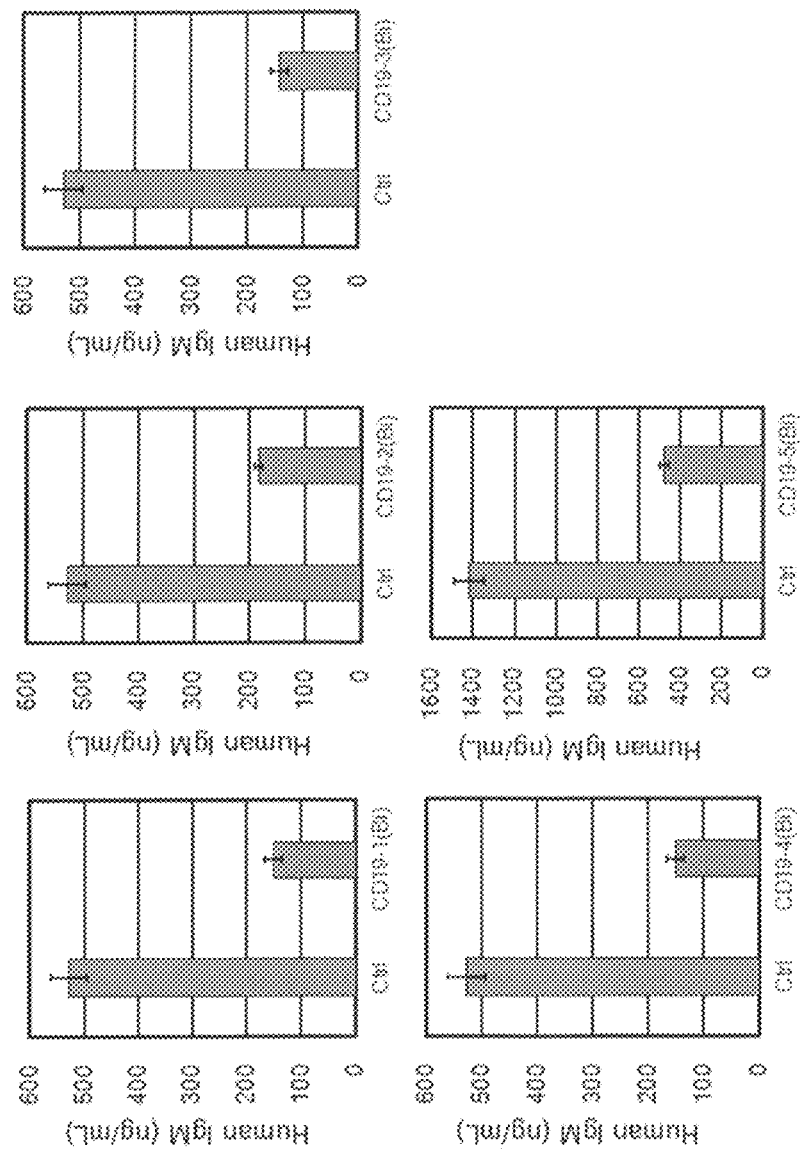
FIG. 19 It shows in vitro effects on IgM production from activated human B cells of the respective PD-1/CD19 bispecific antibody clones, respectively. Note here that in this figure, "Ctrl" represents control group.

Example 18: In Vitro Suppressive Effects of the PD-1/CD19 Bispecific Antibody Against Activated B Cells Suppressive effects against human IgM production were evaluated using B cells isolated from healthy human peripheral blood mononuclear cells (LONZA, model number CC-2702) by B Cell Isolation Kit II, human (Miltenyi Biotec, Serial No. 130-091-151). Human B cells were seeded in cell culture plates, and anti-human CD79B antibody (LifeSpan Biosciences, Serial No. LS-C134648), human CD40L recombinant protein (Enzo Life Sciences, Serial No. ALX-522-110) and human IL-21 recombinant protein (R&D systems, Serial No. 8879-IL) were added thereto, to perform activation treatment. The clones CD19-1(Bi) to CD19-5(Bi) or control antibody were added thereto, and IgM contained in the culture supernatant after activation treatment was quantified by ELISA (ThermoFisher, Serial No. BMS 2098). FIG. 19 shows results thereof. All of the clones CD19-1(Bi) to CD19-5(Bi) suppressed IgM production. Note here that an amount of IgM production (pg/mL) in the figure is represented as the mean value±standard error (N=4).

Figure 20:
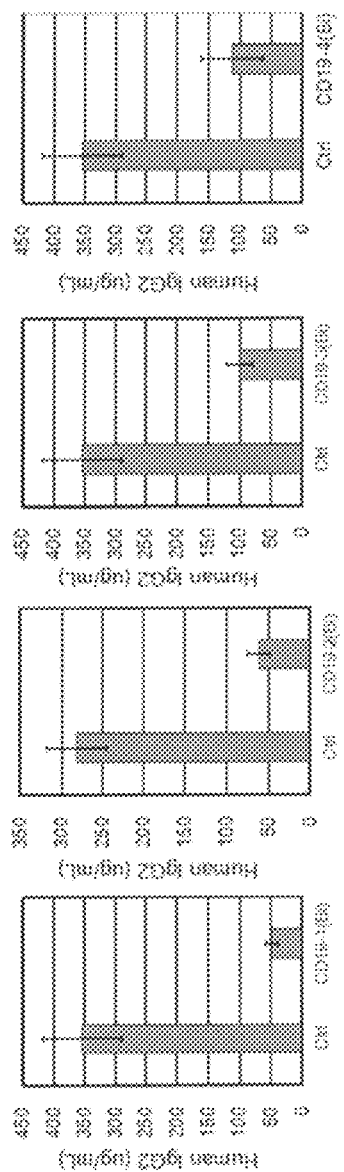
FIG. 20 It shows in vivo effects on $IgG_2$ production from activated human B cells of the respective PD-1/CD19 bispecific antibody clones CD19-1(Bi) to CD19-4(Bi), respectively. Note here that in this figure, "Ctrl" represents control group.
Figure 21:
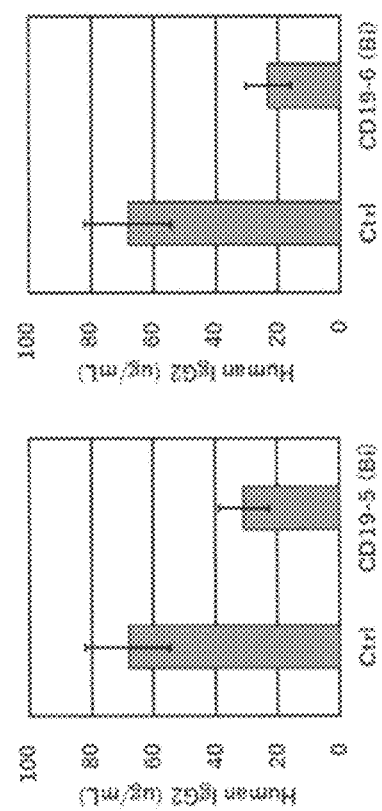
FIG. 21 It shows in vivo effects on $IgG_2$ production from activated human B cells of the PD-1/CD19 bispecific antibody clones CD19-5(Bi) and CD19-6(Bi), respectively. Note here that in this figure, "Ctrl" represents control group.

Example 19: In Vivo Suppressive Effects of the PD-1/CD19 Bispecific Antibody Against Activated B Cells Suppressive effects against human $IgG_2$ production were evaluated using NOD. Cg-Prkdcscidll2 rgtm1Wjl/SzJ mice (hereinafter, abbreviated as NSG mice.) into which peripheral blood mononuclear cells derived from healthy individuals (LONZA, Serial No. CC-2702) have been transplanted. $1 \times 10^7$ of peripheral blood mononuclear cells derived from healthy individuals were transplanted per a NSG mouse. On days 3, 7, 10, 14 and 17 after transplantation, 3 mg/kg/day of the clones CD19-1 (Bi) to CD19-4 (Bi) or control antibody were intraperitoneally administered once per day, respectively. Blood was collected from tail vein on day 21 after transplantation to prepare serum. On the other hand, the clones CD19-5(Bi) and CD19-6(Bi) were administered intraperitoneally on days 3, 7 and 10 after transplantation at the same dosage, respectively. At this time, a control antibody was intraperitoneally administered in parallel, as well. Blood was collected from tail vein on day 14 after transplantation to prepare serum. Human $IgG_2$ contained in serum was quantified by ELISA (ThermoFisher, Serial No. BMS 2093). FIGS. 20 and 21 show results thereof. All of the clones CD19-1(Bi) to CD19-4(Bi) suppressed $IgG_2$ production. Note here that an amount of $IgG_2$ production (µg/mL) in the figures is represented as the mean value±standard error (N=4-8).

Example 20: Evaluation of Cross-Competitive Property for the Binding to PD-1 of PD-1/CD19 Bispecific Antibody Cross-competition assay was conducted to evaluate the cross-competitive properties for the binding to PD-1 of the bispecific antibodies having the respective clones PD1-1 to PD1-5 as the first arm, which are the PD-1 antibodies used to produce PD-1/CD19 bispecific antibodies.

Initially, the bispecific antibody having the clone PD1-5 as the first arm was added to human PD-1-expressing CHO-S line cells on ice. Further, the biotin-labeled bispecific monoclonal antibodies having the clones PD1-1 to PD1-5 as the first arm, respectively, were added thereto, respectively, then which were incubated on ice. After those cells were washed, PE-labeled streptavidin (BD Pharmingen, Serial No. 554061) was added thereto, and which were incubated on ice. After washing those cells, the binding amounts of those biotin-labeled antibodies were measured using flow cytometry.

It was demonstrated that the bispecific antibody having the clone PD1-5 as the first arm can inhibit the bindings to PD-1 of the same antibodies having the clones PD1-1 to PD1-4 as the first arm, respectively, and thus it can cross-compete with those bindings to PD-1.

Example 21: Evaluation of In Vitro Effects of PD-1/CD19 Bispecific Antibody Against Cytokine Release from Human Peripheral Blood Mononuclear Cells For the purpose of analyzing the cytokine releasing activity of the PD-1/CD19 bispecific antibody, the experiment in which the bispecific antibody of the present invention or mouse anti-human CD3 antibody OKT3 (BioLegend, serial number 317304) are added to human peripheral blood mononuclear cells (hereinafter, referred to as "human PBMC") was carried out, respectively.

The clone CD19-6(Bi) and OKT3 were added to human PBMC (LONZA, serial number CC-2702), then which were cultured. IL-2 contained in culture supernatants was quantified by flow cytometry using Cytometric Bead Array (BD Biosciences, serial number 551809). FIG. 25 shows results thereof. Note here that an amount of IL-2 production (pg/mL) in the figure are represented by mean value±standard error (N=3).

OKT3 remarkably induced IL-2 production, but no IL-2 production with respect to CD19-6(Bi) was detected.

Example 22: Physicochemical Stability Evaluation of the PD-1/CD19 Bispecific Antibody It was confirmed that the PD-1/CD19 bispecific antibody of the present invention has good performance in any of the physicochemical stability evaluations including structural stability in differential scanning calorimetry (DSC) measurement, colloid stability in diffusion coefficient change (DLS) measurement and chemical stability (e.g., change in protein concentration, molecular structure change, the presence or absence of association/aggregation, the presence or absence of charge variant generation, structure change, binding activity to CD19) under stress conditions (e.g., at pH 3 to 4 and 5° C. or at pH 7, 5° C. and five freeze-thaw cycles).

INDUSTRIAL APPLICABILITY

The PD-1/CD19 bispecific antibody or antibody fragment thereof of the present invention is useful for preventing, suppressing the progression of symptoms of, suppressing the recurrence of, and/or treating autoimmune diseases or graft-versus-host diseases (GVHD).

The invention claimed is:

1. A bispecific antibody, having a first arm specifically binding to PD-1 and a second arm specifically binding to CD19, wherein
   (A) the first arm specifically binding to PD-1 has a heavy chain variable region (VH) comprising the amino acid sequence set forth in SEQ ID NO: 5, and a light chain variable region (VL) comprising the amino acid sequence set forth in SEQ ID NO: 25, and
   (B) the second arm specifically binding to CD19 has a VH comprising the amino acid sequence set forth in SEQ ID NO: 62, and a VL comprising the amino acid sequence set forth in SEQ ID NO: 25.

2. The bispecific antibody according to claim 1, which is an IgG$_1$ antibody.

3. The bispecific antibody according to claim 1, wherein the first arm specifically binding to PD-1 further comprises a heavy chain constant region comprising the amino acid sequence set forth in SEQ ID NO: 23.

4. The bispecific antibody according to claim 1, wherein the second arm specifically binding to CD19 further comprises a heavy chain constant region comprising the amino acid sequence set forth in SEQ ID NO: 24.

5. The bispecific antibody according to claim 1, wherein the first arm specifically binding to PD-1 and the second arm specifically binding to CD19 each further comprise a light chain constant region comprising the amino acid sequence set forth in SEQ ID NO: 29.

6. A bispecific antibody, having a first arm specifically binding to PD-1 and a second arm specifically binding to CD19,
wherein the bispecific antibody comprises
(A) a heavy chain having a heavy chain variable region (VH) of the first arm specifically binding to PD-1,
(B) a light chain having a light chain variable region (VL) of the first arm specifically binding to PD-1,
(C) a heavy chain having a VH of the second arm specifically binding to CD19, and
(D) a light chain having a VL of the second arm specifically binding to CD19; and
wherein
(a) a heavy chain having a VH of the first arm specifically binding to PD-1 has a VH comprising the amino acid sequence set forth in SEQ ID NO: 5, and a heavy chain constant region comprising the amino acid sequence set forth in SEQ ID NO: 23,
(b) a light chain having a VL of the first arm specifically binding to PD-1 has a VL comprising the amino acid sequence set forth in SEQ ID NO: 25, and a light chain constant region comprising the amino acid sequence set forth in SEQ ID NO: 29,
(c) a heavy chain having a VH of the second arm specifically binding to CD19 has a VH comprising the amino acid sequence set forth in SEQ ID NO: 62, and a heavy chain constant region comprising the amino acid sequence set forth in SEQ ID NO: 24, and
(d) a light chain having a VL of the second arm specifically binding to CD19 has a VL comprising the amino acid sequence set forth in SEQ ID NO: 25, and a light chain constant region comprising the amino acid sequence set forth in SEQ ID NO: 29.

* * * * *

SEQUENCE LISTING

<160> NUMBER OF SEQ ID NOS: 80

<210> SEQ ID NO 1
<211> LENGTH: 127
<212> TYPE: PRT
<213> ORGANISM: Homo sapiens

<400> SEQUENCE: 1

Gln Val Gln Leu Val Gln Ser Gly Ser Glu Leu Lys Gln Pro Gly Ala
1               5                   10                  15

Ser Val Lys Val Ser Cys Lys Ala Ser Gly Tyr Thr Phe Thr His Tyr
                20                  25                  30

Gly Leu His Trp Val Arg Gln Ala Pro Gly Gln Gly Leu Glu Trp Met
            35                  40                  45

Gly Trp Leu Asn Thr Asn Thr Glu Asn Pro Thr Phe Ala Gln Gly Phe
        50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Met Val Val Pro Thr Thr Ile Trp Asn Tyr Tyr His
            100                 105                 110

Phe Met Asp Val Trp Gly Asn Gly Thr Leu Val Thr Val Ser Ser
        115                 120                 125

<210> SEQ ID NO 2
<211> LENGTH: 127
<212> TYPE: PRT
<213> ORGANISM: Homo sapiens

<400> SEQUENCE: 2

Gln Val Gln Leu Val Gln Ser Gly Ser Glu Leu Lys Gln Pro Gly Val
1               5                   10                  15

Ser Val Lys Val Ser Cys Lys Ala Ser Gly Tyr Thr Phe Thr His Tyr
                20                  25                  30

Gly Leu His Trp Val Arg Gln Ala Pro Gly Gln Gly Leu Glu Trp Met
            35                  40                  45

Gly Trp Ile Asn Thr Asn Thr Gly Asn Pro Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Leu Val Val Pro Thr Thr Ile Trp Asn Tyr Tyr His
            100                 105                 110

Tyr Met Glu Val Trp Gly Lys Gly Thr Leu Val Thr Val Ser Ser
        115                 120                 125

<210> SEQ ID NO 3
<211> LENGTH: 127
<212> TYPE: PRT
<213> ORGANISM: Homo sapiens

<400> SEQUENCE: 3

Gln Val Gln Leu Val Gln Ser Gly Ser Glu Leu Lys Lys Pro Gly Ala
1               5                   10                  15

Ser Val Met Val Ser Cys Lys Ala Ser Gly Tyr Thr Phe Thr His Tyr
                20                  25                  30

```
Ala Leu His Trp Val Arg Gln Ala Pro Gly Gln Gly Leu Glu Trp Met
            35                  40                  45

Gly Trp Leu Asn Thr Asn Thr Glu Asn Pro Thr Tyr Ala Gln Gly Phe
        50                  55                  60

Thr Gly Arg Phe Val Phe Ser Leu Asp Thr Ser Val Thr Thr Ala Tyr
65                  70                  75                  80

Leu Gln Ile Asn Ser Leu Lys Ala Glu Asp Thr Ala Val Tyr Tyr Cys
                85                  90                  95

Ala Arg Gly Asp Met Val Val Pro Thr Thr Ile Trp Asn Tyr Tyr Tyr
            100                 105                 110

Tyr Met Asp Val Trp Gly Lys Gly Thr Thr Val Thr Val Ser Ser
            115                 120                 125
```

```
<210> SEQ ID NO 4
<211> LENGTH: 127
<212> TYPE: PRT
<213> ORGANISM: Homo sapiens

<400> SEQUENCE: 4

Gln Val Gln Leu Val Gln Ser Gly Ser Glu Leu Lys Gln Pro Gly Ala
1               5                   10                  15

Ser Val Lys Val Ser Cys Lys Ala Ser Gly Tyr Thr Phe Thr His Tyr
            20                  25                  30

Ala Leu His Trp Leu Arg Gln Ala Pro Gly Gln Gly Leu Glu Trp Met
            35                  40                  45

Gly Trp Leu Asn Thr Asn Thr Glu Asn Pro Thr Phe Ala Gln Gly Phe
        50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Met Val Val Pro Thr Thr Ile Trp Asn Tyr Tyr His
            100                 105                 110

Phe Met Asp Val Trp Gly Asn Gly Thr Thr Val Thr Val Ser Ser
            115                 120                 125
```

```
<210> SEQ ID NO 5
<211> LENGTH: 127
<212> TYPE: PRT
<213> ORGANISM: Homo sapiens

<400> SEQUENCE: 5

Gln Val Gln Leu Val Gln Ser Gly Ser Glu Leu Lys Gln Pro Gly Ala
1               5                   10                  15

Ser Val Lys Val Ser Cys Lys Ala Ser Gly Tyr Thr Phe Thr His Tyr
            20                  25                  30

Ala Leu His Trp Leu Arg Gln Ala Pro Gly Gln Gly Leu Glu Trp Met
            35                  40                  45

Gly Trp Leu Asn Thr Asn Thr Glu Asn Pro Thr Phe Ala Gln Gly Phe
        50                  55                  60

Thr Gly Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Asp Met Val Val Pro Thr Thr Ile Trp Asn Tyr Tyr His
            100                 105                 110
```

Phe Met Asp Val Trp Gly Gln Gly Thr Thr Val Thr Val Ser Ser
            115                 120                 125

<210> SEQ ID NO 6
<211> LENGTH: 5
<212> TYPE: PRT
<213> ORGANISM: Homo sapiens

<400> SEQUENCE: 6

His Tyr Gly Leu His
1               5

<210> SEQ ID NO 7
<211> LENGTH: 17
<212> TYPE: PRT
<213> ORGANISM: Homo sapiens

<400> SEQUENCE: 7

Trp Leu Asn Thr Asn Thr Glu Asn Pro Thr Phe Ala Gln Gly Phe Thr
1               5                   10                  15

Gly

<210> SEQ ID NO 8
<211> LENGTH: 18
<212> TYPE: PRT
<213> ORGANISM: Homo sapiens

<400> SEQUENCE: 8

Gly Asp Met Val Val Pro Thr Thr Ile Trp Asn Tyr Tyr His Phe Met
1               5                   10                  15

Asp Val

<210> SEQ ID NO 9
<211> LENGTH: 5
<212> TYPE: PRT
<213> ORGANISM: Homo sapiens

<400> SEQUENCE: 9

His Tyr Gly Leu His
1               5

<210> SEQ ID NO 10
<211> LENGTH: 17
<212> TYPE: PRT
<213> ORGANISM: Homo sapiens

<400> SEQUENCE: 10

Trp Ile Asn Thr Asn Thr Gly Asn Pro Thr Tyr Ala Gln Gly Phe Thr
1               5                   10                  15

Gly

<210> SEQ ID NO 11
<211> LENGTH: 18
<212> TYPE: PRT
<213> ORGANISM: Homo sapiens

<400> SEQUENCE: 11

Gly Asp Leu Val Val Pro Thr Thr Ile Trp Asn Tyr Tyr His Tyr Met
1               5                   10                  15

Glu Val

```
<210> SEQ ID NO 12
<211> LENGTH: 5
<212> TYPE: PRT
<213> ORGANISM: Homo sapiens

<400> SEQUENCE: 12

His Tyr Ala Leu His
1               5

<210> SEQ ID NO 13
<211> LENGTH: 17
<212> TYPE: PRT
<213> ORGANISM: Homo sapiens

<400> SEQUENCE: 13

Trp Leu Asn Thr Asn Thr Glu Asn Pro Thr Tyr Ala Gln Gly Phe Thr
1               5                   10                  15

Gly

<210> SEQ ID NO 14
<211> LENGTH: 18
<212> TYPE: PRT
<213> ORGANISM: Homo sapiens

<400> SEQUENCE: 14

Gly Asp Met Val Val Pro Thr Thr Ile Trp Asn Tyr Tyr Tyr Tyr Met
1               5                   10                  15

Asp Val

<210> SEQ ID NO 15
<211> LENGTH: 5
<212> TYPE: PRT
<213> ORGANISM: Homo sapiens

<400> SEQUENCE: 15

His Tyr Ala Leu His
1               5

<210> SEQ ID NO 16
<211> LENGTH: 17
<212> TYPE: PRT
<213> ORGANISM: Homo sapiens

<400> SEQUENCE: 16

Trp Leu Asn Thr Asn Thr Glu Asn Pro Thr Phe Ala Gln Gly Phe Thr
1               5                   10                  15

Gly

<210> SEQ ID NO 17
<211> LENGTH: 18
<212> TYPE: PRT
<213> ORGANISM: Homo sapiens

<400> SEQUENCE: 17

Gly Asp Met Val Val Pro Thr Thr Ile Trp Asn Tyr Tyr His Phe Met
1               5                   10                  15

Asp Val

<210> SEQ ID NO 18
<211> LENGTH: 5
<212> TYPE: PRT
<213> ORGANISM: Homo sapiens
```

```
<400> SEQUENCE: 18

His Tyr Ala Leu His
1               5

<210> SEQ ID NO 19
<211> LENGTH: 17
<212> TYPE: PRT
<213> ORGANISM: Homo sapiens

<400> SEQUENCE: 19

Trp Leu Asn Thr Asn Thr Glu Asn Pro Thr Phe Ala Gln Gly Phe Thr
1               5                   10                  15

Gly

<210> SEQ ID NO 20
<211> LENGTH: 18
<212> TYPE: PRT
<213> ORGANISM: Homo sapiens

<400> SEQUENCE: 20

Gly Asp Met Val Val Pro Thr Thr Ile Trp Asn Tyr Tyr His Phe Met
1               5                   10                  15

Asp Val

<210> SEQ ID NO 21
<211> LENGTH: 98
<212> TYPE: PRT
<213> ORGANISM: Homo sapiens

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 22
<211> LENGTH: 98
<212> TYPE: PRT
<213> ORGANISM: Homo sapiens

<400> SEQUENCE: 22

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60
```

```
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 23
<211> LENGTH: 329
<212> TYPE: PRT
<213> ORGANISM: Homo sapiens

<400> SEQUENCE: 23

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Asp Pro Pro Ser Arg Glu Glu
225                 230                 235                 240

Met Thr Lys Asn Gln Val Ser Leu Thr Cys Glu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 24
<211> LENGTH: 329
<212> TYPE: PRT
<213> ORGANISM: Homo sapiens

<400> SEQUENCE: 24

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Lys Pro Pro Ser Arg Glu Glu
225                 230                 235                 240

Met Thr Lys Asn Gln Val Ser Leu Lys Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 25
<211> LENGTH: 107
<212> TYPE: PRT
<213> ORGANISM: Homo sapiens

<400> SEQUENCE: 25

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
            85                  90                  95

Thr Phe Gly Gln Gly Thr Lys Val Glu Ile Lys
            100                 105

<210> SEQ ID NO 26
<211> LENGTH: 11
<212> TYPE: PRT
<213> ORGANISM: Homo sapiens

<400> SEQUENCE: 26

Arg Ala Ser Gln Ser Ile Ser Ser Tyr Leu Asn
1               5                   10

<210> SEQ ID NO 27
<211> LENGTH: 7
<212> TYPE: PRT
<213> ORGANISM: Homo sapiens

<400> SEQUENCE: 27

Ala Ala Ser Ser Leu Gln Ser
1               5

<210> SEQ ID NO 28
<211> LENGTH: 9
<212> TYPE: PRT
<213> ORGANISM: Homo sapiens

<400> SEQUENCE: 28

Gln Gln Ser Tyr Ser Thr Pro Pro Thr
1               5

<210> SEQ ID NO 29
<211> LENGTH: 107
<212> TYPE: PRT
<213> ORGANISM: Homo sapiens

<400> SEQUENCE: 29

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 30
<211> LENGTH: 122
<212> TYPE: PRT
<213> ORGANISM: Homo sapiens

<400> SEQUENCE: 30

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Lys Thr Ile Val Gly Val Met Thr Ala Phe Asp Ile Trp
            100                 105                 110

Gly Gln Gly Thr Met Val Thr Val Ser Ser
            115                 120

<210> SEQ ID NO 31
<211> LENGTH: 122
<212> TYPE: PRT
<213> ORGANISM: Homo sapiens

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Val Arg Gln Thr Ile Val Ala Thr Val Met Asn Ala Phe Asp Ile Trp
            100                 105                 110

Gly Gln Gly Thr Thr Val Thr Val Ser Ser
            115                 120

<210> SEQ ID NO 32
<211> LENGTH: 122
<212> TYPE: PRT
<213> ORGANISM: Homo sapiens

<400> SEQUENCE: 32

Gln Val Gln Leu Val Gln Ser Gly Ala Glu Val Lys Lys Ser Gly Glu
1               5                   10                  15

Ser Leu Lys Ile Ser Cys Lys Gly Ser Gly Phe Ser Phe Thr Ser Tyr
            20                  25                  30

Trp Ile Ala Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Phe Thr Thr Ala Tyr
65                  70                  75                  80

Leu Gln Trp Asn Ser Leu Lys Ala Ser Asp Thr Ala Ile Tyr Tyr Cys
                85                  90                  95

Ala Arg His Thr Ile Val Ala Thr Ile Tyr Asn Ala Phe Asp Phe Trp
            100                 105                 110

Gly Gln Gly Thr Met Val Thr Val Ser Ser
            115                 120

<210> SEQ ID NO 33
<211> LENGTH: 122
<212> TYPE: PRT
<213> ORGANISM: Homo sapiens

<400> SEQUENCE: 33

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ile Ser Tyr
            20                  25                  30

Trp Ile Gly Trp Val Arg Gln Met Pro Gly Lys Gly Leu Glu Trp Met
        35                  40                  45

Gly Ile Ile Trp Pro Gly Asp Ser Asp Thr Arg Tyr Ser Pro Ser Phe
    50                  55                  60

Gln Gly Gln Val Thr Ile Ser Ala Asp Lys Ser Ile Asn Val Ala Tyr
65                  70                  75                  80

Leu Gln Trp Ser Ser Leu Lys Ala Ser Asp Thr Ala Leu Tyr Tyr Cys
                85                  90                  95

Val Arg Gln Thr Ile Val Ala Thr Thr Gly Leu Ala Phe Asp Ile Trp
            100                 105                 110

Gly Gln Gly Thr Leu Val Thr Val Ser Ser
            115                 120

<210> SEQ ID NO 34
<211> LENGTH: 122
<212> TYPE: PRT
<213> ORGANISM: Homo sapiens

<400> SEQUENCE: 34

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Thr Ile Val Ala Thr Ile His Trp Ala Ser Asp Tyr Trp
            100                 105                 110

Gly Gln Gly Thr Met Val Thr Val Ser Ser
            115                 120

<210> SEQ ID NO 35
<211> LENGTH: 5
<212> TYPE: PRT
<213> ORGANISM: Homo sapiens

<400> SEQUENCE: 35

Ser Tyr Trp Ile Gly
1               5

<210> SEQ ID NO 36
<211> LENGTH: 17
<212> TYPE: PRT
<213> ORGANISM: Homo sapiens

<400> SEQUENCE: 36

Ile Ile Tyr Pro Gly Asp Ser Asp Thr Arg Tyr Ser Pro Ser Phe Gln
1               5                   10                  15

Gly

<210> SEQ ID NO 37
<211> LENGTH: 13
<212> TYPE: PRT
<213> ORGANISM: Homo sapiens

<400> SEQUENCE: 37

Lys Thr Ile Val Gly Val Val Met Thr Ala Phe Asp Ile
1               5                   10

<210> SEQ ID NO 38
<211> LENGTH: 5
<212> TYPE: PRT
<213> ORGANISM: Homo sapiens

<400> SEQUENCE: 38

Ser Tyr Trp Ile Gly
1               5

<210> SEQ ID NO 39
<211> LENGTH: 17
<212> TYPE: PRT
<213> ORGANISM: Homo sapiens

<400> SEQUENCE: 39

Ile Ile Tyr Pro Gly Asp Ser Asp Thr Arg Tyr Ser Pro Ser Phe Gln
1               5                   10                  15

Gly

<210> SEQ ID NO 40
<211> LENGTH: 13
<212> TYPE: PRT
<213> ORGANISM: Homo sapiens

<400> SEQUENCE: 40

Gln Thr Ile Val Ala Thr Val Met Asn Ala Phe Asp Ile
1               5                   10

<210> SEQ ID NO 41
<211> LENGTH: 5

```
<212> TYPE: PRT
<213> ORGANISM: Homo sapiens

<400> SEQUENCE: 41

Ser Tyr Trp Ile Ala
1               5

<210> SEQ ID NO 42
<211> LENGTH: 17
<212> TYPE: PRT
<213> ORGANISM: Homo sapiens

<400> SEQUENCE: 42

Ile Ile Tyr Pro Gly Asp Ser Asp Thr Arg Tyr Ser Pro Ser Phe Gln
1               5                   10                  15

Gly

<210> SEQ ID NO 43
<211> LENGTH: 13
<212> TYPE: PRT
<213> ORGANISM: Homo sapiens

<400> SEQUENCE: 43

His Thr Ile Val Ala Thr Ile Tyr Asn Ala Phe Asp Phe
1               5                   10

<210> SEQ ID NO 44
<211> LENGTH: 5
<212> TYPE: PRT
<213> ORGANISM: Homo sapiens

<400> SEQUENCE: 44

Ser Tyr Trp Ile Gly
1               5

<210> SEQ ID NO 45
<211> LENGTH: 17
<212> TYPE: PRT
<213> ORGANISM: Homo sapiens

<400> SEQUENCE: 45

Ile Ile Trp Pro Gly Asp Ser Asp Thr Arg Tyr Ser Pro Ser Phe Gln
1               5                   10                  15

Gly

<210> SEQ ID NO 46
<211> LENGTH: 13
<212> TYPE: PRT
<213> ORGANISM: Homo sapiens

<400> SEQUENCE: 46

Gln Thr Ile Val Ala Thr Thr Gly Leu Ala Phe Asp Ile
1               5                   10

<210> SEQ ID NO 47
<211> LENGTH: 5
<212> TYPE: PRT
<213> ORGANISM: Homo sapiens

<400> SEQUENCE: 47

Ser Tyr Trp Ile Gly
1               5
```

```
<210> SEQ ID NO 48
<211> LENGTH: 17
<212> TYPE: PRT
<213> ORGANISM: Homo sapiens

<400> SEQUENCE: 48

Ile Ile Tyr Pro Gly Asp Ser Asp Thr Arg Tyr Ser Pro Ser Phe Gln
 1               5                  10                  15

Gly

<210> SEQ ID NO 49
<211> LENGTH: 13
<212> TYPE: PRT
<213> ORGANISM: Homo sapiens

<400> SEQUENCE: 49

Arg Thr Ile Val Ala Thr Ile His Trp Ala Ser Asp Tyr
 1               5                  10

<210> SEQ ID NO 50
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 50 cag gtg cag ctg gtg caa tct ggg tct gag ttg aag cag cct ggg gcc      48
Gln Val Gln Leu Val Gln Ser Gly Ser Glu Leu Lys Gln Pro Gly Ala
 1               5                  10                  15 tca gtg aag gtt tcc tgt aag gct tct gga tac acc ttc act cac tat      96
Ser Val Lys Val Ser Cys Lys Ala Ser Gly Tyr Thr Phe Thr His Tyr
             20                  25                  30 ggt ttg cat tgg gtg cga cag gcc cct gga caa ggg ctt gag tgg atg     144
Gly Leu His Trp Val Arg Gln Ala Pro Gly Gln Gly Leu Glu Trp Met
         35                  40                  45 gga tgg ctc aac acc aac act gag aac cca acg ttt gcc cag ggc ttc     192
Gly Trp Leu Asn Thr Asn Thr Glu Asn Pro Thr Phe Ala Gln Gly Phe
     50                  55                  60 aca gga cgg ttt gtc ttc tcc ttg gac acc tct gtc acc acg gca tat     240
Thr Gly Arg Phe Val Phe Ser Leu Asp Thr Ser Val Thr Thr Ala Tyr
 65                  70                  75                  80 ctg cag atc agc agc ctg aag gct gag gac act gcc gta tat tac tgt     288
Leu Gln Ile Ser Ser Leu Lys Ala Glu Asp Thr Ala Val Tyr Tyr Cys
                 85                  90                  95 gcg aga ggg gat atg gta gta ccg act act ata tgg aac tac tac cac     336
Ala Arg Gly Asp Met Val Val Pro Thr Thr Ile Trp Asn Tyr Tyr His
            100                 105                 110 ttc atg gac gtc tgg ggc aac ggc acc ctg gtc acc gtc tcg agt         381
Phe Met Asp Val Trp Gly Asn Gly Thr Leu Val Thr Val Ser Ser
        115                 120                 125

<210> SEQ ID NO 51
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 51 cag gtg cag ctg gtg caa tct ggg tct gag ttg aag cag cct ggg gtc      48
Gln Val Gln Leu Val Gln Ser Gly Ser Glu Leu Lys Gln Pro Gly Val
 1               5                  10                  15
```

```
                 1               5                  10                 15
tca gtg aag gtt tcc tgc aag gct tct gga tac acc ttc act cac tat          96
Ser Val Lys Val Ser Cys Lys Ala Ser Gly Tyr Thr Phe Thr His Tyr
                 20                 25                 30 ggt tta cat tgg gtg cga cag gcc cct gga caa ggg ctt gag tgg atg          144
Gly Leu His Trp Val Arg Gln Ala Pro Gly Gln Gly Leu Glu Trp Met
         35                 40                 45 gga tgg atc aac acc aac act ggg aac cca acg tat gcc cag ggc ttc          192
Gly Trp Ile Asn Thr Asn Thr Gly Asn Pro Thr Tyr Ala Gln Gly Phe
 50                 55                 60 aca gga cgg ttt gtc ttc tcc ttg gac acc tct gtc agc acg gca tat          240
Thr Gly Arg Phe Val Phe Ser Leu Asp Thr Ser Val Ser Thr Ala Tyr
 65                 70                 75                 80 ctg cag atc agc agc cta aag gct gaa gac act gcc gtg tat tac tgt          288
Leu Gln Ile Ser Ser Leu Lys Ala Glu Asp Thr Ala Val Tyr Tyr Cys
                 85                 90                 95 gcg aga ggg gat tta gta gta cca act act ata tgg aac tac tac cac          336
Ala Arg Gly Asp Leu Val Val Pro Thr Thr Ile Trp Asn Tyr Tyr His
         100                105                110 tac atg gag gtc tgg ggc aaa ggc acc ctg gtc acc gtc tcg agt              381
Tyr Met Glu Val Trp Gly Lys Gly Thr Leu Val Thr Val Ser Ser
         115                120                125

<210> SEQ ID NO 52
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 52 cag gtg cag ctg gtg caa tct ggg tct gag ttg aag aag cct ggg gcc          48
Gln Val Gln Leu Val Gln Ser Gly Ser Glu Leu Lys Lys Pro Gly Ala
 1               5                  10                 15 tca gtg atg gtt tcc tgc aag gct tct gga tac acc ttc act cac tat          96
Ser Val Met Val Ser Cys Lys Ala Ser Gly Tyr Thr Phe Thr His Tyr
                 20                 25                 30 gct ttg cat tgg gtg cgc cag gcc cct gga caa ggg ctt gag tgg atg          144
Ala Leu His Trp Val Arg Gln Ala Pro Gly Gln Gly Leu Glu Trp Met
         35                 40                 45 gga tgg ctc aat acc aac act gag aat cca acg tat gcc cag ggc ttc          192
Gly Trp Leu Asn Thr Asn Thr Glu Asn Pro Thr Tyr Ala Gln Gly Phe
 50                 55                 60 aca gga cgg ttt gtc ttc tcc ttg gac acc tct gtc acc acg gca tat          240
Thr Gly Arg Phe Val Phe Ser Leu Asp Thr Ser Val Thr Thr Ala Tyr
 65                 70                 75                 80 ctg cag atc aac agc cta aag gct gag gac act gcc gtg tat tac tgt          288
Leu Gln Ile Asn Ser Leu Lys Ala Glu Asp Thr Ala Val Tyr Tyr Cys
                 85                 90                 95 gcg aga ggg gat atg gta gta cca act act ata tgg aac tac tac tac          336
Ala Arg Gly Asp Met Val Val Pro Thr Thr Ile Trp Asn Tyr Tyr Tyr
         100                105                110 tac atg gac gtc tgg ggc aaa ggg acc acg gtc acc gtc tcg agt              381
Tyr Met Asp Val Trp Gly Lys Gly Thr Thr Val Thr Val Ser Ser
         115                120                125

<210> SEQ ID NO 53
<211> LENGTH: 381
<212> TYPE: DNA
<213> ORGANISM: Homo sapiens
<220> FEATURE:
```

<221> NAME/KEY: CDS
<222> LOCATION: (1)..(381)

<400> SEQUENCE: 53

```
cag gtg cag ctg gtg caa tct ggg tct gag ttg aag cag cct ggg gcc       48
Gln Val Gln Leu Val Gln Ser Gly Ser Glu Leu Lys Gln Pro Gly Ala
1               5                   10                  15 tca gtg aag gtt tcc tgt aag gct tct gga tac acc ttc act cac tat       96
Ser Val Lys Val Ser Cys Lys Ala Ser Gly Tyr Thr Phe Thr His Tyr
            20                  25                  30 gct ttg cat tgg ttg cga cag gcc cct gga caa ggg ctt gag tgg atg      144
Ala Leu His Trp Leu Arg Gln Ala Pro Gly Gln Gly Leu Glu Trp Met
        35                  40                  45 gga tgg ctc aac acc aac act gag aac cca acg ttt gcc cag ggc ttc      192
Gly Trp Leu Asn Thr Asn Thr Glu Asn Pro Thr Phe Ala Gln Gly Phe
    50                  55                  60 aca gga cgt ttt gtc ttc tct ttg gac acc tct gtc acc acg gca tat      240
Thr Gly Arg Phe Val Phe Ser Leu Asp Thr Ser Val Thr Thr Ala Tyr
65                  70                  75                  80 ctg cag atc agc agc ctg aag gct gag gac act gcc gta tat tac tgt      288
Leu Gln Ile Ser Ser Leu Lys Ala Glu Asp Thr Ala Val Tyr Tyr Cys
                85                  90                  95 gcg aga ggg gat atg gta gta ccg act act ata tgg aac tac tac cac      336
Ala Arg Gly Asp Met Val Val Pro Thr Thr Ile Trp Asn Tyr Tyr His
            100                 105                 110 ttc atg gac gtc tgg ggc aac ggg acc acg gtc acc gtc tcg agt          381
Phe Met Asp Val Trp Gly Asn Gly Thr Thr Val Thr Val Ser Ser
        115                 120                 125
```

<210> SEQ ID NO 54
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 54

```
cag gtg cag ctg gtg caa tct ggg tct gag ttg aag cag cct ggg gcc       48
Gln Val Gln Leu Val Gln Ser Gly Ser Glu Leu Lys Gln Pro Gly Ala
1               5                   10                  15 tca gtg aag gtt tcc tgt aag gct tct gga tac acc ttc act cac tat       96
Ser Val Lys Val Ser Cys Lys Ala Ser Gly Tyr Thr Phe Thr His Tyr
            20                  25                  30 gct ttg cat tgg ttg cga cag gcc cct gga caa ggg ctt gag tgg atg      144
Ala Leu His Trp Leu Arg Gln Ala Pro Gly Gln Gly Leu Glu Trp Met
        35                  40                  45 gga tgg ctc aac acc aac act gag aac cca acg ttt gcc cag ggc ttc      192
Gly Trp Leu Asn Thr Asn Thr Glu Asn Pro Thr Phe Ala Gln Gly Phe
    50                  55                  60 aca gga cgt ttt gtc ttc tct ttg gac acc tct gtc acc acg gca tat      240
Thr Gly Arg Phe Val Phe Ser Leu Asp Thr Ser Val Thr Thr Ala Tyr
65                  70                  75                  80 ctg cag atc agc agc ctg aag gct gag gac act gcc gta tat tac tgt      288
Leu Gln Ile Ser Ser Leu Lys Ala Glu Asp Thr Ala Val Tyr Tyr Cys
                85                  90                  95 gcg aga ggg gat atg gta gta ccg act act ata tgg aac tac tac cac      336
Ala Arg Gly Asp Met Val Val Pro Thr Thr Ile Trp Asn Tyr Tyr His
            100                 105                 110 ttc atg gac gtc tgg ggc cag ggg acc acg gtc acc gtc tcg agt          381
Phe Met Asp Val Trp Gly Gln Gly Thr Thr Val Thr Val Ser Ser
        115                 120                 125
```

```
<210> SEQ ID NO 55
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 55 gac atc cag atg acc cag tct cca tcc tcc ctg tct gca tct gta gga      48
Asp Ile Gln Met Thr Gln Ser Pro Ser Ser Leu Ser Ala Ser Val Gly
1               5                   10                  15 gac aga gtc acc atc act tgc cgg gca agt cag agc att agc agc tac      96
Asp Arg Val Thr Ile Thr Cys Arg Ala Ser Gln Ser Ile Ser Ser Tyr
            20                  25                  30 tta aat tgg tat cag cag aaa cca ggg aaa gcc cct aag ctc ctg atc     144
Leu Asn Trp Tyr Gln Gln Lys Pro Gly Lys Ala Pro Lys Leu Leu Ile
        35                  40                  45 tat gct gca tcc agt ttg caa agt ggg gtc cca tca agg ttc agt ggc     192
Tyr Ala Ala Ser Ser Leu Gln Ser Gly Val Pro Ser Arg Phe Ser Gly
    50                  55                  60 agt gga tct ggg aca gat ttc act ctc acc atc agc agt ctg caa cct     240
Ser Gly Ser Gly Thr Asp Phe Thr Leu Thr Ile Ser Ser Leu Gln Pro
65                  70                  75                  80 gaa gat ttt gca act tac tac tgt caa cag agt tac agt acc cct cca     288
Glu Asp Phe Ala Thr Tyr Tyr Cys Gln Gln Ser Tyr Ser Thr Pro Pro
                85                  90                  95 acg ttc ggc caa ggg acc aag gtg gag atc aaa                          321
Thr Phe Gly Gln Gly Thr Lys Val Glu Ile Lys
            100                 105

<210> SEQ ID NO 56
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 56 cag gtg cag ctg gtg cag tct ggg gcc gag gtg aaa aag ccc ggg gag      48
Gln Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac      96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc ttc     192
Gly Ile Ile Tyr Pro Gly Asp Ser Asp Thr Arg Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc ata tat tac tgt     288
Leu Gln Trp Ser Ser Leu Lys Ala Ser Asp Thr Ala Ile Tyr Tyr Cys
                85                  90                  95 gcg aga aag acg att gtt gga gtg gtt atg acg gct ttt gat atc tgg     336
Ala Arg Lys Thr Ile Val Gly Val Val Met Thr Ala Phe Asp Ile Trp
            100                 105                 110
```

```
ggc caa ggg aca atg gtc acc gtc tcc agt                              366
Gly Gln Gly Thr Met Val Thr Val Ser Ser
        115                 120

<210> SEQ ID NO 57
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 57 gag gtg cag ctg gtg cag tct gga gca gag gtg aaa aag ccc ggg gag    48
Glu Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac    96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg   144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc ttc   192
Gly Ile Ile Tyr Pro Gly Asp Ser Asp Thr Arg Tyr Ser Pro Ser Phe
    50                  55                  60 caa ggc cag gtc acc atc tca gcc gac aag tcc atc agc acc gcc tac   240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc atg tat tat tgt   288
Leu Gln Trp Ser Ser Leu Lys Ala Ser Asp Thr Ala Met Tyr Tyr Cys
                85                  90                  95 gtg cga cag act ata gtg gct acg gta atg aat gct ttt gat atc tgg   336
Val Arg Gln Thr Ile Val Ala Thr Val Met Asn Ala Phe Asp Ile Trp
            100                 105                 110 ggc caa ggg acc acg gtc acc gtc tcc agt                            366
Gly Gln Gly Thr Thr Val Thr Val Ser Ser
        115                 120

<210> SEQ ID NO 58
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 58 cag gtg cag ctg gtg cag tct ggg gca gag gtg aaa aag tcc ggg gag    48
Gln Val Gln Leu Val Gln Ser Gly Ala Glu Val Lys Lys Ser Gly Glu
1               5                   10                  15 tct ctg aag atc tcc tgt aag ggt tct gga ttc agc ttt acc agc tac    96
Ser Leu Lys Ile Ser Cys Lys Gly Ser Gly Phe Ser Phe Thr Ser Tyr
            20                  25                  30 tgg atc gcc tgg gtg cgc cag atg ccc ggg aaa ggc ctg gag tgg atg   144
Trp Ile Ala Trp Val Arg Gln Met Pro Gly Lys Gly Leu Glu Trp Met
        35                  40                  45 ggg atc atc tat cct ggt gac tct gat acc aga tat agc ccg tcc ttc   192
Gly Ile Ile Tyr Pro Gly Asp Ser Asp Thr Arg Tyr Ser Pro Ser Phe
    50                  55                  60 caa ggc cag gtc acc atc tca gcc gac aag tcc ttc acc acc gcc tac   240
Gln Gly Gln Val Thr Ile Ser Ala Asp Lys Ser Phe Thr Thr Ala Tyr
65                  70                  75                  80 ctg cag tgg aac agc ctg aag gcc tcg gac acc gcc ata tat tac tgt   288
Leu Gln Trp Asn Ser Leu Lys Ala Ser Asp Thr Ala Ile Tyr Tyr Cys
```

```
Leu Gln Trp Asn Ser Leu Lys Ala Ser Asp Thr Ala Ile Tyr Tyr Cys
                 85                  90                  95 gcg aga cat act ata gtg gct acg ata tac aat gct ttt gat ttc tgg          336
Ala Arg His Thr Ile Val Ala Thr Ile Tyr Asn Ala Phe Asp Phe Trp
            100                 105                 110 ggc caa ggg aca atg gtc acc gtc tcc agt                                  366
Gly Gln Gly Thr Met Val Thr Val Ser Ser
            115                 120

<210> SEQ ID NO 59
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 59 cag gtg cag ctg gtg cag tct ggg gca gag gtg aaa aag ccc ggg gag           48
Gln Val Gln Leu Val Gln Ser Gly Ala Glu Val Lys Lys Pro Gly Glu
1               5                   10                  15 tct ctg aag atc tcc tgt aag ggt tct gga tac agt ttt atc agc tac           96
Ser Leu Lys Ile Ser Cys Lys Gly Ser Gly Tyr Ser Phe Ile Ser Tyr
            20                  25                  30 tgg atc ggc tgg gtg cgc cag atg ccc ggg aaa ggc ctg gag tgg atg          144
Trp Ile Gly Trp Val Arg Gln Met Pro Gly Lys Gly Leu Glu Trp Met
        35                  40                  45 ggg atc atc tgg cct ggt gac tct gat acc aga tac agt ccg tcc ttc          192
Gly Ile Ile Trp Pro Gly Asp Ser Asp Thr Arg Tyr Ser Pro Ser Phe
    50                  55                  60 caa ggc cag gtc acc atc tca gcc gac aag tcc atc aat gtc gcc tac          240
Gln Gly Gln Val Thr Ile Ser Ala Asp Lys Ser Ile Asn Val Ala Tyr
65                  70                  75                  80 ctg cag tgg agc agc ctg aag gcc tcg gac acc gcc ttg tat tat tgt          288
Leu Gln Trp Ser Ser Leu Lys Ala Ser Asp Thr Ala Leu Tyr Tyr Cys
                85                  90                  95 gtg aga caa acg att gtg gct acg act ggg ctt gct ttt gat atc tgg          336
Val Arg Gln Thr Ile Val Ala Thr Thr Gly Leu Ala Phe Asp Ile Trp
            100                 105                 110 ggc caa ggc acc ctg gtc acc gtc tcc agt                                  366
Gly Gln Gly Thr Leu Val Thr Val Ser Ser
            115                 120

<210> SEQ ID NO 60
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 60 gag gtg cag ctg gtg cag tct gga gca gag gtg aaa aag ccc ggg gag           48
Glu Val Gln Leu Val Gln Ser Gly Ala Glu Val Lys Lys Pro Gly Glu
1               5                   10                  15 tct ctg aag atc tcc tgt aag ggt tct gga tac agc ttt aca agt tat           96
Ser Leu Lys Ile Ser Cys Lys Gly Ser Gly Tyr Ser Phe Thr Ser Tyr
            20                  25                  30 tgg atc ggc tgg gtg cgc cag atg ccc ggg aaa ggc ctg gag tgg atg          144
Trp Ile Gly Trp Val Arg Gln Met Pro Gly Lys Gly Leu Glu Trp Met
        35                  40                  45 ggg atc atc tat cct ggt gac tct gat acc aga tac agc ccg tcc ttc          192
Gly Ile Ile Tyr Pro Gly Asp Ser Asp Thr Arg Tyr Ser Pro Ser Phe
```

```
                    50                  55                  60
caa ggc cag gtc acc atc tca gcc gat aag tcc atc aac acc gcc tac       240
Gln Gly Gln Val Thr Ile Ser Ala Asp Lys Ser Ile Asn Thr Ala Tyr
 65                  70                  75                  80 ctg cag tgg agc agc ctg aag gcc tcg gac acc gcc atg tat tac tgt       288
Leu Gln Trp Ser Ser Leu Lys Ala Ser Asp Thr Ala Met Tyr Tyr Cys
                 85                  90                  95 gcg aga cgg acc ata gtg gca acg att cac tgg gct tct gac tac tgg       336
Ala Arg Arg Thr Ile Val Ala Thr Ile His Trp Ala Ser Asp Tyr Trp
            100                 105                 110 ggc cag ggg aca atg gtc acc gtc tcc agt                               366
Gly Gln Gly Thr Met Val Thr Val Ser Ser
        115                 120

<210> SEQ ID NO 61
<211> LENGTH: 11
<212> TYPE: PRT
<213> ORGANISM: Homo sapiens

<400> SEQUENCE: 61

Trp Gly Lys Gly Thr Thr Val Thr Val Ser Ser
1               5                   10

<210> SEQ ID NO 62
<211> LENGTH: 122
<212> TYPE: PRT
<213> ORGANISM: Homo sapiens

<400> SEQUENCE: 62

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Ile Tyr Tyr Cys
                85                  90                  95

Ala Arg Lys Thr Ile Val Gly Val Met Thr Ala Phe Asp Ile Trp
            100                 105                 110

Gly Arg Gly Thr Met Val Thr Val Ser Ser
        115                 120

<210> SEQ ID NO 63
<211> LENGTH: 122
<212> TYPE: PRT
<213> ORGANISM: Homo sapiens

<400> SEQUENCE: 63

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
```

```
                    50                  55                  60
Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Val Arg Gln Thr Ile Val Ala Thr Val Met Asn Ala Phe Asp Ile Trp
                100                 105                 110

Gly Arg Gly Thr Thr Val Thr Val Ser Ser
            115                 120
```

<210> SEQ ID NO 64
<211> LENGTH: 122
<212> TYPE: PRT
<213> ORGANISM: Homo sapiens

<400> SEQUENCE: 64

```
Gln Val Gln Leu Val Gln Ser Gly Ala Glu Val Lys Lys Ser Gly Glu
 1               5                  10                  15

Ser Leu Lys Ile Ser Cys Lys Gly Ser Gly Phe Ser Phe Thr Ser Tyr
                20                  25                  30

Trp Ile Ala Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
         50                  55                  60

Gln Gly Gln Val Thr Ile Ser Ala Asp Lys Ser Phe Thr Thr Ala Tyr
 65                  70                  75                  80

Leu Gln Trp Asn Ser Leu Lys Ala Ser Asp Thr Ala Ile Tyr Tyr Cys
                 85                  90                  95

Ala Arg His Thr Ile Val Ala Thr Ile Tyr Asn Ala Phe Asp Phe Trp
                100                 105                 110

Gly Arg Gly Thr Met Val Thr Val Ser Ser
            115                 120
```

<210> SEQ ID NO 65
<211> LENGTH: 122
<212> TYPE: PRT
<213> ORGANISM: Homo sapiens

<400> SEQUENCE: 65

```
Gln Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Ile Ser Tyr
                20                  25                  30

Trp Ile Gly Trp Val Arg Gln Met Pro Gly Lys Gly Leu Glu Trp Met
             35                  40                  45

Gly Ile Ile Trp Pro Gly Asp Ser Asp Thr Arg Tyr Ser Pro Ser Phe
         50                  55                  60

Gln Gly Gln Val Thr Ile Ser Ala Asp Lys Ser Ile Asn Val Ala Tyr
 65                  70                  75                  80

Leu Gln Trp Ser Ser Leu Lys Ala Ser Asp Thr Ala Leu Tyr Tyr Cys
                 85                  90                  95

Val Arg Gln Thr Ile Val Ala Thr Gly Leu Ala Phe Asp Ile Trp
                100                 105                 110

Gly Arg Gly Thr Leu Val Thr Val Ser Ser
            115                 120
```

-continued

```
<210> SEQ ID NO 66
<211> LENGTH: 122
<212> TYPE: PRT
<213> ORGANISM: Homo sapiens

<400> SEQUENCE: 66

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Thr Ile Val Ala Thr Ile His Trp Ala Ser Asp Tyr Trp
            100                 105                 110

Gly Arg Gly Thr Met Val Thr Val Ser Ser
        115                 120

<210> SEQ ID NO 67
<211> LENGTH: 4
<212> TYPE: PRT
<213> ORGANISM: Artificial Sequence
<220> FEATURE:
<223> OTHER INFORMATION: Synthetic sequence

<400> SEQUENCE: 67

Gly Lys Lys Ala
1

<210> SEQ ID NO 68
<211> LENGTH: 5
<212> TYPE: PRT
<213> ORGANISM: Artificial Sequence
<220> FEATURE:
<223> OTHER INFORMATION: Synthetic sequence

<400> SEQUENCE: 68

Gly Lys Ala Lys Ala
1               5

<210> SEQ ID NO 69
<211> LENGTH: 4
<212> TYPE: PRT
<213> ORGANISM: Artificial Sequence
<220> FEATURE:
<223> OTHER INFORMATION: Synthetic sequence

<400> SEQUENCE: 69

Gly Arg Arg Ala
1

<210> SEQ ID NO 70
<211> LENGTH: 5
<212> TYPE: PRT
<213> ORGANISM: Artificial Sequence
<220> FEATURE:
<223> OTHER INFORMATION: Synthetic sequence

<400> SEQUENCE: 70
```

Gly Arg Ala Arg Ala
1               5

<210> SEQ ID NO 71
<211> LENGTH: 331
<212> TYPE: PRT
<213> ORGANISM: Homo sapiens

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Lys Pro Pro Ser Arg Glu Glu
225                 230                 235                 240

Met Thr Lys Asn Gln Val Ser Leu Lys Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Gly
                325                 330

<210> SEQ ID NO 72
<211> LENGTH: 334
<212> TYPE: PRT

<213> ORGANISM: Homo sapiens

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Lys Pro Pro Ser Arg Glu Glu
225                 230                 235                 240

Met Thr Lys Asn Gln Val Ser Leu Lys Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Gly Lys Lys Ala
                325                 330

<210> SEQ ID NO 73
<211> LENGTH: 335
<212> TYPE: PRT
<213> ORGANISM: Homo sapiens

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                    20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Gly Arg Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Lys Pro Pro Ser Arg Glu Glu
225                 230                 235                 240
Met Thr Lys Asn Gln Val Ser Leu Lys Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys Gly Lys Ala Lys Ala
                325                 330                 335

<210> SEQ ID NO 74
<211> LENGTH: 334
<212> TYPE: PRT
<213> ORGANISM: Homo sapiens

<400> SEQUENCE: 74

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Gly Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Lys Pro Pro Ser Arg Glu Glu
225                 230                 235                 240

Met Thr Lys Asn Gln Val Ser Leu Lys Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys Gly Arg Arg Ala
            325                 330

<210> SEQ ID NO 75
<211> LENGTH: 335
<212> TYPE: PRT
<213> ORGANISM: Homo sapiens

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

```
Pro Ala Pro Glu Leu Gly Arg Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Lys Pro Pro Ser Arg Glu Glu
225                 230                 235                 240
Met Thr Lys Asn Gln Val Ser Leu Lys Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys Gly Arg Ala Arg Ala
                325                 330                 335

<210> SEQ ID NO 76
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 76 cag gtg cag ctg gtg cag tct ggg gcc gag gtg aaa aag ccc ggg gag      48
Gln Val Gln Leu Val Gln Ser Gly Ala Glu Val Lys Lys Pro Gly Glu
1               5                   10                  15 tct ctg aag atc tcc tgt aag ggt tct gga tac agc ttt acc agc tac      96
Ser Leu Lys Ile Ser Cys Lys Gly Ser Gly Tyr Ser Phe Thr Ser Tyr
                20                  25                  30 tgg atc ggc tgg gtg cgc cag atg ccc ggg aaa ggc ctg gag tgg atg     144
Trp Ile Gly Trp Val Arg Gln Met Pro Gly Lys Gly Leu Glu Trp Met
            35                  40                  45 ggg atc atc tat cct ggt gac tct gat acc aga tac agc ccg tcc ttc     192
Gly Ile Ile Tyr Pro Gly Asp Ser Asp Thr Arg Tyr Ser Pro Ser Phe
        50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agt agc ctg aag gcc tcg gac acc gcc ata tat tac tgt     288
Leu Gln Trp Ser Ser Leu Lys Ala Ser Asp Thr Ala Ile Tyr Tyr Cys
                85                  90                  95 gcg aga aag acg att gtt gga gtg gtt atg acg gct ttt gat atc tgg     336
Ala Arg Lys Thr Ile Val Gly Val Val Met Thr Ala Phe Asp Ile Trp
```

| | | |
|---|---|---|
| Ala Arg Lys Thr Ile Val Gly Val Val Met Thr Ala Phe Asp Ile Trp<br>            100                    105                    110 | | |
| ggc cga ggg aca atg gtc acc gtc tcc agt<br>Gly Arg Gly Thr Met Val Thr Val Ser Ser<br>            115                    120 | | 366 |

<210> SEQ ID NO 77
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 77

| | | |
|---|---|---|
| gag gtg cag ctg gtg cag tct gga gca gag gtg aaa aag ccc ggg gag<br>Glu Val Gln Leu Val Gln Ser Gly Ala Glu Val Lys Lys Pro Gly Glu<br>1                 5                      10                  15 | | 48 |
| tct ctg aag atc tcc tgt aag ggt tct gga tac agc ttt acc agc tac<br>Ser Leu Lys Ile Ser Cys Lys Gly Ser Gly Tyr Ser Phe Thr Ser Tyr<br>            20                    25                    30 | | 96 |
| tgg atc ggc tgg gtg cgc cag atg ccc ggg aaa ggc ctg gag tgg atg<br>Trp Ile Gly Trp Val Arg Gln Met Pro Gly Lys Gly Leu Glu Trp Met<br>            35                    40                    45 | | 144 |
| ggg atc atc tat cct ggt gac tct gat acc aga tac agc ccg tcc ttc<br>Gly Ile Ile Tyr Pro Gly Asp Ser Asp Thr Arg Tyr Ser Pro Ser Phe<br> 50                     55                    60 | | 192 |
| caa ggc cag gtc acc atc tca gcc gac aag tcc atc agc acc gcc tac<br>Gln Gly Gln Val Thr Ile Ser Ala Asp Lys Ser Ile Ser Thr Ala Tyr<br>65                70                    75                  80 | | 240 |
| ctg cag tgg agc agc ctg aag gcc tcg gac acc gcc atg tat tat tgt<br>Leu Gln Trp Ser Ser Leu Lys Ala Ser Asp Thr Ala Met Tyr Tyr Cys<br>                    85                    90                    95 | | 288 |
| gtg cga cag act ata gtg gct acg gta atg aat gct ttt gat atc tgg<br>Val Arg Gln Thr Ile Val Ala Thr Val Met Asn Ala Phe Asp Ile Trp<br>            100                    105                    110 | | 336 |
| ggc cga ggg acc acg gtc acc gtc tcc agt<br>Gly Arg Gly Thr Thr Val Thr Val Ser Ser<br>            115                    120 | | 366 |

<210> SEQ ID NO 78
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 78

| | | |
|---|---|---|
| cag gtg cag ctg gtg cag tct ggg gca gag gtg aaa aag tcc ggg gag<br>Gln Val Gln Leu Val Gln Ser Gly Ala Glu Val Lys Lys Ser Gly Glu<br>1                 5                      10                  15 | | 48 |
| tct ctg aag atc tcc tgt aag ggt tct gga ttc agc ttt acc agc tac<br>Ser Leu Lys Ile Ser Cys Lys Gly Ser Gly Phe Ser Phe Thr Ser Tyr<br>            20                    25                    30 | | 96 |
| tgg atc gcc tgg gtg cgc cag atg ccc ggg aaa ggc ctg gag tgg atg<br>Trp Ile Ala Trp Val Arg Gln Met Pro Gly Lys Gly Leu Glu Trp Met<br>            35                    40                    45 | | 144 |
| ggg atc atc tat cct ggt gac tct gat acc aga tat agc ccg tcc ttc<br>Gly Ile Ile Tyr Pro Gly Asp Ser Asp Thr Arg Tyr Ser Pro Ser Phe<br> 50                     55                    60 | | 192 |
| caa ggc cag gtc acc atc tca gcc gac aag tcc ttc acc acc gcc tac<br>Gln Gly Gln Val Thr Ile Ser Ala Asp Lys Ser Phe Thr Thr Ala Tyr | | 240 |

```
                  65                  70                  75                  80 ctg cag tgg aac agc ctg aag gcc tcg gac acc gcc ata tat tac tgt      288
Leu Gln Trp Asn Ser Leu Lys Ala Ser Asp Thr Ala Ile Tyr Tyr Cys
                85                  90                  95 gcg aga cat act ata gtg gct acg ata tac aat gct ttt gat ttc tgg      336
Ala Arg His Thr Ile Val Ala Thr Ile Tyr Asn Ala Phe Asp Phe Trp
                100                 105                 110 ggc cga ggg aca atg gtc acc gtc tcc agt                              366
Gly Arg Gly Thr Met Val Thr Val Ser Ser
        115                 120

<210> SEQ ID NO 79
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 79 cag gtg cag ctg gtg cag tct ggg gca gag gtg aaa aag ccc ggg gag       48
Gln Val Gln Leu Val Gln Ser Gly Ala Glu Val Lys Lys Pro Gly Glu
1               5                   10                  15 tct ctg aag atc tcc tgt aag ggt tct gga tac agt ttt atc agc tac       96
Ser Leu Lys Ile Ser Cys Lys Gly Ser Gly Tyr Ser Phe Ile Ser Tyr
                20                  25                  30 tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
            35                  40                  45 ggg atc atc tgg cct ggt gac tct gat acc aga tac agt ccg tcc ttc      192
Gly Ile Ile Trp Pro Gly Asp Ser Asp Thr Arg Tyr Ser Pro Ser Phe
        50                  55                  60 caa ggc cag gtc acc atc tca gcc gac aag tcc atc aat gtc gcc tac      240
Gln Gly Gln Val Thr Ile Ser Ala Asp Lys Ser Ile Asn Val Ala Tyr
65                  70                  75                  80 ctg cag tgg agc agc ctg aag gcc tcg gac acc gcc ttg tat tat tgt      288
Leu Gln Trp Ser Ser Leu Lys Ala Ser Asp Thr Ala Leu Tyr Tyr Cys
                85                  90                  95 gtg aga caa acg att gtg gct acg act ggg ctt gct ttt gat atc tgg      336
Val Arg Gln Thr Ile Val Ala Thr Thr Gly Leu Ala Phe Asp Ile Trp
                100                 105                 110 ggc cga ggc acc ctg gtc acc gtc tcc agt                              366
Gly Arg Gly Thr Leu Val Thr Val Ser Ser
        115                 120

<210> SEQ ID NO 80
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 80 gag gtg cag ctg gtg cag tct gga gca gag gtg aaa aag ccc ggg gag       48
Glu Val Gln Leu Val Gln Ser Gly Ala Glu Val Lys Lys Pro Gly Glu
1               5                   10                  15 tct ctg aag atc tcc tgt aag ggt tct gga tac agc ttt aca agt tat       96
Ser Leu Lys Ile Ser Cys Lys Gly Ser Gly Tyr Ser Phe Thr Ser Tyr
                20                  25                  30 tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
            35                  40                  45
```

-continued

```
ggg atc atc tat cct ggt gac tct gat acc aga tac agc ccg tcc ttc    192
Gly Ile Ile Tyr Pro Gly Asp Ser Asp Thr Arg Tyr Ser Pro Ser Phe
     50                  55                  60 caa ggc cag gtc acc atc tca gcc gat aag tcc atc aac acc gcc tac    240
Gln Gly Gln Val Thr Ile Ser Ala Asp Lys Ser Ile Asn Thr Ala Tyr
65                  70                  75                  80 ctg cag tgg agc agc ctg aag gcc tcg gac acc gcc atg tat tac tgt    288
Leu Gln Trp Ser Ser Leu Lys Ala Ser Asp Thr Ala Met Tyr Tyr Cys
                 85                  90                  95 gcg aga cgg acc ata gtg gca acg att cac tgg gct tct gac tac tgg    336
Ala Arg Arg Thr Ile Val Ala Thr Ile His Trp Ala Ser Asp Tyr Trp
             100                 105                 110 ggc cga ggg aca atg gtc acc gtc tcc agt                            366
Gly Arg Gly Thr Met Val Thr Val Ser Ser
         115                 120
```